US007485722B2

(12) United States Patent
Egle et al.

(10) Patent No.: US 7,485,722 B2
(45) Date of Patent: Feb. 3, 2009

(54) SPIRO-OXAZOLIDINONE COMPOUNDS AND THEIR USE AS METABOTROPIC GLUTAMATE RECEPTOR POTENTIATORS

(75) Inventors: Ian Egle, North York (CA); Babu Joseph, Oakville (CA); Abdelmalik Slassi, Mississauga (CA); Methvin Isaac, Brampton (CA); Fupeng Ma, Melrose, MA (US); Joshua Clayton, Oakville (CA)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 11/898,491

(22) Filed: Sep. 12, 2007

(65) Prior Publication Data

US 2008/0125431 A1 May 29, 2008

Related U.S. Application Data

(60) Provisional application No. 60/825,538, filed on Sep. 13, 2006.

(51) Int. Cl.
*C07D 273/04* (2006.01)
*C07D 263/52* (2006.01)
*C07D 498/00* (2006.01)

(52) U.S. Cl. ....................................... 544/137; 548/216

(58) Field of Classification Search ................. 548/216; 544/70, 230, 137; 546/15; 514/376, 254.02, 514/278, 256, 255.05, 236.8
See application file for complete search history.

(56) References Cited

U.S. PATENT DOCUMENTS 3,491,110 A * 1/1970 Maillard et al. ............. 548/216
4,600,782 A 7/1986 Georgiev et al.

FOREIGN PATENT DOCUMENTS

DE 25 38 424 A1 3/1977
DE 197 45 886 A1 4/1999
GB 829 048 2/1960
GB 1 098 835 1/1969
WO WO-02/083649 A1 10/2002
WO WO-03/020721 A1 3/2003

OTHER PUBLICATIONS

Schoepp et al., Trends Pharmacol. Sci., vol. 14, pp. 13-20 (1993).
Schoepp, Neurochem, Int., vol. 24, No. 5, pp. 439-449, (1994).
Pin et al., Neuropharmacology, vol. 34, No. 1, pp. 1-26 (1995).
Bordi and Ugolini, Prog. Neurobiol. vol. 59, pp. 55-79, (1999).
Nakanishi, Neuron, vol. 13, pp. 1031-1037, (Nov. 1994).
Knopfel et al., J. Med. Chem., vol. 38, No. 9, pp. 1417-1426, (Apr. 28, 1995).
Bashir et al., Nature, vol. 363, pp. 347-350, (May 24, 1993).
Bortolotto et al. Nature, vol. 368, pp. 740-743, (Apr. 21, 1994).
Aiba et al., Cell, vol. 79, pp. 365-375, (Oct. 21, 1994).
Aiba et al., Cell, vol. 79, pp. 377-388, (Oct. 21, 1994).
Meller et al., Neuroreport, vol. 4, No. 7, pp. 879-882 (Jul. 1993).
Bordi and Ugolini, Brain Res., vol. 871, pp. 223-233, (2000).
Pin et al., Eur. J. Pharmacol. vol. 375, pp. 277-294 (1999).

* cited by examiner

*Primary Examiner*—Kamal A Saeed
*Assistant Examiner*—Kristin Bianchi
(74) *Attorney, Agent, or Firm*—Birch, Stewart, Kolasch & Birch, LLP

(57) ABSTRACT

Compounds in accord with Formula I:

Formula I

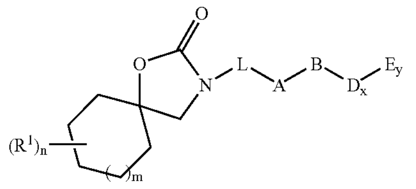

wherein $R^1$, L, A, B, D, E, m, n, x and y are as defined in the description, processes for the preparation of such compounds and to new intermediates employed in the preparation thereof, pharmaceutical compositions containing such compounds, and the use of such compounds in therapy and for the treatment of diseases mentioned in the specification.

13 Claims, No Drawings

SPIRO-OXAZOLIDINONE COMPOUNDS AND THEIR USE AS METABOTROPIC GLUTAMATE RECEPTOR POTENTIATORS

This Nonprovisional application claims priority under 35 U.S.C. § 119(e) on U.S. Provisional Application No(s). 60/825,538 filed on Sep. 13, 2006 the entire contents of which are hereby incorporated by reference.

BACKGROUND OF THE INVENTION

The present invention relates to novel compounds which are potentiators of glutamate receptors, methods for their preparation, pharmaceutical compositions containing them and their use in therapy.

The metabotropic glutamate receptors (mGluR) constitute a family of GTP-binding-protein (G-protein) coupled receptors that are activated by glutamate, and have important roles in synaptic activity in the central nervous system, including neural plasticity, neural development and neurodegeneration.

Activation of mGluRs in intact mammalian neurons elicits one or more of the following responses: activation of phospholipase C; increases in phosphoinositide (PI) hydrolysis; intracellular calcium release; activation of phospholipase D; activation or inhibition of adenyl cyclase; increases or decreases in the formation of cyclic adenosine monophosphate (cAMP); activation of guanylyl cyclase; increases in the formation of cyclic guanosine monophosphate (cGMP); activation of phospholipase $A_2$; increases in arachidonic acid release; and increases or decreases in the activity of voltage- and ligand-gated ion channels (Schoepp et al., 1993, Trends Pharmacol. Sci., 14:13; Schoepp, 1994, Neurochem. Int., 24:439; Pin et al., 1995, Neuropharmacology 34:1; Bordi & Ugolini, 1999, Prog. Neurobiol. 59:55).

Eight mGluR subtypes have been identified, which are divided into three groups based upon primary sequence similarity, signal transduction linkages, and pharmacological profile. Group-I includes mGluR1 and mGluR5, which activate phospholipase C and the generation of an intracellular calcium signal. The Group-II (mGluR2 and mGluR3) and Group-III (mGluR4, mGluR6, mGluR7, and mGluR8) mGluRs mediate an inhibition of adenylyl cyclase activity and cyclic AMP levels. For a review, see Pin et al., 1999, Eur. J. Pharmacol., 375:277-294.

Members of the mGluR family of receptors are implicated in a number of normal processes in the mammalian CNS, and are important targets for compounds for the treatment of a variety of neurological and psychiatric disorders. Activation of mGluRs is required for induction of hippocampal long-term potentiation and cerebellar long-term depression (Bashir et al., 1993, Nature, 363:347; Bortolotto et al., 1994, Nature, 368:740; Aiba et al., 1994, Cell, 79:365; Aiba et al., 1994, Cell, 79:377). A role for mGluR activation in nociception and analgesia also has been demonstrated (Meller et al., 1993, Neuroreport, 4: 879; Bordi & Ugolini, 1999, Brain Res., 871:223). In addition, mGluR activation has been suggested to play a modulatory role in a variety of other normal processes including synaptic transmission, neuronal development, apoptotic neuronal death, synaptic plasticity, spatial learning, olfactory memory, central control of cardiac activity, waking, motor control and control of the vestibulo-ocular reflex (Nakanishi, 1994, Neuron, 13:1031; Pin et al., 1995, Neuropharmacology, supra; Knopfel et al., 1995, J. Med. Chem., 38:1417).

Recent advances in the elucidation of the neurophysiological roles of mGluRs have established these receptors as promising drug targets in the therapy of acute and chronic neurological and psychiatric disorders and chronic and acute pain disorders. Because of the physiological and pathophysiological significance of the mGluRs, there is a need for new drugs and compounds that can modulate mGluR function.

SUMMARY OF THE INVENTION

This invention provides, as one object, compounds of Formula I,

Formula I

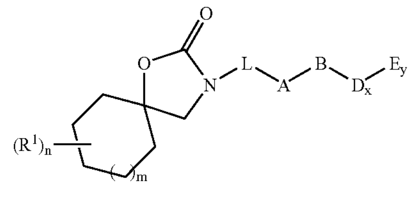

wherein:

$R^1$ is selected from the group consisting of H, hydroxy, F, Cl, Br, I, nitro, CN, alkyl, alkylhalo, O-alkyl, O-alkylhalo, alkenyl, O-alkenyl, alkynyl, O-alkynyl, methylenedioxy and ethylenedioxy;

L is selected from the group consisting of alkylene, alkenylene and alkynylene wherein any hydrogen atom of L may be independently substituted with one or more substituents selected from the group consisting of hydroxy, F, Cl, Br, I, alkyl, alkylhalo and O-alkyl;

A is selected from the group consisting of aryl and heteroaryl;

B is selected from the group consisting of alkylene, aryl, heteroaryl, cycloalkyl and heterocycloalkyl;

D is selected from the group consisting of alkylene, O,O-alkylene and alkylene-O;

E is selected from the group consisting of aryl, heteroaryl, cycloalkyl and heterocycloalkyl;

m and n are independently selected from the group consisting of 0, 1, 2, 3 and 4;

x and y are independently selected from the group consisting of 0 and 1;

wherein any of A, B and E may be substituted with up to 4 substituents independently selected from the group consisting of hydroxy, F, Cl, Br, I, nitro, CN, alkyl, alkylhalo, O-alkyl, O-alkylhalo, alkenyl, O-alkenyl, alkynyl, O-alkynyl, alkyleneO$R^2$, O-alkyleneO$R^2$, (CO)$R^2$, O(CO)$R^2$, alkyleneO(CO)$R^2$, alkylene(CO)$R^2$, O-alkylene(CO)$R^2$, $CO_2R$, alkylene$CO_2R^2$, O-alkylene$CO_2R^2$, alkylenecyano, O-alkylenecyano, O(CN)O$R^2$, $NR^2R^3$, alkylene$NR^2R^3$, O-alkylene$NR^2R^3$, (CO)$NR^2R^3$, alkylene(CO)$NR^2R^3$, O—(CO)$NR^2R^3$, O-alkylene(CO)$NR^2R^3$, $NR^2$(CO)$R^3$, alkylene$NR^2$(CO)$R^3$, O-alkylene$NR^2$(CO)$R^3$, $NR^2$(CO)$NR^3R^4$, alkylene$NR^2$(CO)$NR^3R^4$, and wherein $R^2$ and $R^4$ are independently selected from the group consisting of H and alkyl, and $R^3$ is selected from the group consisting of H, alkyl and alkylene-$NR^2R^4$.

Another object of the invention is to provide a pharmaceutical composition comprising a compound according to Formula I together with a pharmaceutically acceptable carrier or excipient.

Yet another object of the invention is a method for the treatment or prevention of neurological and psychiatric disorders associated with glutamate dysfunction in an animal in need of such treatment. The method comprises the step of administering to the animal a therapeutically effective amount of a compound of Formula I or a pharmaceutical composition thereof. Preferably, the animal is a mammal; more preferably a human being.

Still another object of the invention is the use of a compound according to Formula I, or a pharmaceutically acceptable salt or solvate thereof, for the manufacture of a medicament for the treatment of any of the conditions discussed herein.

Another object of the invention provides a compound of Formula I, or a pharmaceutically acceptable salt or solvate thereof, for use in therapy.

The invention additionally provides processes for the preparation of compounds of Formula I. General and specific processes are discussed in more detail below.

DETAILED DESCRIPTION OF THE EMBODIMENTS

The present invention is based upon the discovery of compounds contemplated to be useful as pharmaceuticals, in particular as modulators of metabotropic glutamate receptors. More particularly, compounds of the present invention exhibit activity as potentiators of the mGluR2 receptor, and are contemplated to be useful in therapy, in particular for the treatment of neurological and psychiatric disorders associated with glutamate dysfunction.

Definitions

Unless specified otherwise within this specification, the nomenclature used in this specification generally follows the examples and rules stated in *Nomenclature of Organic Chemistry*, Sections A, B, C, D, E, F, and H, Pergamon Press, Oxford, 1979, which is incorporated by references herein for its exemplary chemical structure names and rules on naming chemical structures. Optionally, a name of a compound may be generated using a chemical naming program: ACD/ChemSketch, Version 5.09/September 2001, Advanced Chemistry Development, Inc., Toronto, Canada.

The term "alkyl" as used herein means a straight- or branched-chain hydrocarbon radical having from one to six carbon atoms, and includes methyl, ethyl, propyl, isopropyl, t-butyl and the like.

The term "alkenyl" as used herein means a straight- or branched-chain alkenyl radical having from two to six carbon atoms, and includes ethenyl, 1-propenyl, 1-butenyl and the like.

The term "alkynyl" as used herein means a straight- or branched-chain alkynyl radical having from two to six carbon atoms, and includes 1-propynyl (propargyl), 1-butynyl and the like.

The term "cycloalkyl" as used herein means a cyclic group (which may be unsaturated) having from three to seven carbon atoms, and includes cyclopropyl, cyclohexyl, cyclohexenyl and the like.

The term "heterocycloalkyl" as used herein means a three- to seven-membered cyclic group (which may be unsaturated) having at least one heteroatom selected from the group consisting of N, S and O, and includes piperidinyl, piperazinyl, pyrrolidinyl, tetrahydrofuranyl and the like.

The term "alkoxy" as used herein means a straight- or branched-chain alkoxy radical having from one to six carbon atoms and includes methoxy, ethoxy, propyloxy, isopropyloxy, t-butoxy and the like.

The term "halo" as used herein means halogen and includes fluoro, chloro, bromo, iodo and the like, in both radioactive and non-radioactive forms.

The term "alkylene" as used herein means a difunctional branched or unbranched saturated hydrocarbon radical having one to six carbon atoms, and includes methylene, ethylene, n-propylene, n-butylene and the like.

The term "alkenylene" as used herein means a difunctional branched or unbranched hydrocarbon radical having two to six carbon atoms and having at least one double bond, and includes ethenylene, n-propenylene, n-butenylene and the like.

The term "alkynylene" as used herein means a difunctional branched or unbranched hydrocarbon radical having two to six carbon atoms and having at least one triple bond, and includes ethynylene, n-propynylene, n-butynylene and the like.

The term "aryl" as used herein means an aromatic group having five to twelve atoms, and includes phenyl, naphthyl and the like.

The term "heteroaryl" means an aromatic group which includes at least one heteroatom selected from the group consisting of N, S and O, and includes groups and includes pyridyl, indolyl, furyl, benzofuryl, thienyl, benzothienyl, quinolyl, oxazolyl and the like.

The term "pharmaceutically acceptable salt" means either an acidic addition salt or a basic addition salt which is compatible with the treatment of patients.

A "pharmaceutically acceptable acidic addition salt" is any non-toxic organic or inorganic acidic addition salt of the base compounds represented by Formula I or any of its intermediates. Illustrative inorganic acids which form suitable salts include hydrochloric, hydrobromic, sulfuric and phosphoric acid and acid metal salts such as sodium monohydrogen orthophosphate and potassium hydrogen sulfate. Illustrative organic acids which form suitable salts include the mono-, di- and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic, p-toluenesulfonic acid and other sulfonic acids such as methanesulfonic acid and 2-hydroxyethanesulfonic acid. Either the mono- or di-acid salts can be formed, and such salts can exist in either a hydrated, solvated or substantially anhydrous form. In general, the acidic addition salts of these compounds are more soluble in water and various hydrophilic organic solvents, and generally demonstrate higher melting points in comparison to their free base forms. The selection criteria for the appropriate salt will be known to one skilled in the art. Other non-pharmaceutically acceptable salts e.g. oxalates may be used for example in the isolation of compounds of Formula I for laboratory use, or for subsequent conversion to a pharmaceutically acceptable acidic addition salt.

A "pharmaceutically acceptable basic addition salt" is any non-toxic organic or inorganic base addition salt of the acid compounds represented by Formula I or any of its intermediates. Illustrative inorganic bases which form suitable salts include lithium, sodium, potassium, calcium, magnesium or barium hydroxides. Illustrative organic bases which form suitable salts include aliphatic, alicyclic or aromatic organic amines such as methylamine, trimethyl amine and picoline or ammonia. The selection of the appropriate salt may be important so that an ester functionality, if any, elsewhere in the molecule is not hydrolyzed. The selection criteria for the appropriate salt will be known to one skilled in the art.

The term "solvate" means a compound of Formula I or the pharmaceutically acceptable salt of a compound of Formula I wherein molecules of a suitable solvent are incorporated into a crystal lattice. A suitable solvent is physiologically tolerable at the dosage administered as the solvate. Examples of suitable solvents are ethanol, water and the like. When water is the solvent, the molecule is referred to as a hydrate.

The term "treat" or "treating" means to alleviate symptoms, eliminate the causation of the symptoms either on a temporary or permanent basis, or to prevent or slow the appearance of symptoms of the named disorder or condition.

The term "therapeutically effective amount" means an amount of the compound which is effective in treating the named disorder or condition.

The term "pharmaceutically acceptable carrier" means a non-toxic solvent, dispersant, excipient, adjuvant or other material which is mixed with the active ingredient in order to permit the formation of a pharmaceutical composition, i.e., a dosage form capable of administration to the patient. One example of such a carrier is a pharmaceutically acceptable oil typically used for parenteral administration.

Compounds

Compounds of the invention conform generally to Formula I:

Formula I

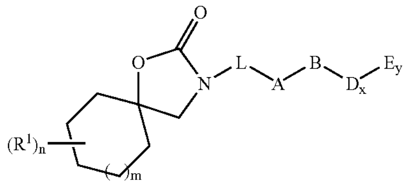

wherein:

$R^1$ is selected from the group consisting of H, hydroxy, F, Cl, Br, I, nitro, CN, alkyl, alkylhalo, O-alkyl, O-alkylhalo, alkenyl, O-alkenyl, alkynyl, O-alkynyl, methylenedioxy and ethylenedioxy;

L is selected from the group consisting of alkylene, alkenylene and alkynylene wherein any hydrogen atom of L may be independently substituted with one or more substituents selected from the group consisting of hydroxy, F, Cl, Br, I, alkyl, alkylhalo and O-alkyl;

A is selected from the group consisting of aryl and heteroaryl;

B is selected from the group consisting of alkylene, aryl, heteroaryl, cycloalkyl and heterocycloalkyl;

D is selected from the group consisting of alkylene, O,O-alkylene and alkylene-O;

E is selected from the group consisting of aryl, heteroaryl, cycloalkyl and heterocycloalkyl;

m and n are independently selected from the group consisting of 0, 1, 2, 3 and 4;

x and y are independently selected from the group consisting of 0 and 1;

wherein any of A, B and E may be substituted with up to 4 substituents independently selected from the group consisting of hydroxy, F, Cl, Br, I, nitro, CN, alkyl, alkylhalo, O-alkyl, O-alkylhalo, alkenyl, O-alkenyl, alkynyl, O-alkynyl, alkyleneO$R^2$, O-alkyleneO$R^2$, (CO)$R^2$, O(CO)$R^2$, alkyleneO(CO)$R^2$, alkylene(CO)$R^2$, O-alkylene(CO)$R^2$, $CO_2R$, alkylene$CO_2R^2$, O-alkylene$CO_2R^2$, alkylenecyano, O-alkylenecyano, O(CN)O$R^2$, $NR^2R^3$, alkylene$NR^2R^3$, O-alkylene$NR^2R^3$, (CO)$NR^2R^3$, alkylene(CO)$NR^2R^3$, O—(CO)$NR^2R^3$, O-alkylene(CO)$NR^2R^3$, $NR^2$(CO)$R^3$, alkylene$NR^2$(CO)$R^3$, O-alkylene$NR^2$(CO)$R^3$, $NR^2$(CO)$NR^3R^4$, alkylene$NR^2$(CO)$NR^3R^4$, and wherein $R^2$ and $R^4$ are independently selected from the group consisting of H and alkyl, and $R^3$ is selected from the group consisting of H, alkyl and alkylene-$NR^2R^4$.

In a particular embodiment, compounds are those in accord with Formula I wherein m is 1, of Formula Ia:

Formula Ia

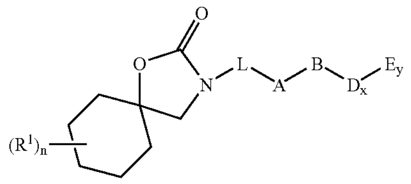

wherein $R^1$, n, L, A, B, D, E, x and y are as defined for Formula I.

In another particular embodiment, compounds are those in accord with Formula I wherein m is 1, and x and y are each 0, of Formula Ib:

Formula Ib

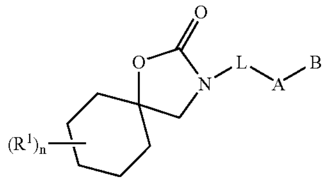

wherein $R^1$, n, L, A and B are as defined for Formula I.

In yet another particular embodiment, compounds are those in accord with Formula I wherein m is 1, x and y are each 0, A and B are both aryl wherein aryl is phenyl, of Formula Ic:

Formula Ic

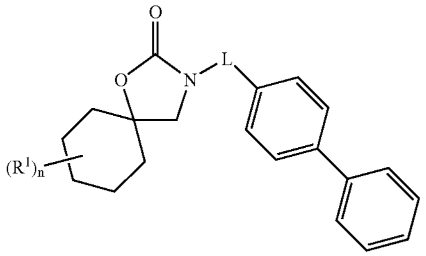

wherein $R^1$, n and L are as defined for Formula I, wherein each phenyl may be substituted with up to 4 substituents independently selected from the group consisting of hydroxy, F, Cl, Br, I, nitro, CN, alkyl, alkylhalo, O-alkyl, O-alkylhalo, alkenyl, O-alkenyl, alkynyl, O-alkynyl, alkyleneO$R^2$, O-alkyleneO$R^2$, (CO)$R^2$, O(CO)$R^2$, alkyleneO(CO)$R^2$, alkylene(CO)$R^2$, O-alkylene(CO)$R^2$, $CO_2R$, alkylene$CO_2R^2$, O-alkylene$CO_2R^2$, alkylenecyano, O-alkylenecyano, $O(CN)OR^2$, $NR^2R^3$, alkylene$NR^2R^3$, O-alkylene$NR^2R^3$, $(CO)NR^2R^3$, alkylene$(CO)NR^2R^3$, O—$(CO)NR^2R^3$, O-alkylene$(CO)NR^2R^3$, $NR^2(CO)R^3$, alkylene$NR^2(CO)R^3$, O-alkylene$NR^2(CO)R^3$, $NR^2(CO)NR^3R^4$, alkylene$NR^2(CO)NR^3R^4$, and wherein $R^2$ and $R^4$ are independently selected from the group consisting of H and alkyl, and $R^3$ is selected from the group consisting of H, alkyl and alkylene-$NR^2R^4$.

In compounds of a further embodiment of the invention L is an alkylene group.

In compounds of a further embodiment of the invention A is an aryl group.

In compounds of a another embodiment A is a heteroaryl group.

In compounds of a another embodiment of the invention B is an aryl group.

In compounds of a another embodiment of the invention D is an alkylene group.

In compounds of a another embodiment of the invention E is a heterocycloalkyl group.

It will be understood by those of skill in the art that when compounds of the present invention have one or more chiral centers, the compounds of the invention may exist in, and be isolated as, enantiomeric or diastereomeric forms, or as a racemic mixture. The present invention includes any possible enantiomers, diastereomers, racemates or mixtures thereof, of a compound of Formula I. The optically active forms of the compound of the invention may be prepared, for example, by chiral chromatographic separation of a racemate, by synthesis from optically active starting materials or by asymmetric synthesis based on the procedures described thereafter.

It will also be appreciated by those of skill in the art that certain compounds of the present invention may exist as geometrical isomers, for example E and Z isomers of alkenes. The present invention includes any geometrical isomer of a compound of Formula I. It will further be understood that the present invention encompasses tautomers of the compounds of Formula I.

It will also be understood by those of skill in the art that certain compounds of the present invention may exist in solvated, for example hydrated, as well as unsolvated forms. It will further be understood that the present invention encompasses all such solvated forms of the compounds of Formula I.

Within the scope of the invention are also salts of the compounds of Formula I. Generally, pharmaceutically acceptable salts of compounds of the present invention are obtained using standard procedures well known in the art, for example, by reacting a sufficiently basic compound, for example an alkyl amine with a suitable acid, for example, HCl or acetic acid, to afford a physiologically acceptable anion. It is also possible to make a corresponding alkali metal (such as sodium, potassium, or lithium) or an alkaline earth metal (such as a calcium) salt by treating a compound of the present invention having a suitably acidic proton, such as a carboxylic acid or a phenol with one equivalent of an alkali metal or alkaline earth metal hydroxide or alkoxide (such as the ethoxide or methoxide), or a suitably basic organic amine (such as choline or meglumine) in an aqueous medium, followed by conventional purification techniques.

In one embodiment of the present invention, the compound of Formula I may be converted to a pharmaceutically acceptable salt or solvate thereof, particularly, an acidic addition salt such as a hydrochloride, hydrobromide, phosphate, acetate, fumarate, maleate, tartrate, citrate, methanesulphonate or p-toluenesulphonate.

Specific examples of the present invention include the compounds 1 to 18.1, illustrated in the following table, their pharmaceutically acceptable salts, hydrates, solvates, optical isomers, and combinations thereof:

| Example No. | Structure | Name |
| --- | --- | --- |
| 1.1 | 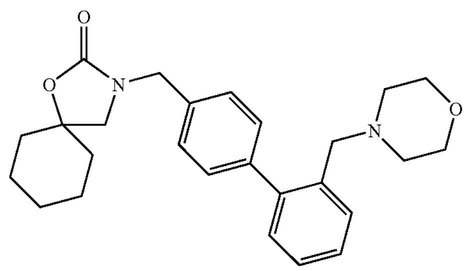 | 3-(2'-Morpholin-4-ylmethyl-biphenyl-4-ylmethyl)-1-oxa-3-aza-spiro[4.5]decan-2-one |
| 1.2 | 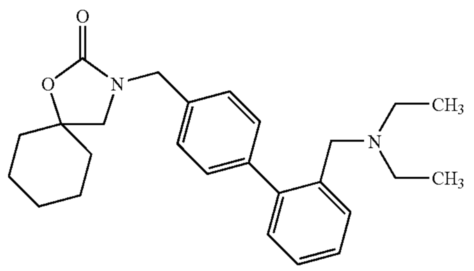 | 3-(2'-Diethylaminomethyl-biphenyl-4-ylmethyl)-1-oxa-3-aza-spiro[4.5]decan-2-one |

-continued
| Example No. | Structure | Name |
| --- | --- | --- |
| 1.3 | 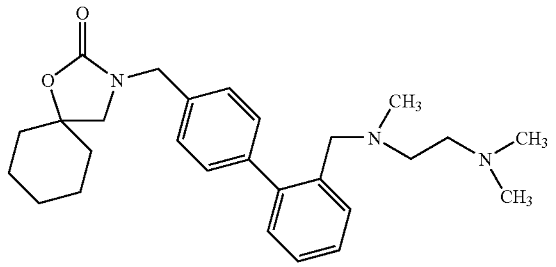 | 3-(2'-{[(2-Dimethylamino-ethyl)-methyl-amino]-methyl}-biphenyl-4-ylmethyl)-1-oxa-3-aza-spiro[4.5]decan-2-one |
| 1.4 | 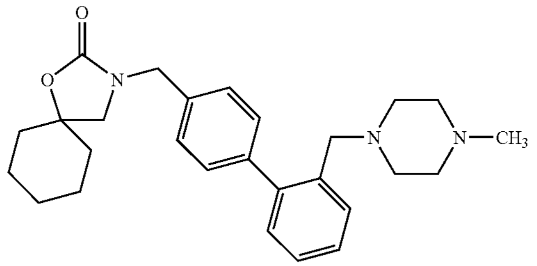 | 3-[2'-(4-Methyl-piperazin-1-ylmethyl)-biphenyl-4-ylmethyl]-1-oxa-3-aza-spiro[4.5]decan-2-one |
| 1.5 | 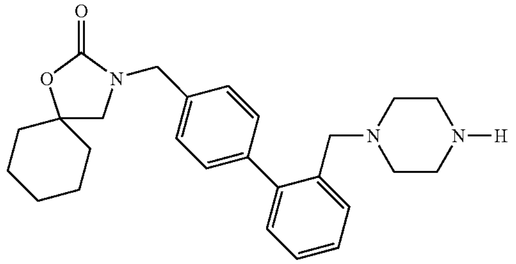 | 3-(2'-Piperazin-1-ylmethyl-biphenyl-4-ylmethyl)-1-oxa-3-aza-spiro[4.5]decan-2-one |
| 1.6 | 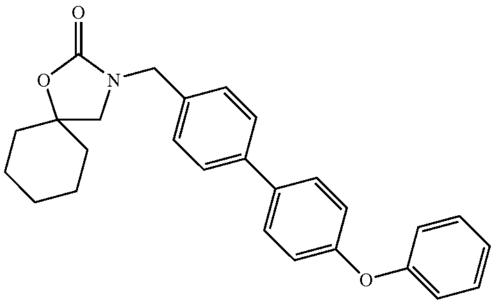 | 3-(4'-Phenoxy-biphenyl-4-ylmethyl)-1-oxa-3-aza-spiro[4.5]decan-2-one |
| 1.7 | 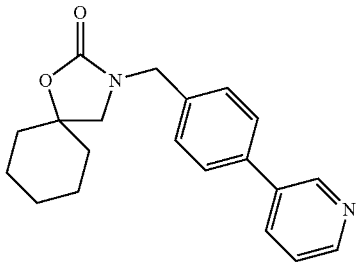 | 3-(4-Pyridin-3-yl-benzyl)-1-oxa-3-aza-spiro[4.5]decan-2-one |

-continued
| Example No. | Structure | Name |
|---|---|---|
| 1.8 | 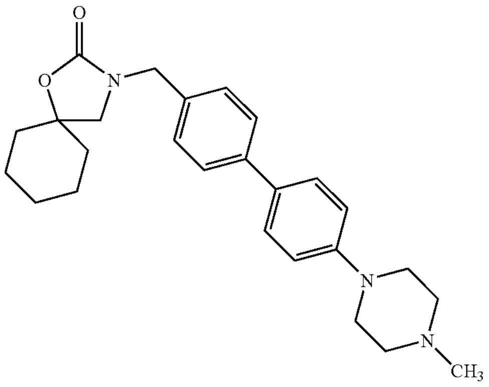 | 3-[4'-(4-Methyl-piperazin-1-yl)-biphenyl-4-ylmethyl]-1-oxa-3-aza-spiro[4.5]decan-2-one |
| 1.9 | 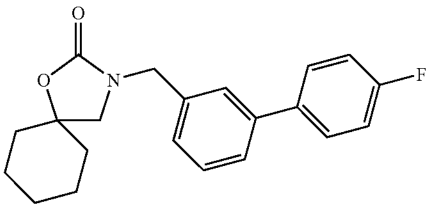 | 3-(4'-Fluoro-biphenyl-3-ylmethyl)-1-oxa-3-aza-spiro[4.5]decan-2-one |
| 1.10 | 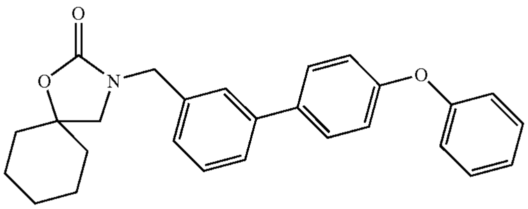 | 3-(4'-Phenoxy-biphenyl-3-ylmethyl)-1-oxa-3-aza-spiro[4.5]decan-2-one |
| 1.11 | 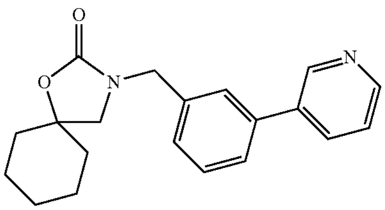 | 3-(3-Pyridin-3-yl-benzyl)-1-oxa-3-aza-spiro[4.5]decan-2-one |
| 1.12 | 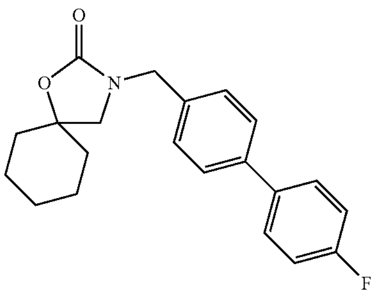 | 3-(4'-Fluoro-biphenyl-4-ylmethyl)-1-oxa-3-aza-spiro[4.5]decan-2-one |

-continued
| Example No. | Structure | Name |
|---|---|---|
| 1.13 | 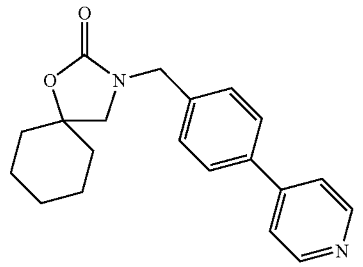 | 3-(4-Pyridin-4-yl-benzyl)-1-oxa-3-aza-spiro[4.5]decan-2-one |
| 1.14 | 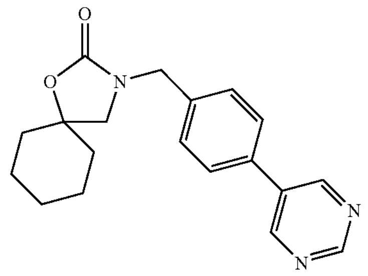 | 3-(4-Pyrimidin-5-yl-benzyl)-1-oxa-3-aza-spiro[4.5]decan-2-one |
| 1.15 | 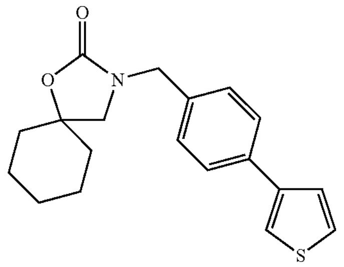 | 3-(4-Thiophen-3-yl-benzyl)-1-oxa-3-aza-spiro[4.5]decan-2-one |
| 1.16 | 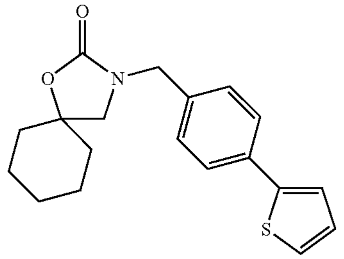 | 3-(4-Thiophen-2-yl-benzyl)-1-oxa-3-aza-spiro[4.5]decan-2-one |
| 1.17 | 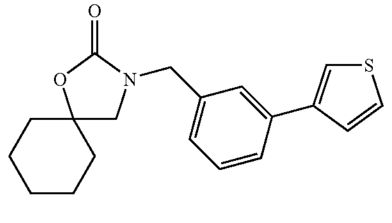 | 3-(3-Thiophen-3-yl-benzyl)-1-oxa-3-aza-spiro[4.5]decan-2-one |

-continued

| Example No. | Structure | Name |
|---|---|---|
| 1.18 | 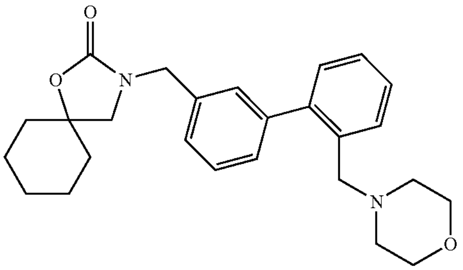 | 3-(3-Thiazol-2-yl-benzyl)-1-oxa-3-aza-spiro[4.5]decan-2-one |
| 1.19 | 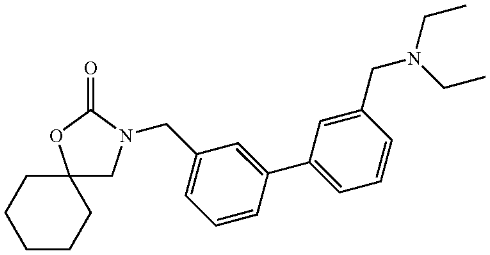 | 3-(3'-Diethylaminomethyl-biphenyl-3-yl methyl)-1-oxa-3-aza-spiro[4.5]decan-2-one |
| 1.20 | 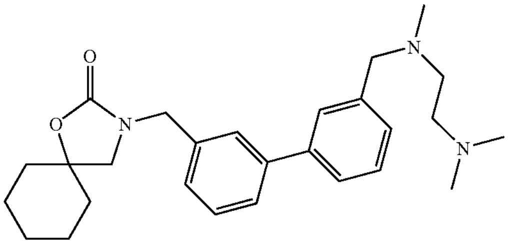 | 3-(3'-{[(2-Dimethylamino-ethyl)-methyl-amino]-methyl}-biphenyl-3-ylmethyl)-1-oxa-3-aza-spiro[4.5]decan-2-one |
| 1.21 | 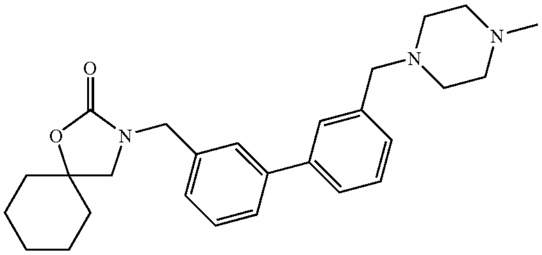 | 3-[3'-(4-Methyl-piperazin-1-ylmethyl)-biphenyl-3-ylmethyl]-1-oxa-3-aza-spiro[4.5]decan-2-one |
| 1.22 | 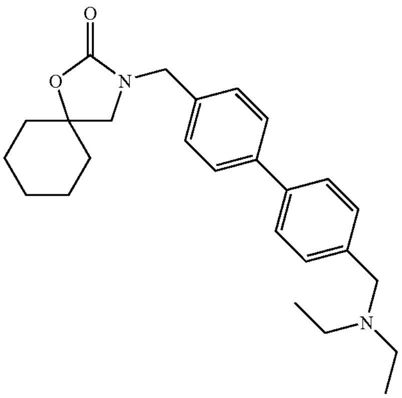 | 3-(4'-Diethylamino methyl-biphenyl-4-ylmethyl)-1-oxa-3-aza-spiro[4.5]decan-2-one |

-continued
| Example No. | Structure | Name |
|---|---|---|
| 1.23 | 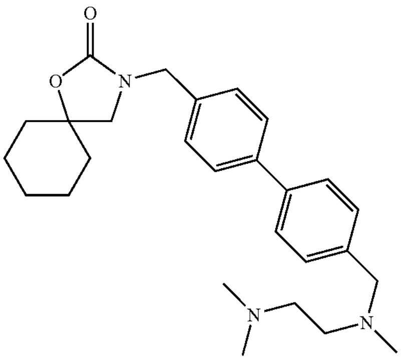 | 3-(4'-{[(2-Dimethylamino-ethyl)-methyl-amino]-methyl}-biphenyl-4-ylmethyl)-1-oxa-3-aza-spiro[4.5]decan-2-one |
| 1.24 | 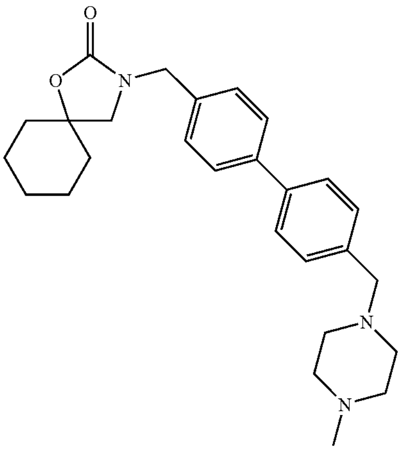 | 3-[4'-(4-Methyl-piperazin-1-ylmethyl)-biphenyl-4-ylmethyl]-1-oxa-3-aza-spiro[4.5]decan-2-one |
| 1.25 | 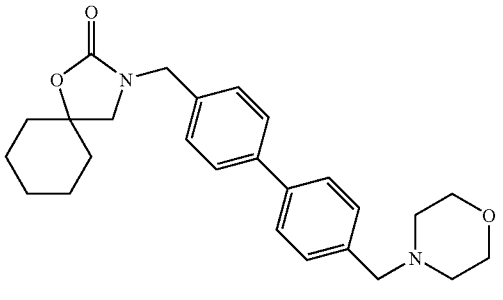 | 3-(4'-Morpholin-4-ylmethyl-biphenyl-4-ylmethyl)-1-oxa-3-aza-spiro[4.5]decan-2-one |
| 1.26 | 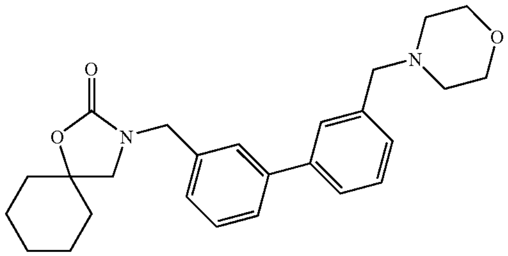 | 3-(3'-Morpholin-4-ylmethyl-biphenyl-3-ylmethyl)-1-oxa-3-aza-spiro[4.5]decan-2-one |

-continued

| Example No. | Structure | Name |
|---|---|---|
| 1.27 | 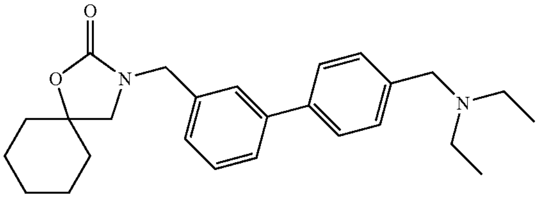 | 3-(4'-Diethylaminomethyl-biphenyl-3-ylmethyl)-1-oxa-3-aza-spiro [4.5]decan-2-one |
| 1.28 | 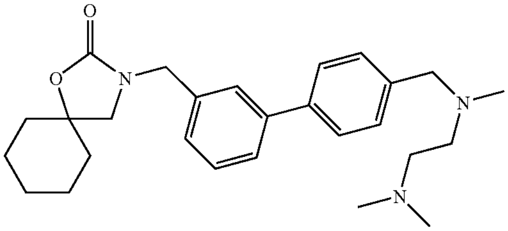 | 3-(4'-{[(2-Dimethylamino-ethyl)-methyl-amino]-methyl}-biphenyl-3-ylmethyl)-1-oxa-3-aza-spiro [4.5]decan-2-one |
| 1.28 | 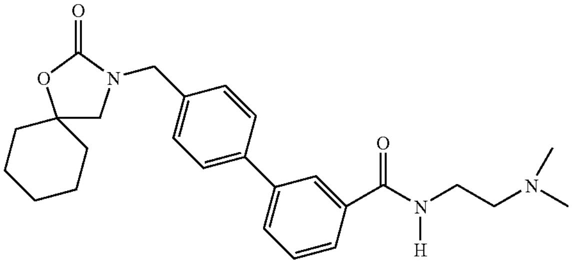 | 4'-(2-Oxo-1-oxa-3-aza-spiro[4.5]dec-3-ylmethyl)-biphenyl-3-carboxylic acid (2-dimethyl amino-ethyl)-amide |
| 1.30 | 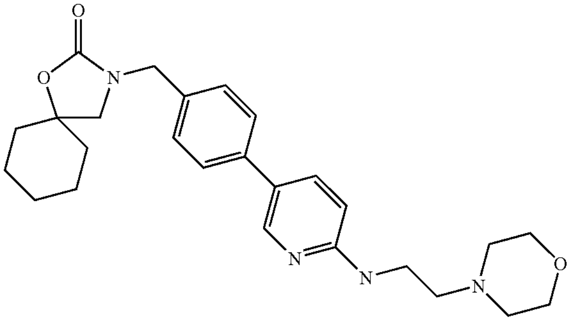 | 3-{4-[6-(2-Morpholin-4-yl-ethylamino)-pyridin-3-yl]-benzyl}-1-oxa-3-aza-spiro[4.5] decan-2-one |
| 1.31 | 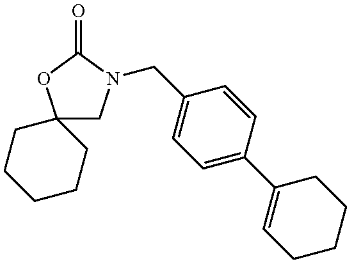 | 3-(4-Cyclohex-1-enyl-benzyl)-1-oxa-3-aza-spiro[4.5]decan-2-one |
| 1.32 | 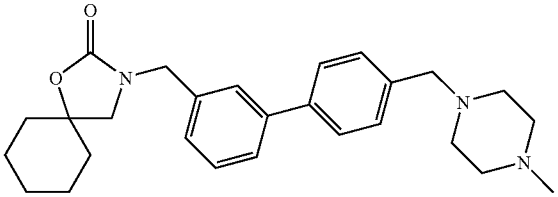 | 3-[4'-(4-Methyl-piperazin-1-ylmethyl)-biphenyl-3-ylmethyl]-1-oxa-3-aza-spiro[4.5]decan-2-one |

-continued

| Example No. | Structure | Name |
| --- | --- | --- |
| 1.33 | 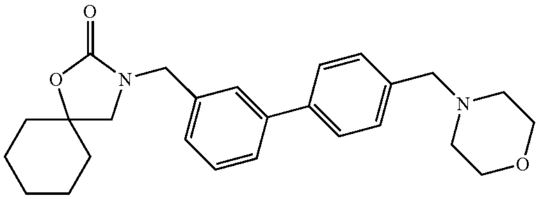 | 3-(4'-Morpholin-4-ylmethyl-biphenyl-3-ylmethyl)-1-oxa-3-aza-spiro[4.5]decan-2-one |
| 1.34 | 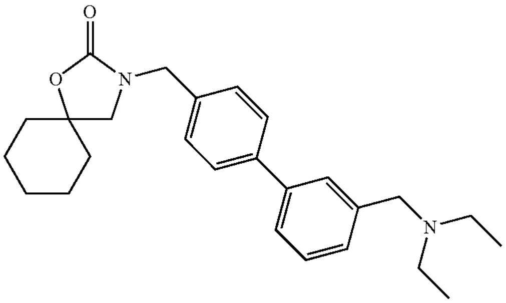 | 3-(3'-Diethylamino methyl-biphenyl-4-ylmethyl)-1-oxa-3-aza-spiro[4.5]decan-2-one |
| 1.35 | 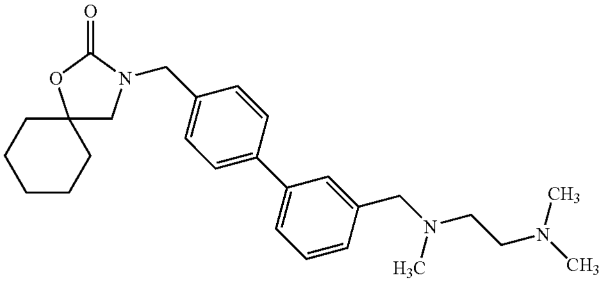 | 3-(3'-{[(2-Dimethyl amino-ethyl)-methyl-amino]-methyl}-biphenyl-4-ylmethyl)-1-oxa-3-aza-spiro [4.5]decan-2-one |
| 1.36 | 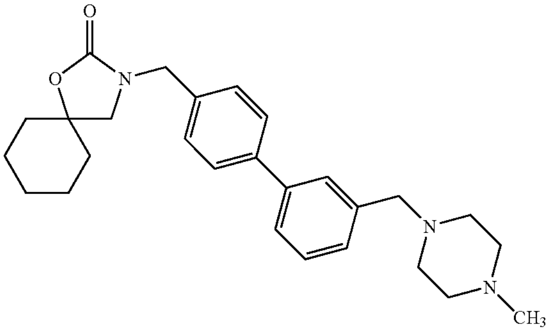 | 3-[3'-(4-Methyl-piperazin-1-ylmethyl)-biphenyl-4-ylmethyl]-1-oxa-3-aza-spiro [4.5]decan-2-one |
| 1.37 | 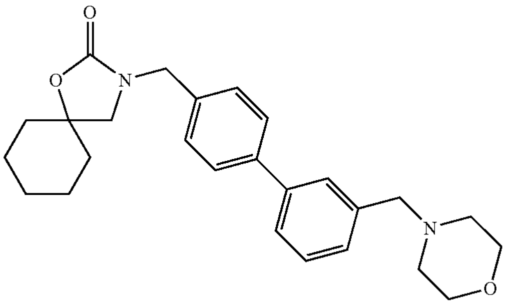 | 3-(3'-Morpholin-4-ylmethyl-biphenyl-4-ylmethyl)-1-oxa-3-aza-spiro[4.5]decan-2-one |

-continued
| Example No. | Structure | Name |
|---|---|---|
| 1.38 | 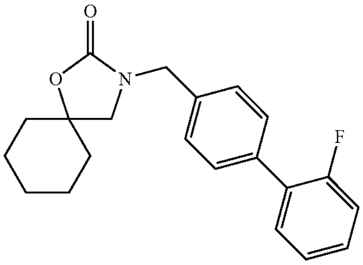 | 3-(2'-Fluoro-biphenyl-4-ylmethyl)-1-oxa-3-aza-spiro[4.5]decan-2-one |
| 1.39 | 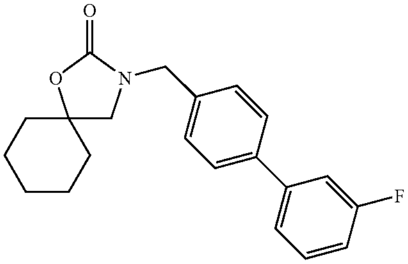 | 3-(3'-Fluoro-biphenyl-4-ylmethyl)-1-oxa-3-aza-spiro[4.5]decan-2-one |
| 1.40 | 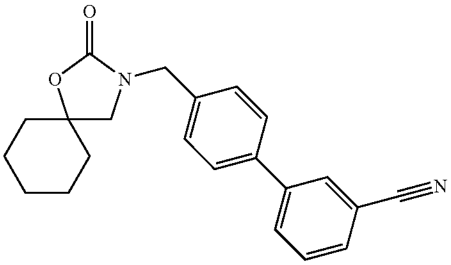 | 4'-(2-Oxo-1-oxa-3-aza-spiro[4.5]dec-3-yl methyl)-biphenyl-3-carbonitrile |
| 1.41 | 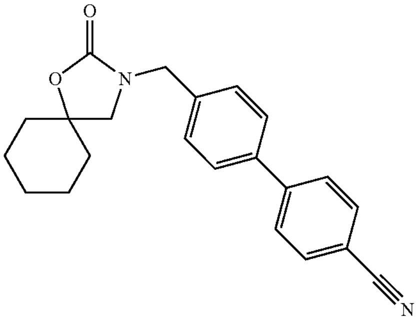 | 4'-(2-Oxo-1-oxa-3-aza-spiro[4.5]dec-3-ylmethyl)-biphenyl-4-carbonitrile |
| 1.42 | 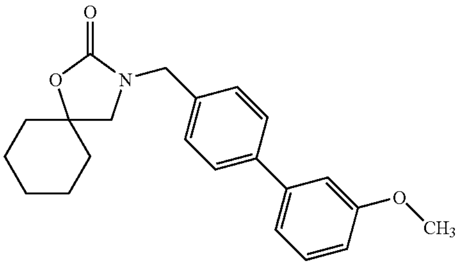 | 3-(3'-Methoxy-biphenyl-4-ylmethyl)-1-oxa-3-aza-spiro[4.5]decan-2-one |

-continued
| Example No. | Structure | Name |
|---|---|---|
| 1.43 | 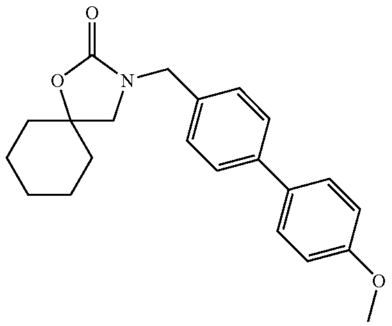 | 3-(4'-Methoxy-biphenyl-4-ylmethyl)-1-oxa-3-aza-spiro[4.5]decan-2-one |
| 1.44 | 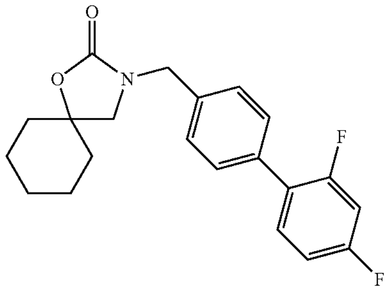 | 3-(2',4'-Difluoro-biphenyl-4-ylmethyl)-1-oxa-3-aza-spiro[4.5]decan-2-one |
| 1.45 | 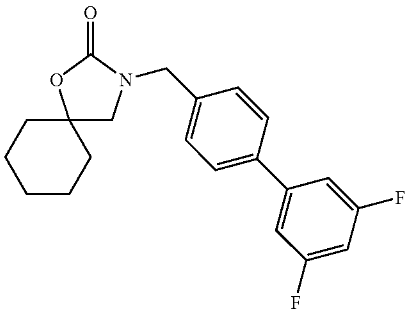 | 3-(3',5'-Difluoro-biphenyl-4-ylmethyl)-1-oxa-3-aza-spiro[4.5]decan-2-one |
| 1.46 | 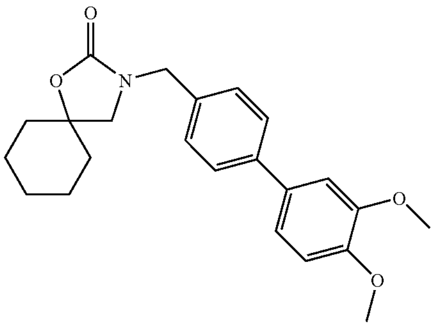 | 3-(3',4'-Dimethoxy-biphenyl-4-ylmethyl)-1-oxa-3-aza-spiro[4.5]decan-2-one |

-continued
| Example No. | Structure | Name |
|---|---|---|
| 1.47 | 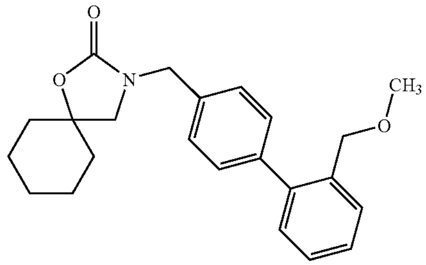 | 3-(2'-Methoxymethyl-biphenyl-4-ylmethyl)-1-oxa-3-aza-spiro [4.5]decan-2-one |
| 1.48 | 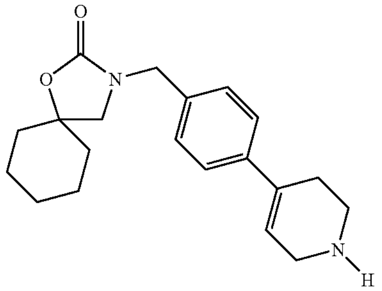 | 3-[4-(1,2,3,6-Tetrahydro-pyridin-4-yl)-benzyl]-1-oxa-3-aza-spiro [4.5]decan-2-one |
| 1.49 | 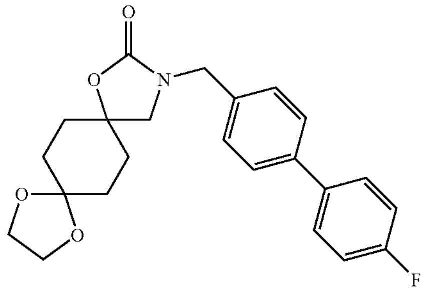 | 3-(4'-Fluoro-biphenyl-4-ylmethyl)-1,9,12-trioxa-3-aza-dispiro[4.2.4.2]tetradecan-2-one |
| 1.50 | 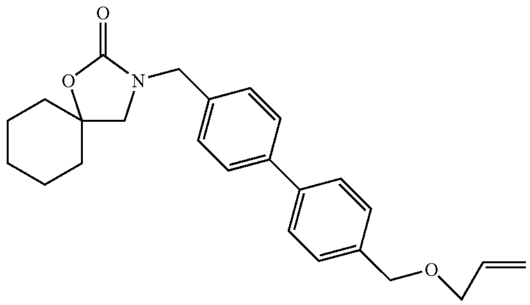 | 3-(4'-Allyloxymethyl-biphenyl-4-ylmethyl)-1-oxa-3-aza-spiro[4.5]decan-2-one |
| 1.51 | 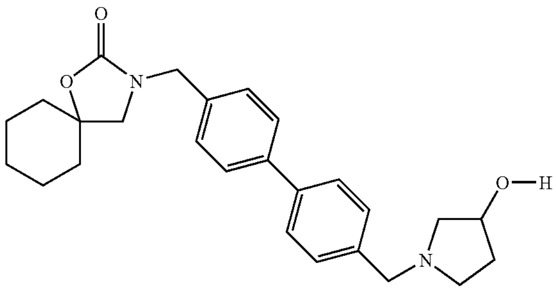 | 3-[4'-(3-Hydroxy-pyrrolidin-1-ylmethyl)-biphenyl-4-ylmethyl]-1-oxa-3-aza-spiro[4.5]decan-2-one |

-continued
| Example No. | Structure | Name |
|---|---|---|
| 1.52 | 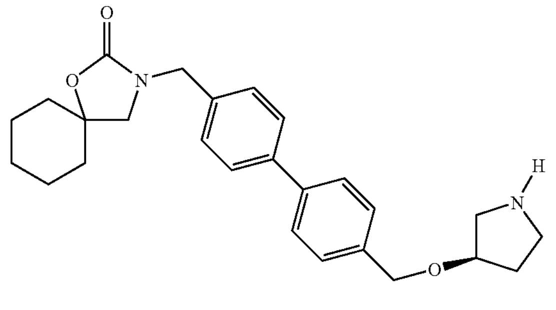 | 3-[4'-(Pyrrolidin-3-yloxymethyl)-biphenyl-4-ylmethyl]-1-oxa-3-aza-spiro[4.5]decan-2-one |
| 1.53 | 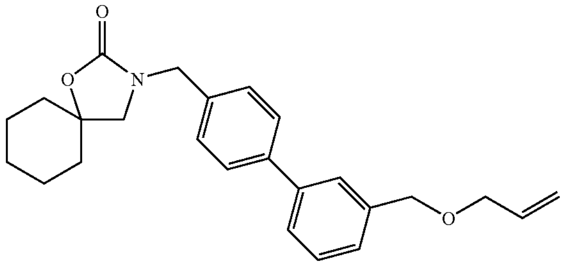 | 3-(3'-Allyloxymethyl-biphenyl-4-ylmethyl)-1-oxa-3-aza-spiro[4.5]decan-2-one |
| 1.54 | 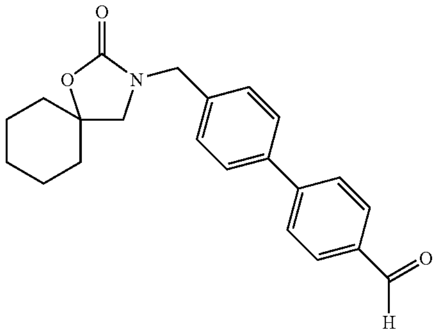 | 4'-(2-Oxo-1-oxa-3-aza-spiro[4.5]dec-3-ylmethyl)-biphenyl-4-carbaldehyde |
| 1.55 | 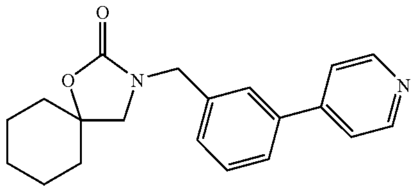 | 3-(3-Pyridin-4-yl-benzyl)-1-oxa-3-aza-spiro[4.5]decan-2-one |
| 1.56 | 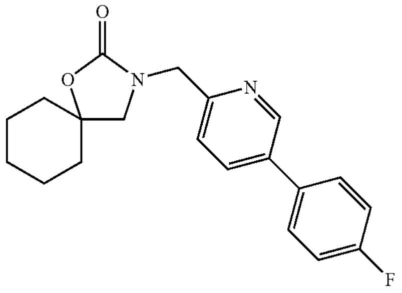 | 3-[5-(4-Fluoro-phenyl)-pyridin-2-ylmethyl]-1-oxa-3-aza-spiro[4.5]decan-2-one |

-continued
| Example No. | Structure | Name |
|---|---|---|
| 1.57 | 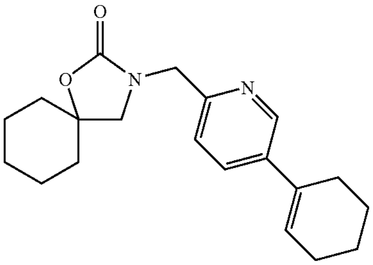 | 3-(5-Cyclohex-1-enyl-pyridin-2-ylmethyl)-1-oxa-3-aza-spiro[4.5]decan-2-one |
| 3.2 | 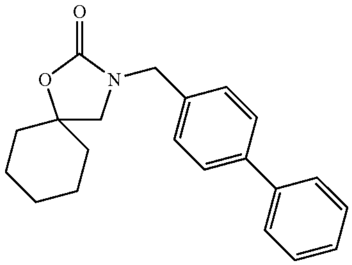 | 3-Biphenyl-4-ylmethyl-1-oxa-3-aza-spiro[4.5]decan-2-one |
| 3.3 | 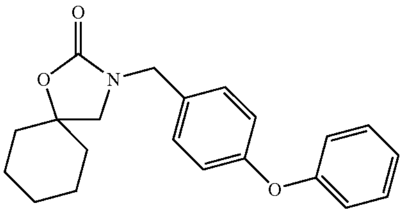 | 3-(4-Phenoxy-benzyl)-1-oxa-3-aza-spiro[4.5]decan-2-one |
| 3.6 | 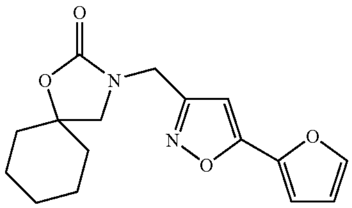 | 3-(5-Furan-2-yl-isoxazol-3-ylmethyl)-1-oxa-3-aza-spiro[4.5]decan-2-one |
| 3.7 | 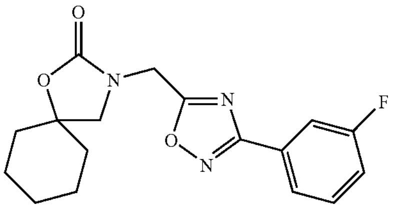 | 3-[3-(3-Fluoro-phenyl)-[1.2.4]oxadiazol-5-ylmethyl]-1-oxa-3-aza-spiro[4.5]decan-2-one |
| 4.1 | 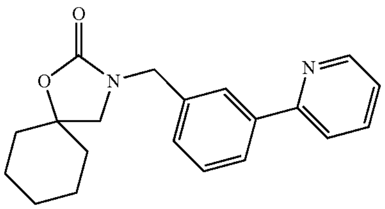 | 3-(3-Pyridin-2-yl-benzyl)-1-oxa-3-aza-spiro[4.5]decan-2-one |

-continued
| Example No. | Structure | Name |
|---|---|---|
| 4.2 | 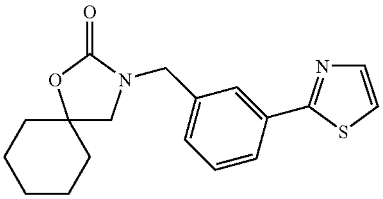 | 3-(3-Thiazol-2-yl-benzyl)-1-oxa-3-aza-spiro[4.5]decan-2-one |
| 4.3 | 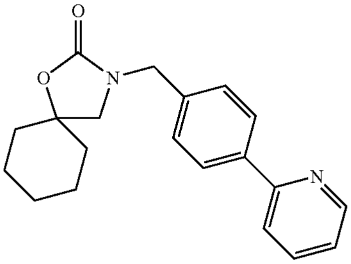 | 3-(4-Pyridin-2-yl-benzyl)-1-oxa-3-aza-spiro[4.5]decan-2-one |
| 4.4 | 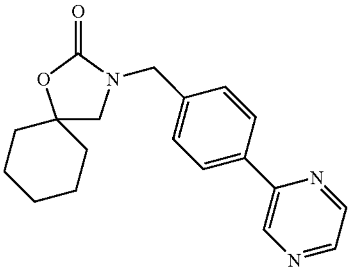 | 3-(4-Pyrazin-2-yl-benzyl)-1-oxa-3-aza-spiro[4.5]decan-2-one |
| 4.5 | 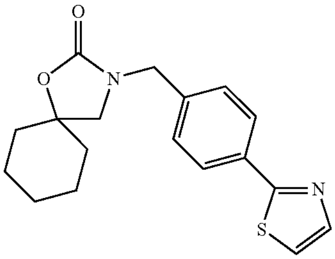 | 3-(4-Thiazol-2-yl-benzyl)-1-oxa-3-aza-spiro[4.5]decan-2-one |
| 5.1 | 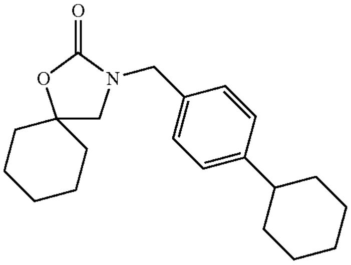 | 3-(4-Cyclohexyl-benzyl)-1-oxa-3-aza-spiro[4.5]decan-2-one |

-continued
| Example No. | Structure | Name |
|---|---|---|
| 7.1 | 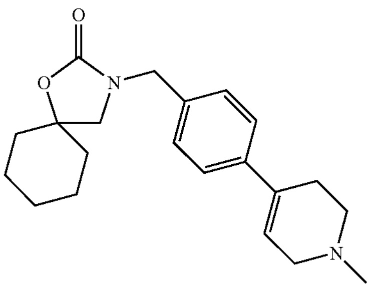 | 3-[4-(1-Methyl-1,2,3,6-tetrahydro-pyridin-4-yl)-benzyl]-1-oxa-3-aza-spiro[4.5]decan-2-one |
| 7.2 | 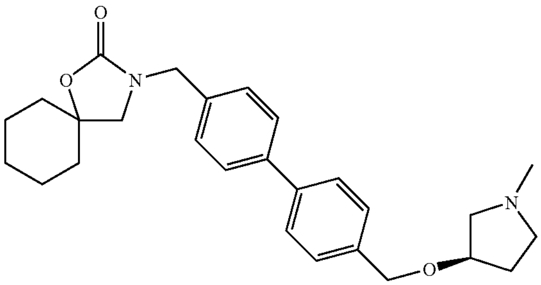 | 3-[4'-(1-Methyl-pyrrolidin-3-yloxymethyl)-biphenyl-4-ylmethyl]-1-oxa-3-aza-spiro[4.5]decan-2-one |
| 8.1 | 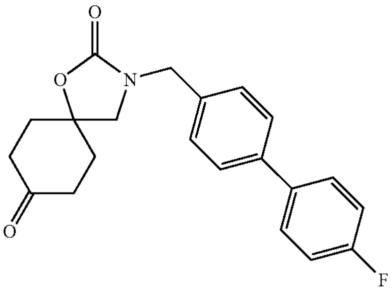 | 3-(4'-Fluoro-biphenyl-4-ylmethyl)-1-oxa-3-aza-spiro[4.5]decane-2,8-dione |
| 9.1 | 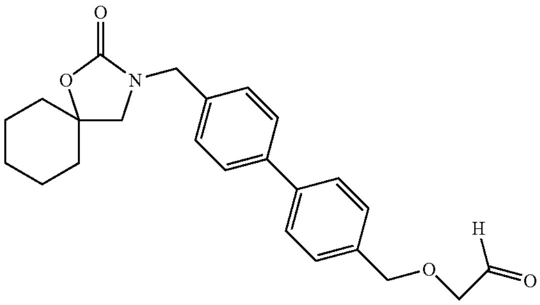 | [4'-(2-Oxo-1-oxa-3-aza-spiro[4.5]dec-3-ylmethyl)-biphenyl-4-yl methoxy]-acetaldehyde |
| 10.1 | 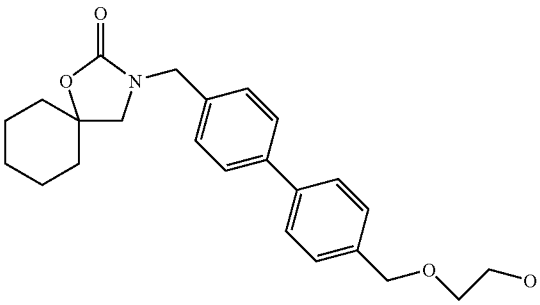 | 3-[4'-(2-Hydroxy-ethoxymethyl)-biphenyl-4-ylmethyl]-1-oxa-3-aza-spiro[4.5]decan-2-one |

-continued

| Example No. | Structure | Name |
|---|---|---|
| 11.1 | 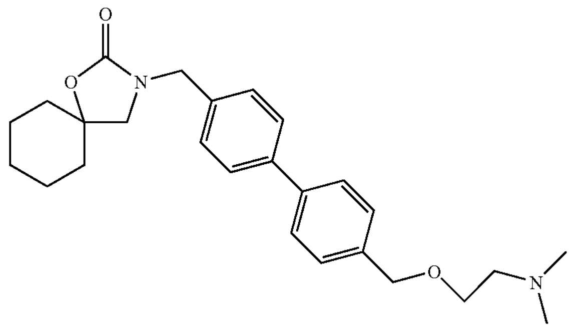 | 3-[4'-(2-Dimethylamino-ethoxymethyl)-biphenyl-4-ylmethyl]-1-oxa-3-aza-spiro[4.5]decan-2-one |
| 11.2 | 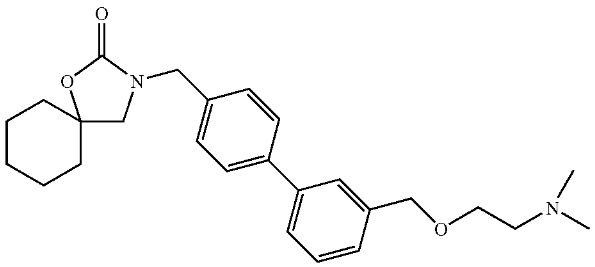 | 3-[3'-(2-Dimethylamino-ethoxymethyl)-biphenyl-4-ylmethyl]-1-oxa-3-aza-spiro[4.5]decan-2-one |
| 11.3 | 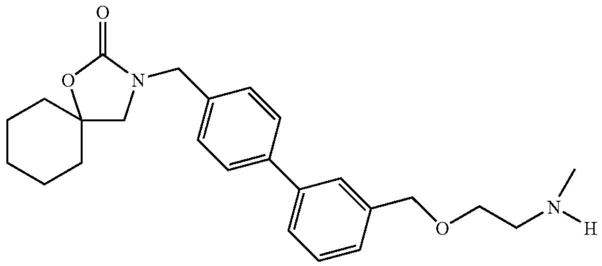 | 3-[3'-(2-Methylamino-ethoxymethyl)-biphenyl-4-ylmethyl]-1-oxa-3-aza-spiro[4.5]decan-2-one |
| 12.1 | 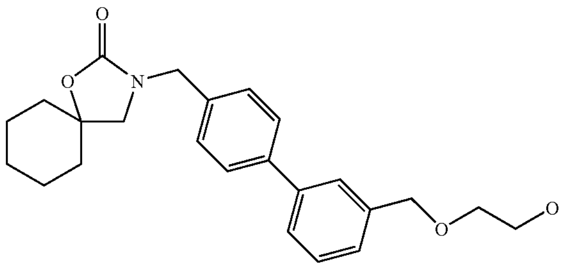 | 3-[3'-(2-Hydroxy-ethoxymethyl)-biphenyl-4-ylmethyl]-1-oxa-3-aza-spiro[4.5]decan-2-one |
| 12.2 | 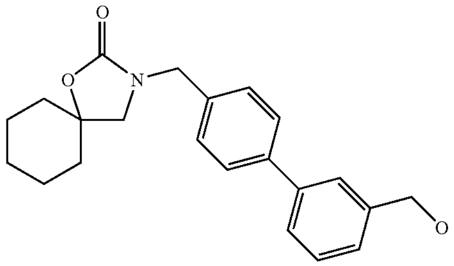 | 3-(3'-Hydroxymethyl-biphenyl-4-ylmethyl)-1-oxa-3-aza-spiro[4.5]decan-2-one |

-continued

| Example No. | Structure | Name |
|---|---|---|
| 13.1 | 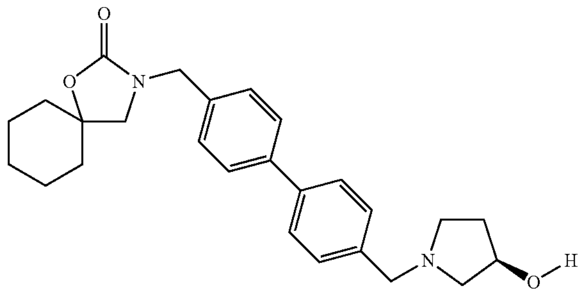 | 3-[4'-(3-Hydroxy-pyrrolidin-1-ylmethyl)-biphenyl-4-ylmethyl]-1-oxa-3-aza-spiro[4.5]decan-2-one |
| 18.1 | 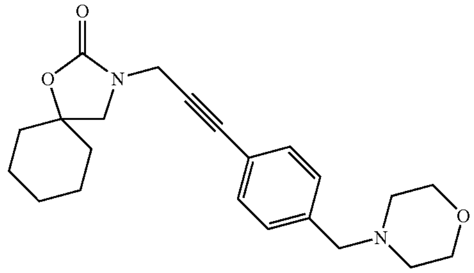 | 3-[3(4-morpholin-4-ylmethyl-phenyl)-prop-2-ynyl]-1-oxa-3-aza-spiro[4.5]decan-2-one |

Pharmaceutical Compositions

The compounds of the present invention may be formulated into conventional pharmaceutical composition comprising a compound of Formula I, or a pharmaceutically acceptable salt or solvate thereof, in association with a pharmaceutically acceptable carrier or excipient. The pharmaceutically acceptable carriers can be either solid or liquid. Solid form preparations include, but are not limited to, powders, tablets, dispersible granules, capsules, cachets, and suppositories.

A solid carrier can be one or more substances, which may also act as diluents, flavoring agents, solubilizers, lubricants, suspending agents, binders, or table disintegrating agents. A solid carrier can also be an encapsulating material.

In powders, the carrier is a finely divided solid, which is in a mixture with the finely divided compound of the invention, or the active component. In tablets, the active component is mixed with the carrier having the necessary binding properties in suitable proportions and compacted in the shape and size desired.

For preparing suppository compositions, a low-melting wax such as a mixture of fatty acid glycerides and cocoa butter is first melted and the active ingredient is dispersed therein by, for example, stirring. The molten homogeneous mixture is then poured into convenient sized moulds and allowed to cool and solidify.

Suitable carriers include, but are not limited to, magnesium carbonate, magnesium stearate, talc, lactose, sugar, pectin, dextrin, starch, tragacanth, methyl cellulose, sodium carboxymethyl cellulose, low-melting wax, cocoa butter, and the like.

The term composition is also intended to include the formulation of the active component with encapsulating material as a carrier providing a capsule in which the active component (with or without other carriers) is surrounded by a carrier which is thus in association with it. Similarly, cachets are included.

Tablets, powders, cachets, and capsules can be used as solid dosage forms suitable for oral administration.

Liquid form compositions include solutions, suspensions, and emulsions. For example, sterile water or water propylene glycol solutions of the active compounds may be liquid preparations suitable for parenteral administration. Liquid compositions can also be formulated in solution in aqueous polyethylene glycol solution.

Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art. Exemplary compositions intended for oral use may contain one or more coloring, sweetening, flavoring and/or preservative agents.

Depending on the mode of administration, the pharmaceutical composition will include from about 0.05% w (percent by weight) to about 99% w, more particularly, from about 0.10% w to 50% w, of the compound of the invention, all percentages by weight being based on the total weight of the composition.

A therapeutically effective amount for the practice of the present invention can be determined by one of ordinary skill in the art using known criteria including the age, weight and response of the individual patient, and interpreted within the context of the disease which is being treated or which is being prevented.

Medical Use

It is contemplated that compounds of the present invention will exhibit activity as pharmaceuticals, in particular as modulators of metabotropic glutamate receptors. More particularly, the compounds of the present invention exhibit activity as potentiators of the mGluR2 receptor, and are contemplated to be useful in therapy, in particular for the treatment of neurological and psychiatric disorders associated with glutamate dysfunction in an animal.

More specifically, the neurological and psychiatric disorders include, but are not limited to, disorders such as cerebral deficit subsequent to cardiac bypass surgery and grafting, stroke, cerebral ischemia, spinal cord trauma, head trauma, perinatal hypoxia, cardiac arrest, hypoglycemic neuronal damage, dementia (including AIDS-induced dementia), Alzheimer's disease, Huntington's Chorea, amyotrophic lateral sclerosis, ocular damage, retinopathy, cognitive disorders, idiopathic and drug-induced Parkinson's disease, muscular spasms and disorders associated with muscular spasticity including tremors, epilepsy, convulsions, cerebral deficits secondary to prolonged status epilepticus, migraine (including migraine headache), urinary incontinence, substance tolerance, substance withdrawal (including, substances such as opiates, nicotine, tobacco products, alcohol, benzodiazepines, cocaine, sedatives, hypnotics, etc.), psychosis, schizophrenia, anxiety (including generalized anxiety disorder, panic disorder, social phobia, obsessive compulsive disorder, and post-traumatic stress disorder (PTSD)), mood disorders (including depression, mania, bipolar disorders), circadian rhythm disorders (including jet lag and shift work), trigeminal neuralgia, hearing loss, tinnitus, macular degeneration of the eye, emesis, brain edema, pain (including acute and chronic pain states, severe pain, intractable pain, neuropathic pain, inflammatory pain, and post-traumatic pain), tardive dyskinesia, sleep disorders (including narcolepsy), attention deficit/hyperactivity disorder, and conduct disorder.

The invention thus provides a use of any of the compounds according to Formula I, or a pharmaceutically acceptable salt or solvate thereof, for the manufacture of a medicament for the treatment of any of the conditions discussed above.

Additionally, the invention provides a method for the treatment of a subject suffering from any of the conditions discussed above, whereby an effective amount of a compound according to Formula I or a pharmaceutically acceptable salt or solvate thereof, is administered to a patient in need of such treatment. The invention also provides a compound of Formula I or pharmaceutically acceptable salt or solvate thereof, as hereinbefore defined for use in therapy.

In the context of the present specification, the term "therapy" also includes "prophylaxis" unless there are specific indications to the contrary. The term "therapeutic" and "therapeutically" should be construed accordingly. The term "therapy" within the context of the present invention further encompasses the administration of an effective amount of a compound of the present invention, to mitigate either a pre-existing disease state, acute or chronic, or to mitigate a recurring condition. This definition also encompasses prophylactic therapies for prevention of recurring conditions and continued therapy for chronic disorders. In use for therapy in a warm-blooded animal such as a human, the compounds of the present invention may be administered in the form of a conventional pharmaceutical composition by any route including orally, intramuscularly, subcutaneously, topically, intranasally, intraperitoneally, intrathoracically, intravenously, epidurally, intrathecally, intracerebroventricularly and by injection into the joints. In preferred embodiments of the invention, the route of administration is oral, intravenous, or intramuscular.

The dosage will depend on the route of administration, the severity of the disease, age and weight of the patient and other factors normally considered by the attending physician, who determines the individual regimen and dosage level for a particular patient.

As mentioned above, the compounds described herein may be provided or delivered in a form suitable for oral use, for example, in a tablet, lozenge, hard and soft capsule, aqueous solution, oily solution, emulsion, and suspension. Alternatively, the compounds may be formulated into a topical administration, for example, as a cream, ointment, gel, spray, or aqueous solution, oily solution, emulsion or suspension. The compounds described herein also may be provided in a form that is suitable for nasal administration, for example, as a nasal spray, nasal drops, or dry powder. The compounds can be administered to the vagina or rectum in the form of a suppository. The compounds described herein also may be administered parentally, for example, by intravenous, intravesicular, subcutaneous, or intramuscular injection or infusion. The compounds can be administered by insufflation (for example as a finely divided powder). The compounds may also be administered transdermally or sublingually.

In addition to their use in therapeutic medicine, the compounds of Formula I, or salts thereof, are useful as pharmacological tools in the development and standardization of in vitro and in vivo test systems for the evaluation of the effects of inhibitors of mGluR-related activity in laboratory animals as part of the search for new therapeutics agents. Such animals include, for example, cats, dogs, rabbits, monkeys, rats and mice.

Process for Preparing Compounds

Compounds of the present invention can be prepared by various synthetic processes. The selection of a particular process to prepare a given compound is within the purview of the person of skill in the art. The choice of particular structural features and/or substituents may therefore influence the selection of one process over another.

Within these general guidelines, the following processes can be used to prepare exemplary subsets of compounds of this invention. Unless indicated otherwise, the variables described in the following schemes and processes have the same definitions as those given for Formula I above.

In one process, for example, compounds of Formula I wherein L is an alkylene moiety and A and B are phenyl groups may be prepared as shown in Scheme 1, below:

Scheme 1

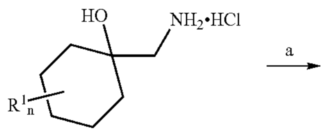

(i)

-continued

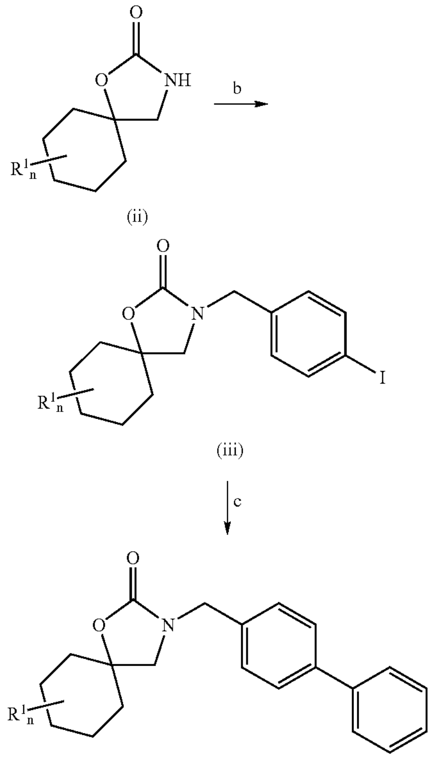

(ii)

(iii)

(iv)

a) $CH_2CL_2$, $NEt_3$ di-2-pyridyl carbonate, O/N, RT.
b) CH3CN, 4-Iodobenzyl bromide, CsCO3, 70° C., 4 h
c) dimethoxy ethane, boronate ester or boronic acid, 2M aq. sodium carbonate, $Pd(PPh_3)_4$, 100°-110° C., 1.5 h Alternatively, as shown in Scheme 2, below, such compounds may be prepared by coupling iodo intermediate (v) with aryl tin reagent (vi):

Scheme 2

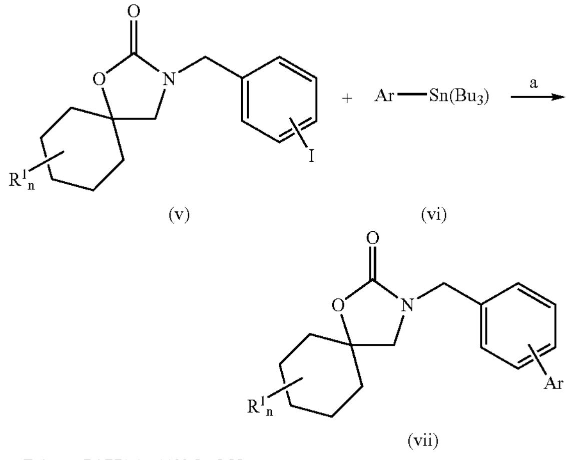

(v) (vi)

(vii)

a. Toluene, $Pd(PPh_3)_4$, 110° C., O/N

Many variations of the foregoing processes and additions thereto appear throughout the examples that follow. The person of ordinary skill in the art thus will appreciate that the compounds of this invention can be prepared by following or adapting one or more of the processes disclosed herein.

The invention is further illustrated by way of the following examples, which are intended to elaborate several embodiments of the invention. These examples are not intended to, nor are they to be construed to, limit the scope of the invention. It will be clear that the invention may be practiced otherwise than as particularly described herein. Numerous modifications and variations of the present invention are possible in view of the teachings herein and, therefore, are within the scope of the invention.

General Methods

The following abbreviations are used in the examples:

| | |
|---|---|
| BOC | tert-butoxycarbonyl |
| BSA | Bovine Serum Albumin |
| CCD | Charge Coupled Device |
| CRC | Concentration Response Curve |
| DBU | 1,8-diazabicyclo[5.4.0]undec-7-ene |
| DCM | dichloromethane |
| DHPG | 3,5-dihydroxyphenylglycine; |
| DIBAL | diisobutylaluminum hydride |
| DMF | N,N-dimethylformamide |
| DMSO | dimethyl sulfoxide |
| EDTA | Ethylene Diamine Tetraacetic Acid |
| $Et_3N$ | triethylamine |
| EtOAc | Ethyl acetate |
| FLIPR | Fluorometric Imaging Plate reader |
| GC/MS | gas chromatograph coupled mass spectroscopy |
| GHEK | Human Embryonic Kidney expressing Glutamate Transporter |
| HEPES | 4-(2-hydroxyethyl)-1-piperazineethanesulfonic acid (buffer) |
| $IP_3$ | inositol triphosphate |
| MCPBA | 3-chloroperbenzoic acid |
| MeOH | methanol |
| NMP | N-Methylpyrrolidinone |
| NMR | nuclear magnetic resonance |
| PCC | pyridinium chlorochromate |
| ppm | parts per million |
| RT | room temperature |
| SPE | solid phase extraction |
| TFA | trifluoroacetic acid |
| THF | tetrahydrofuran |
| TLC | thin layer chromatography |

All starting materials are commercially available or earlier described in the literature. The $^1H$ and $^{13}C$ NMR spectra were recorded either on Bruker 300, Bruker DPX400 or Varian +400 spectrometers operating at 300, 400 and 400 MHz for $^1H$ NMR respectively, using TMS or the residual solvent signal as reference, in deuterated chloroform as solvent unless otherwise indicated. All reported chemical shifts are in ppm on the delta-scale, and the fine splitting of the signals as appearing in the recordings (s: singlet, br s: broad singlet, d: doublet, t: triplet, q: quartet, m: multiplet).

Analytical in line liquid chromatography separations followed by mass spectra detections, were recorded on a Waters LCMS consisting of an Alliance 2795 (LC) and a ZQ single quadrupole mass spectrometer. The mass spectrometer was equipped with an electrospray ion source operated in a positive and/or negative ion mode. The ion spray voltage was ±3 kV and the mass spectrometer was scanned from m/z 100-700 at a scan time of 0.8 s. To the column, X-Terra MS, Waters, C8, 2.1×50 mm, 3.5 mm, was applied a linear gradient from 5% to 100% acetonitrile in 10 mM ammonium acetate (aq.), or in 0.1% TFA (aq.).

Preparative reversed phase chromatography was run on a Gilson preparative HPLC with UV detection at 254 nm, using a Chiralpak AD 0.46×25 cm column (Daicel Chemical Industries, Ltd.).

Purification of products were also done using Chem Elut Extraction Columns (Varian, cat #1219-8002), Mega BE-SI (Bond Elut Silica) SPE Columns (Varian, cat #12256018; 12256026; 12256034), or by flash chromatography in silica-filled glass columns.

The pharmacological properties of the compounds of the invention can be analyzed using standard assays for functional activity. Examples of glutamate receptor assays are well known in the art as described in, for example, Aramori et al., 1992, Neuron, 8:757; Tanabe et al., 1992, Neuron, 8:169; Miller et al., 1995, J. Neuroscience, 15:6103; Balazs, et al, 1997, J. Neurochemistry, 1997, 69:151. The methodology described in these publications is incorporated herein by reference. Conveniently, the compounds of the invention can be studied by means of an assay that measures the mobilization of intracellular calcium, $[Ca^{2+}]_i$ in cells expressing mGluR2.

A $[^{35}S]$-GTPγS binding assay was used to functionally assay mGluR2 receptor activation. The allosteric activator activity of compounds at the human mGluR2 receptor were measured using a $[^{35}S]$-GTPγS binding assay with membranes prepared from CHO cells which stably express the human mGluR2. The assay is based upon the principle that agonists bind to G-protein coupled receptors to stimulate GDP-GTP exchange at the G-protein. Since $[^{35}S]$-GTPγS is a non-hydrolyzable GTP analog, it can be used to provide an index of GDP-GTP exchange and, thus, receptor activation. The GTPγS binding assay therefore provides a quantitative measure of receptor activation.

Membranes were prepared from CHO cells stably transfected with human mGluR2. Membranes (30 μg protein) were incubated with test compound (3 nM to 300 μM) for 15 minutes at room temperature prior to the addition of 1 μM glutamate, and incubated for 30 min at 30° C. in 500 μL assay buffer (20 mM HEPES, 100 mM NaCl, 10 mM $MgCl_2$), containing 30 μM GDP and 0.1 nM $[^{35}S]$-GTPγS (1250 Ci/mmol). Reactions were carried out in triplicate in 2 mL polypropylene 96-well plates. Reactions were terminated by vacuum filtration using a Packard 96-well harvester and Unifilter-96, GF/B filter microplates. The filter plates were washed 4×1.5 mL with ice-cold wash buffer (10 mM sodium phosphate buffer, pH 7.4). The filter plates were dried and 35 μL of scintillation fluid (Microscint 20) was added to each well. The amount of radioactivity bound was determined by counting plates on a Packard TopCount. Data was analyzed using GraphPad Prism, and $EC_{50}$ and $E_{max}$ values (relative to the maximum glutamate effect) were calculated using non-linear regression.

Generally, compounds of the present invention were active in the assays described herein at concentrations (or with $EC_{50}$ values) of less than about 10 μM. Preferred compounds of the invention have $EC_{50}$ values of less than 1 μM; more preferred compounds of less than about 100 nM. For example, compounds of Examples 1.1, 1.6, 1.30, 1.49 and 3.2 have $EC_{50}$ values of 326, 14, 1000, 381 and 95 nM, respectively.

EXAMPLES

Example 1.1

3-(2'-Morpholin-4-ylmethyl-biphenyl-4-ylmethyl)-1-oxa-3-aza-spiro[4.5]decan-2-one

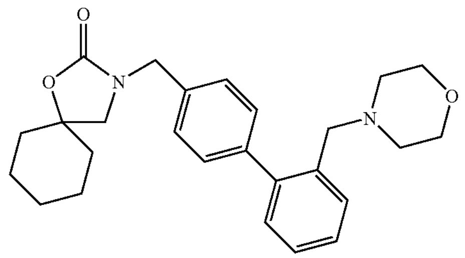

3-(4-Iodo-benzyl)-1-oxa-3-aza-spiro[4.5]decan-2-one (55 mg, 0.148 mmol) and benzylmopholine-2-boronic acid (49 mg, 0.222 mmol) were mixed in ethylene glycol dimethyl ether (1 mL) and sodium carbonate (2M) aqueous solution (1 mL). Tetrakis(triphenylphosphine)palladium ($Pd(PPh_3)_4$) (17 mg, 0.0148 mmol) was added and the reaction mixture was heated at 100~110° C. for 1~1.5 hours. The reaction was diluted with dichloromethane (DCM), washed with water (4 mL) and brine (4 mL). The organic phase was separated, dried over anhydrous sodium sulfate and concentrated. The crude residue was purified on silica gel eluting with 5-30% ethyl acetate in hexane to give the product as off-white solid (52 mg, 83%). $^1H$ NMR (300 MHz, $CDCl_3$): δ 7.49 (m, 1H), 7.42 (d, 2H), 7.32 (m, 5H), 4.5 (s, 2H), 3.65 (t, 4H), 3.39 (s, 2H), 3.18 (s, 2H), 2.36 (t, 4H), 1.82 (m, 4H), 1.54 (m, 6H).

In a similar manner the following compounds were synthesized:

| Example | Structure | Name | Yield |
|---|---|---|---|
| 1.2 | 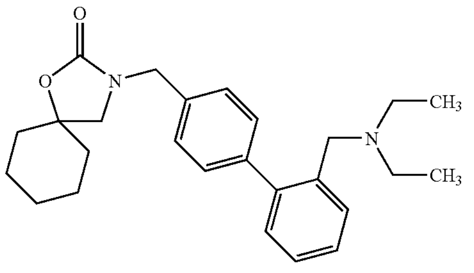 | 3-(2'-Diethyl aminomethyl-biphenyl-4-ylmethyl)-1-oxa-3-aza-spiro[4.5]decan-2-one | Colorless oil, 31 mg, 63% |
| NMR | $^1H$ NMR (300 MHz, $CDCl_3$): δ (ppm) = 7.61 (d, 1H), 7.34 (m, 7H), 4.5 (s, 2H), 3.47 (s, 2H), 3.17 (s, 2H), 2.41 (q, 4H), 1.79 (m, 4H), 1.47 (m, 6H), 0.89 (t, 6H) | | |

-continued

| Example | Structure | Name | Yield |
|---|---|---|---|
| 1.3 | 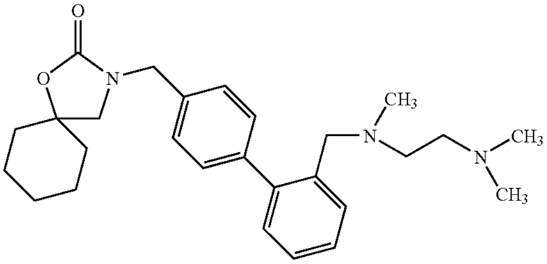 | 3-(2'-{[(2-Dimethyl amino-ethyl)-methyl-amino]-methyl}-biphenyl-4-ylmethyl)-1-oxa-3-aza-spiro [4.5]decan-2-one | Colorless oil, 32 mg, 61% |
| NMR | $^1$H NMR (300 MHz, $CDCl_3$): δ (ppm) = 7.59 (d, 1H), 7.32 (m, 7H), 4.49 (s, 2H), 3.43 (s, 2H), 3.18 (s, 2H), 2.37 (m, 4H), 2.19 (s, 6H), 2.14 (s, 3H), 1.8 (m, 4H), 1.57 (m, 6H) | | |
| 1.4 | 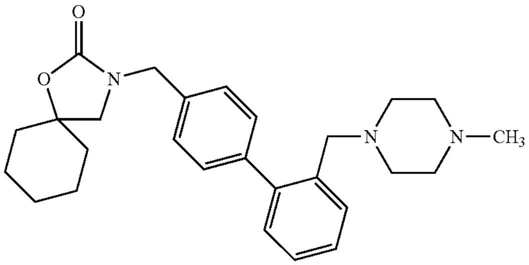 | 3-[2'-(4-Methyl-piperazin-1-yl methyl)-biphenyl-4-ylmethyl]-1-oxa-3-aza-spiro[4.5]decan-2-one | Off-white solid, 36 mg, 69% |
| NMR | $^1$H NMR (300 MHz, $CDCl_3$): δ (ppm) = 7.48 (m, 1H), 7.42 (d, 2H), 7.32 (m, 5H), 4.49 (s, 2H), 3.41 (s, 2H), 3.17 (s, 2H), 2.38 (m, 8H), 2.26 (s, 3H), 1.83 (m, 4H), 1.49 (m, 6H) | | |
| 1.5 | 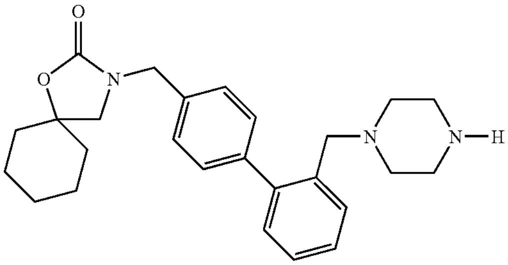 | 3-(2'-Piperazin-1-ylmethyl-biphenyl-4-ylmethyl)-1-oxa-3-aza-spiro[4.5]decan-2-one | Off-white solid, 81% |
| NMR | $^1$H NMR (300 MHz, $CDCl_3$): δ (ppm) = 7.52 (m, 1H), 7.41 (d, 2H), 7.27 (m, 5H), 4.49 (s, 2H), 3.36 (s, 2H), 3.17 (s, 2H), 2.81 (t, 4H), 2.31 (br, 4H), 1.82 (m, 5H), 1.47 (m,6H) | | |
| 1.6 | 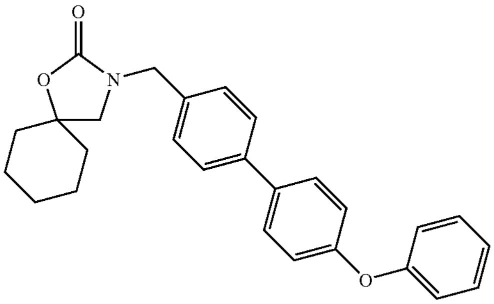 | 3-(4'-Phenoxy-biphenyl-4-ylmethyl)-1-oxa-3-aza-spiro[4.5]decan-2-one | White powder, 74% |
| NMR | $^1$H NMR (300 MHz, $CDCl_3$): δ (ppm) = 7.57 (dd, 4H), 7.36 (m, 4H), 7.08 (m, 5H), 4.49 (s, 2H), 3.15 (s, 2H), 1.79 (m, 4H), 1.46 (m, 6H) | | |

-continued

| Example | Structure | Name | Yield |
|---|---|---|---|
| 1.7 | 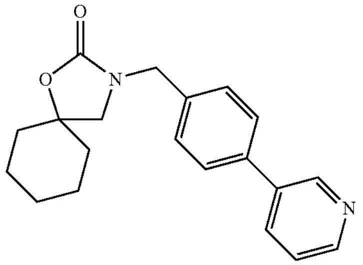 | 3-(4-Pyridin-3-yl-benzyl)-1-oxa-3-aza-spiro[4.5]decan-2-one | White solid, quantitative yield |
| NMR | $^1$H NMR (300 MHz, $CDCl_3$): δ (ppm) = 8.01 (d, 1H), 7.49 (m, 7H), 4.49 (s, 2H), 3.15 (s, 2H), 1.79 (m, 4H), 1.46 (m, 6H) | | |
| 1.8 | 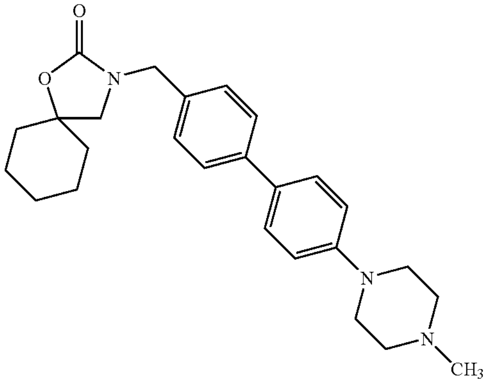 | 3-[4'-(4-Methyl-piperazin-1-yl)-biphenyl-4-ylmethyl]-1-oxa-3-aza-spiro[4.5]decan-2-one | White powder, quantitative yield |
| NMR | $^1$H NMR (300 MHz, $CDCl_3$): δ (ppm) = 7.55 (m, 4H), 7.3 (dd, 2H), 7.01 (dd, 2H), 4.45 (s, 2H), 3.3 (t, 4H), 3.13 (s, 2H), 2.65 (t, 4H), 2.39 (s, 3H), 1.78 (m, 4H), 1.47 (m, 6H) | | |
| 1.9 | 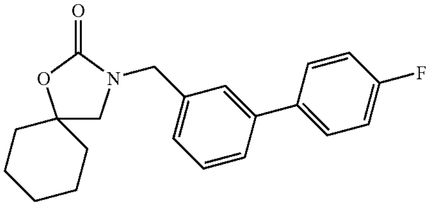 | 3-(4'-Fluoro-biphenyl-3-ylmethyl)-1-oxa-3-aza-spiro[4.5]decan-2-one | Yellow solid, 45.9 mg, 91% |
| NMR | $^1$H NMR (300 MHz, $CDCl_3$): δ (ppm) = 7.55 (m, 2H), 7.49 (m, 1H), 7.45 (m, 2H), 7.28 (m, 1H), 7.15 (t, 2H), 4.50 (s, 2H), 3.15 (s, 2H), 1.80 (m, 4H), 1.47 (m, 6H) | | |
| 1.10 | 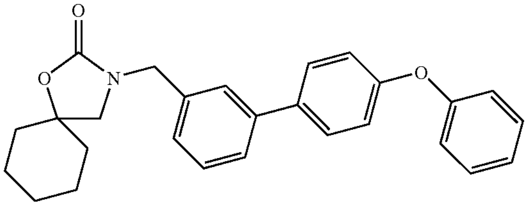 | 3-(4'-Phenoxy-biphenyl-3-ylmethyl)-1-oxa-3-aza-spiro[4.5]decan-2-one | Brown oil, 40.5 mg, 66% |
| NMR | $^1$H NMR (300 MHz, $CDCl_3$): δ (ppm) = 7.56 (m, 3H), 7.38 (m, 5H), 7.08 (m, 5H), 4.51 (s, 2H), 3.15 (s, 2H), 1.74 (m, 4H), 1.50 (m, 6H) | | |

-continued

| Example | Structure | Name | Yield |
|---|---|---|---|
| 1.11 | 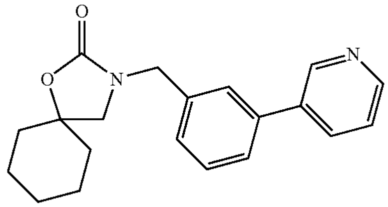 | 3-(3-Pyridin-3-yl-benzyl)-1-oxa-3-aza-spiro[4.5]decan-2-one | Yellow oil 24.5 mg, 51% |
| NMR | $^{1}$H NMR (300 MHz, $CDCl_3$): δ (ppm) = 8.85 (m, 1H), 8.62 (m, 1H), 7.88 (m, 1H), 7.44 (m, 6H), 4.52 (s, 2H), 3.16 (s, 2H), 1.80 (m, 4H), 1.48 (m, 6H) | | |
| 1.12 | 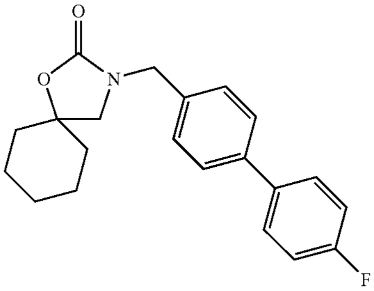 | 3-(4'-Fluoro-biphenyl-4-ylmethyl)-1-oxa-3-aza-spiro[4.5]decan-2-one | White solid, 38 mg, 93% |
| NMR | $^{1}$H NMR (300 MHz, $CDCl_3$): δ (ppm) = 7.55 (m, 4H), 7.34 (d, 2H), 7.14 (t, 2H), 4.48 (s, 2H), 3.15 (s, 2H), 1.79 (m, 4H), 1.45 (m, 6H) | | |
| 1.13 | 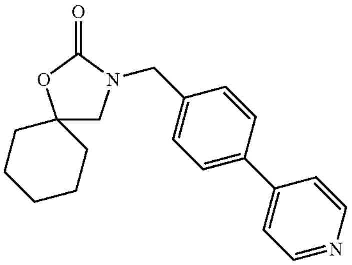 | 3-(4-Pyridin-4-yl-benzyl)-1-oxa-3-aza-spiro[4.5]decan-2-one | White solid, 26 mg, 66% |
| NMR | $^{1}$H NMR (300 MHz, $CDCl_3$): δ (ppm) = 8.68 (d, 2H), 7.66 (d, 2H), 7.51 (m, 2H), 7.39 (d, 2H), 4.49 (s, 2H), 3.15 (s, 2H), 1.79 (m, 4H), 1.44 (m, 6H) | | |
| 1.14 | 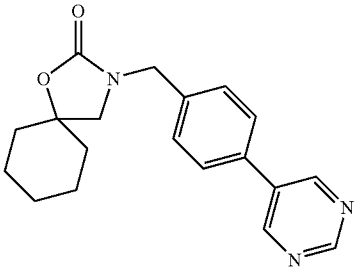 | 3-(4-Pyrimidin-5-yl-benzyl)-1-oxa-3-aza-spiro[4.5]decan-2-one | Colorless oil, 15 mg, 38% |
| NMR | $^{1}$H NMR (300 MHz, $CDCl_3$): δ (ppm) = 9.24 (br, 1H), 8.98 (br, 2H), 7.6 (d, 2H), 7.45 (d, 2H), 4.51 (s, 2H), 3.16 (s, 2H), 1.77 (m, 4H), 1.47 (m, 6H) | | |
| 1.15 | 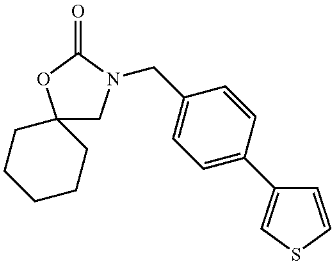 | 3-(4-Thiophen-3-yl-benzyl)-1-oxa-3-aza-spiro[4.5]decan-2-one | White solid, 34 mg, 86% |

-continued

| Example | Structure | Name | Yield |
|---|---|---|---|
| NMR | $^1$H NMR (300 MHz, $CDCl_3$): δ (ppm) = 7.62 (d, 2H), 7.58 (d, 1H), 7.4 (d, 2H), 7.3 (t, 2H), 4.45 (s, 2H), 3.13 (s, 2H), 1.79 (m, 4H), 1.44 (m, 6H) | | |
| 1.16 | 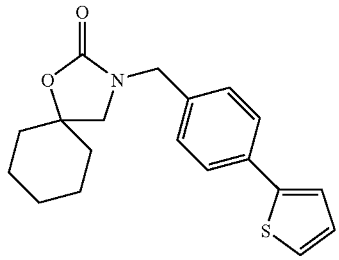 | 3-(4-Thiophen-2-yl-benzyl)-1-oxa-3-aza-spiro[4.5]decan-2-one | White solid, 23 mg, 58% |
| NMR | $^1$H NMR (300 MHz, $CDCl_3$): δ (ppm) = 7.7 (d, 2H), 7.6 (dd, 1H), 7.36 (m, 2H), 7.03 (d, 2H), 4.37 (s, 2H), 3.09 (s, 2H), 1.82 (m, 4H), 1.45 (m, 6H) | | |
| 1.17 | 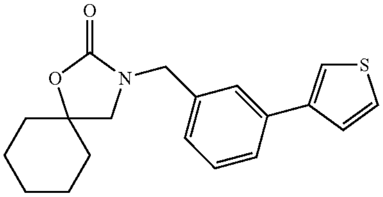 | 3-(3-Thiophen-3-yl-benzyl)-1-oxa-3-aza-spiro[4.5]decan-2-one | Light brown oil, 45 mg, 93% |
| NMR | $^1$H NMR (300 MHz, $CDCl_3$): δ (ppm) = 7.51 (m, 1H), 7.43 (m, 2H), 7.41 (m, 3H), 7.20 (m, 1H), 4.48 (s, 2H), 3.14 (s, 2H), 1.79 (m, 4H), 1.45 (m, 6H) | | |
| 1.18 | 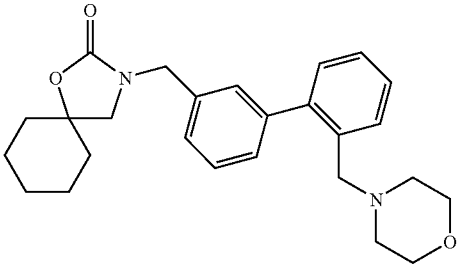 | 3-(3-Thiazol-2-yl-benzyl)-1-oxa-3-aza-spiro[4.5]decan-2-one | Light brown oil, 55 mg, 89% |
| NMR | $^1$H NMR (300 MHz, $CDCl_3$): δ (ppm) = 7.52 (m, 1H), 7.37 (m, 5H), 7.27 (m, 2H), 4.48 (s, 2H), 3.65 (t, 4H), 3.39 (s, 2H), 3.16 (s, 2H), 2.35 (t, 4H), 1.80 (m, 4H), 1.51 (m, 6H) | | |
| 1.19 | 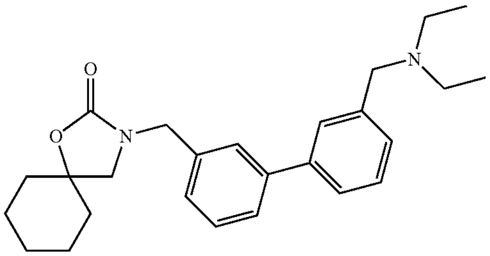 | 3-(3'-Diethylamino methyl-biphenyl-3-yl methyl)-1-oxa-3-aza-spiro[4.5]decan-2-one | Colorless oil, 11.1 mg, 30% |
| NMR | $^1$H NMR (300 MHz, $CDCl_3$): δ (ppm) = 7.56 (m, 2H), 7.44 (m, 5H), 7.28 (m, 1H), 4.51 (s, 2H), 3.65 (s, 2H), 3.15 (s, 2H), 2.58 (q, 4H), 1.80 (m, 4H), 1.51 (m, 6H), 1.08 (t, 6H) | | |

-continued

| Example | Structure | Name | Yield |
|---|---|---|---|
| 1.20 | 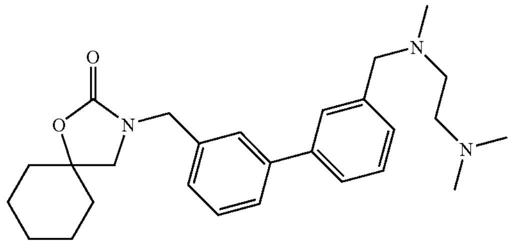 | 3-(3'-{[(2-Dimethyl amino-ethyl)-methyl-amino]-methyl}-biphenyl-3-ylmethyl)-1-oxa-3-aza-spiro [4.5]decan-2-one | Yellow oil, 11.5 mg, 29% |
| NMR | $^{1}H$ NMR (300 MHz, $CDCl_3$): δ (ppm) = 7.55 (m, 2H), 7.42 (m, 5H), 7.26 (m, 1H), 4.51(s, 2H), 3.60 (s, 2H), 3.15 (s, 2H), 2.50 (m, 4H), 2.29 (s, 3H), 2.23 (s, 6H), 1.81 (m, 4H), 1.51 (m, 6H) | | |
| 1.21 | 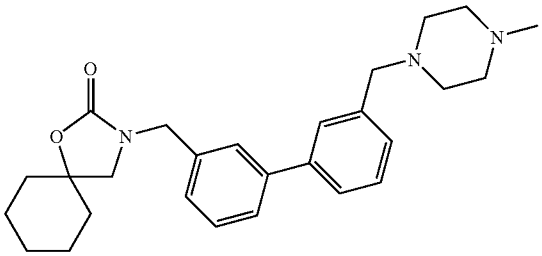 | 3-[3'-(4-Methyl-piperazin-1-ylmethyl)-biphenyl-3-ylmethyl]-1-oxa-3-aza-spiro [4.5]decan-2-one | Light yellow oil, 31.9 mg, 76% |
| NMR | $^{1}H$ NMR (300 MHz, $CDCl_3$): δ (ppm) = 7.45 (m, 8H), 4.51 (s, 2H), 3.59 (s, 2H), 3.15 (s, 2H), 2.49 (m, 8H), 2.30 (s, 3H), 1.80 (m, 4H), 1.49 (m, 6H). | | |
| 1.22 | 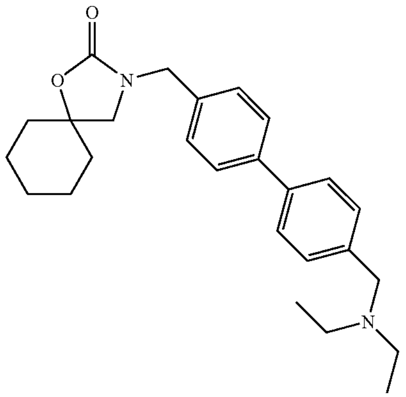 | 3-(4'-Diethylamino methyl-biphenyl-4-ylmethyl)-1-oxa-3-aza-spiro[4.5]decan-2-one | Brown solid, 48.2 mg, 96% |
| NMR | $^{1}H$ NMR (300 MHz, $CDCl_3$): δ (ppm) = 7.56 (m, 4H), 7.43 (m, 2H), 7.35 (m, 2H), 4.48 (s, 2H), 3.63 (s, 2H), 3.15 (s, 2H), 2.57 (q, 4H), 1.81 (m, 4H), 1.52 (m, 6H), 1.09 (t, 6H) | | |
| 1.23 | 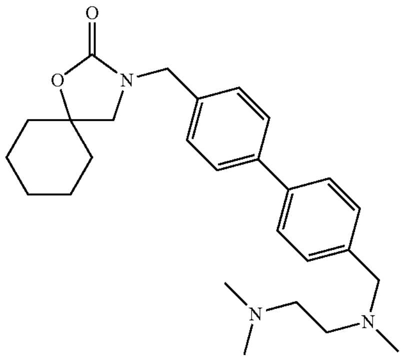 | 3-(4'-{[(2-Dimethylamino-ethyl)-methyl-amino]-methyl}-biphenyl-4-ylmethyl)-1-oxa-3-aza-spiro [4.5]decan-2-one | White solid, 34.8 mg, 66% |
| NMR | $^{1}H$ NMR (300 MHz, $CDCl_3$): δ (ppm) = 7.58 (m, 4H), 1.41 (m, 2H), 7.35 (m, 2H), 4.48 (s, 2H), 3.58 (s, 2H), 3.14 (s, 2H), 2.50 (m, 4H), 2.82 (s, 3H), 2.23 (s, 6H), 1.56 (m, 4H), 1.48 (m, 6H) | | |

-continued

| Example | Structure | Name | Yield |
|---|---|---|---|
| 1.24 | 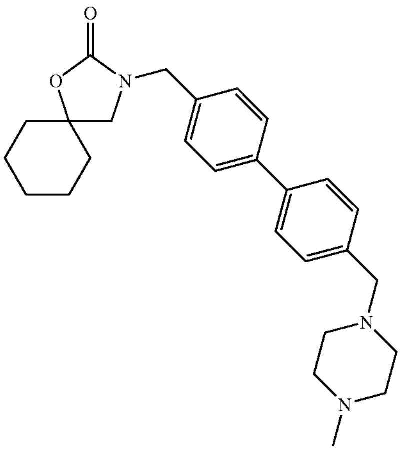 | 3-[4'-(4-Methyl-piperazin-1-ylmethyl)-biphenyl-4-ylmethyl]-1-oxa-3-aza-spiro[4.5]decan-2-one | Brown solid, 53.5 mg, 88% |
| NMR | $^1$H NMR (300 MHz, $CDCl_3$): δ (ppm) = 7.59 (m, 4H), 7.40 (m, 2H), 7.34 (m, 2H), 4.47 (s, 2H), 3.56 (s, 2H), 3.14 (s, 2H), 2.55 (m, 8H), 2.31 (s, 3H), 1.79 (m, 4H), 1.48 (m, 6H) | | |
| 1.25 | 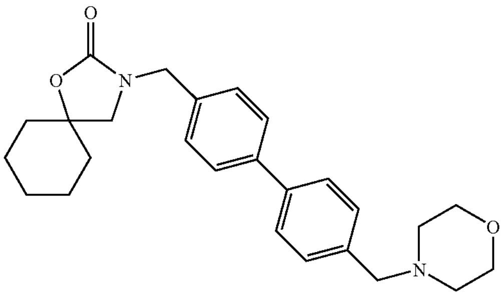 | 3-(4'-Morpholin-4-ylmethyl-biphenyl-4-ylmethyl)-1-oxa-3-aza-spiro[4.5]decan-2-one | Off-white solid, 16.7 mg, 37% |
| NMR | $^1$H NMR (300 MHz, $CDCl_3$): δ (ppm) = 7.57 (m, 4H), 7.42 (m, 2H), 7.35 (m, 2H), 4.48 (s, 2H), 3.75 (m, 4H), 3.57 (s, 2H), 3.15 (s, 2H), 2.50 (m, 4H), 1.73 (m, 4H), 1.45 (m, 6H) | | |
| 1.26 | 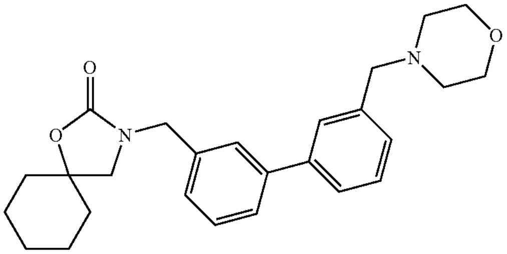 | 3-(3'-Morpholin-4-ylmethyl-biphenyl-3-ylmethyl)-1-oxa-3-aza-spiro[4.5]decan-2-one | Pale yellow oil, 15.5 mg, 26% |
| NMR | $^1$H NMR (300 MHz, $CDCl_3$): δ (ppm) = 7.43 (m, 8H), 4.52 (s, 2H), 3.74 (m, 4H), 3.59 (s, 2H), 3.16 (s, 2H), 2.49 (m, 4H), 1.69 (m, 4H), 1.39 (m, 6H) | | |
| 1.27 | 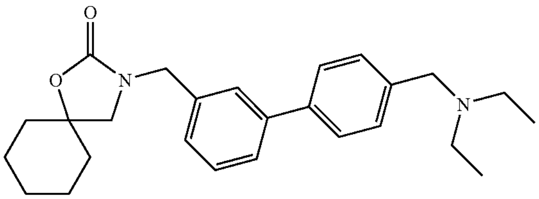 | 3-(4'-Diethyl aminomethyl-biphenyl-3-ylmethyl)-1-oxa-3-aza-spiro[4.5]decan-2-one | Pale yellow oil, 44.7 mg, 89% |
| NMR | $^1$H NMR (300 MHz, $CDCl_3$): δ (ppm) = 7.41 (m, 8H), 4.51 (s, 2H), 3.64 (s, 2H), 3.15 (s, 2H), 2.58 (q, 4H), 1.80 (m, 4H), 1.50 (m, 6H), 1.09 (t, 6H) | | |

-continued

| Example | Structure | Name | Yield |
|---|---|---|---|
| 1.28 | 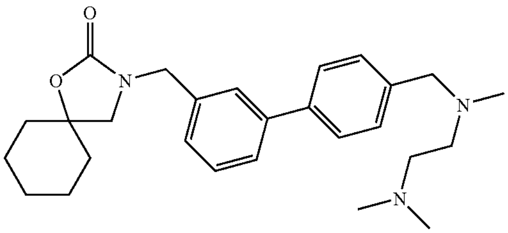 | 3-(4'-{[(2-Dimethyl amino-ethyl)-methyl-amino]-methyl}-biphenyl-3-ylmethyl)-1-oxa-3-aza-spiro [4.5]decan-2-one | Brown oil, 29.4 mg, 59% |
| NMR | $^1$H NMR (300 MHz, $CDCl_3$): δ (ppm) = 7.55 (m, 3H), 7.44 (m, 4H), 7.25 (m, 1H), 4.50 (s, 2H), 3.58 (s, 2H), 3.15 (s, 2H), 2.50 (m, 4H), 2.28 (s, 3H), 2.24 (s, 6H), 1.81 (m, 4H), 1.48 (m, 6H) | | |
| 1.29 | 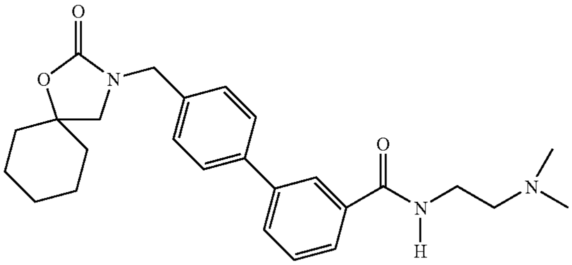 | 4'-(2-Oxo-1-oxa-3-aza-spiro[4.5]dec-3-ylmethyl)-biphenyl-3-carboxylic acid (2-dimethyl amino-ethyl)-amide | White solid, 53 mg, 90.4% |
| NMR | $^1$H NMR (300 MHz, $CDCl_3$): δ (ppm) = 8.05 (t, 1H), 7.73 (m, 2H), 7.61 (d, 2H), 7.44 (m, 1H), 7.34 (d, 2H), 6.98 (br, 1H), 4.47 (s, 2H), 3.56 (m, 2H), 3.14 (s, 2H), 2.54 (t, 2H), 2.27 (s, 6H), 1.79 (m, 4H), 1.46 (m, 6H) | | |
| 1.30 | 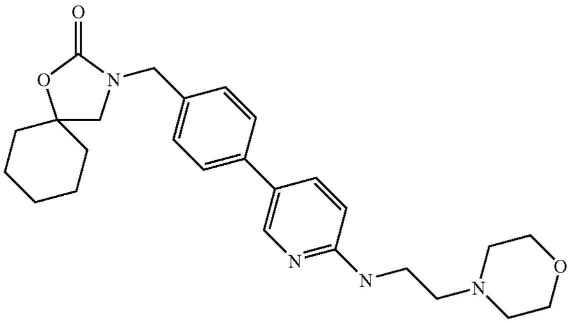 | 3-{4-[6-(2-Morpholin-4-yl-ethylamino)-pyridin-3-yl]-benzyl}-1-oxa-3-aza-spiro[4.5]decan-2-one | Pale yellow oil, 41 mg, 68% |
| NMR | $^1$H NMR (300 MHz, $CDCl_3$): δ (ppm) = 8.35 (d, 1H), 7.68 (dd, 1H), 7.51 (d, 2H), 7.3 (t, 2H), 6.5 (d, 1H), 5.23 (br, 1H), 4.45 (s, 2H), 3.74 (t, 4H), 3.41 (q, 2H), 3.13 (s, 2H), 2.65 (t, 2H), 2.51 (t, 4H), 1.79 (m, 4H), 1.43 (m, 6H) | | |
| 1.31 | 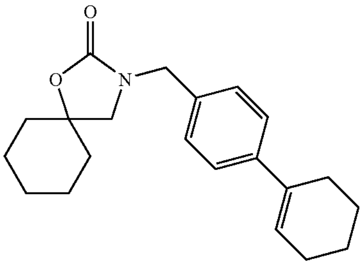 | 3-(4-Cyclohex-1-enyl-benzyl)-1-oxa-3-aza-spiro[4.5]decan-2-one | White powder, 32 mg, 73% |
| NMR | $^1$H NMR (300 MHz, $CDCl_3$): δ (ppm) = 7.39 (dd, 2H), 7.22 (d, 2H), 6.16 (m, 1H), 4.41 (s, 2H), 3.1 (s, 2H), 2.41 (br, 2H), 2.23 (br, 2H), 1.8 (m, 7H), 1.66 (m, 7H) | | |

-continued

| Example | Structure | Name | Yield |
|---|---|---|---|
| 1.32 | 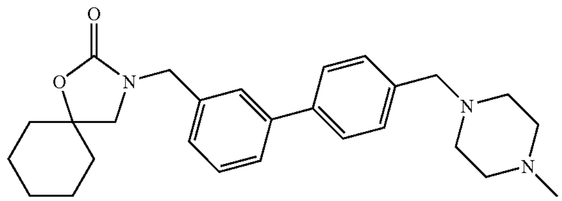 | 3-[4'-(4-Methyl-piperazin-1-ylmethyl)-biphenyl-3-ylmethyl]-1-oxa-3-aza-spiro[4.5]decan-2-one | Brown solid, 35.7 mg, 70% |
| NMR | $^1$H NMR (300 MHz, $CDCl_3$): δ (ppm) = 7.52 (m, 3H), 7.43 (m, 4H), 7.25 (m, 1H), 4.50 (s, 2H), 3.57 (s, 2H), 3.15 (s, 2H), 2.52 (m, 8H), 2.31 (s, 3H), 1.80 (m, 4H), 1.49 (m, 6H) | | |
| 1.33 | 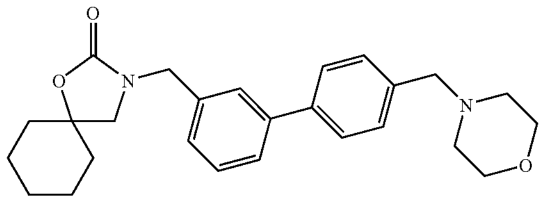 | 3-(4'-Morpholin-4-ylmethyl-biphenyl-3-ylmethyl)-1-oxa-3-aza-spiro[4.5]decan-2-one | Colorless oil, 26.3 mg, 56% |
| NMR | $^1$H NMR (300 MHz, $CDCl_3$): δ (ppm) = 7.53 (m, 3H), 7.43 (m, 4H), 7.25 (m, 1H), 4.50 (s, 2H), 3.75 (m, 4H), 3.56 (s, 2H), 3.15 (s, 2H), 2.50 (m, 4H), 1.81 (m, 4H), 1.49 (m, 6H) | | |
| 1.34 | 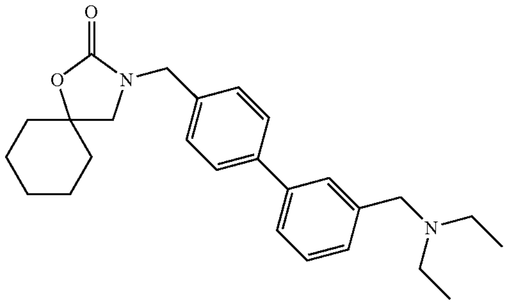 | 3-(3'-Diethylamino methyl-biphenyl-4-ylmethyl)-1-oxa-3-aza-spiro[4.5]decan-2-one | Brown oil, 35.6 mg, 70% |
| NMR | $^1$H NMR (300 MHz, $CDCl_3$): δ (ppm) = 7.60 (m, 2H), 7.41 (m, 6H), 4.48 (s, 2H), 3.65 (s, 2H), 3.14 (s, 2H), 2.58 (q, 4H), 1.80 (m, 4H), 1.55 (m, 6H), 1.08 (t, 6H) | | |
| 1.35 | 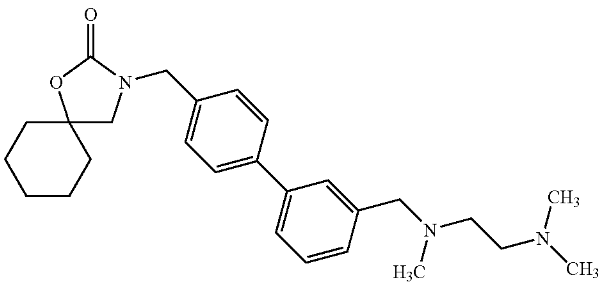 | 3-(3'-{[(2-Dimethyl amino-ethyl)-methyl-amino]-methyl}-biphenyl-4-ylmethyl)-1-oxa-3-aza-spiro[4.5]decan-2-one | Pale yellow oil, 21.2 mg, 58% |
| NMR | $^1$H NMR (300 MHz, $CDCl_3$): δ (ppm) = 7.59 (m, 2H), 7.40 (m, 6H), 4.48 (s, 2H), 3.60 (s, 2H), 3.14 (s, 2H), 2.49 (m, 4H), 2.29 (s, 3H), 2.23 (s, 6H), 1.78 (m, 4H), 1.55 (m, 6H) | | |

-continued

| Example | Structure | Name | Yield |
|---|---|---|---|
| 1.36 | 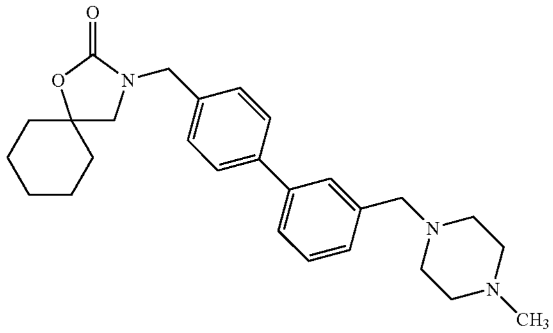 | 3-[3'-(4-Methyl-piperazin-1-ylmethyl)-biphenyl-4-ylmethyl]-1-oxa-3-aza-spiro[4.5]decan-2-one | Dark brown solid, 36.1 mg, 74% |
| NMR | $^1$H NMR (300 MHz, $CDCl_3$): δ (ppm) = 7.45 (m, 8H), 4.48 (s, 2H), 3.59 (s, 2H), 3.15 (s, 2H), 2.51 (m, 8H), 1.92 (s, 3H), 1.82 (m, 4H), 1.50 (m, 6H) | | |
| 1.37 | 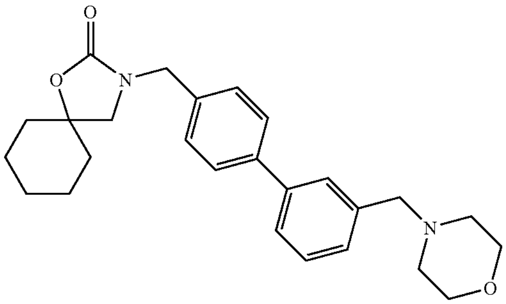 | 3-(3'-Morpholin-4-ylmethyl-biphenyl-4-ylmethyl)-1-oxa-3-aza-spiro[4.5]decan-2-one | Brown solid, 19.5 mg, 24% |
| NMR | $^1$H NMR (300 MHz, $CDCl_3$): δ (ppm) = 7.49 (m, 8H), 4.49 (s, 2H), 3.74 (m, 4H), 3.59 (s, 2H), 3.15 (s, 2H), 2.51 (m, 4H), 1.81 (m, 4H), 1.49 (m, 6H) | | |
| 1.38 | 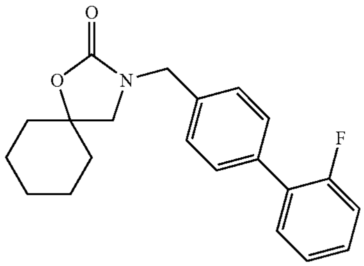 | 3-(2'-Fluoro-biphenyl-4-ylmethyl)-1-oxa-3-aza-spiro[4.5]decan-2-one | White solid, 37.2 mg, 65% |
| NMR | $^1$H NMR (300 MHz, $CDCl_3$): δ (ppm) = 7.57 (m, 2H), 7.45 (m, 1H), 7.37 (m, 3H), 7.24 (m, 2H), 4.49 (s, 2H), 3.17 (s, 2H), 1.81 (m, 4H), 1.45 (m, 6H) | | |
| 1.39 | 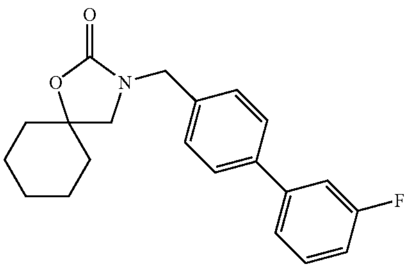 | 3-(3'-Fluoro-biphenyl-4-ylmethyl)-1-oxa-3-aza-spiro[4.5]decan-2-one | White solid, 32.7 mg, 65% |
| NMR | $^1$H NMR (300 MHz, $CDCl_3$): δ (ppm) = 7.58 (m, 2H), 7.36 (m, 5H), 7.06 (m, 1H), 4.49 (s, 2H), 3.15 (s, 2H), 1.80 (m, 4H), 1.51 (m, 6H) | | |

-continued

| Example | Structure | Name | Yield |
|---|---|---|---|
| 1.40 | 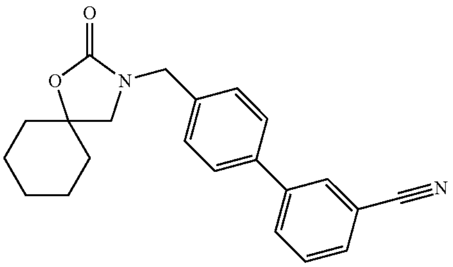 | 4'-(2-Oxo-1-oxa-3-aza-spiro[4.5]dec-3-yl methyl)-biphenyl-3-carbonitrile | Off-white solid, 38.5 mg, 75% |
| NMR | $^1$H NMR (300 MHz, $CDCl_3$): δ (ppm) = 7.84 (m, 2H), 7.64 (m, 1H), 7.58 (m, 3H), 7.40 (m, 2H), 4.50 (s, 2H), 3.16 (s, 2H), 1.80 (m, 4H), 1.49 (m, 6H) | | |
| 1.41 | 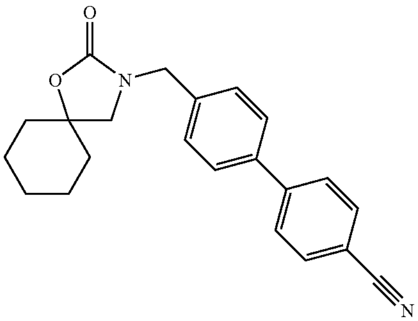 | 4'-(2-Oxo-1-oxa-3-aza-spiro[4.5]dec-3-ylmethyl)-biphenyl-4-carbonitrile | Colorless oil, 35.3 mg, 69% |
| NMR | $^1$H NMR (300 MHz, $CDCl_3$): δ (ppm) = 7.73 (m, 4H), 7.60 (m, 2H), 7.40 (m, 2H), 4.50 (s, 2H), 3.16 (m, 2H), 1.80 (m, 4H), 1.51 (m, 6H) | | |
| 1.42 | 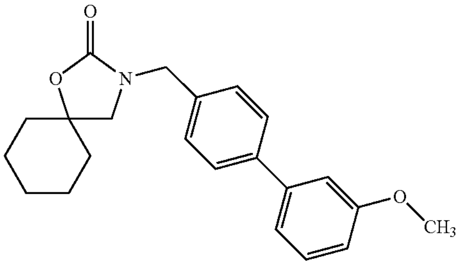 | 3-(3'-Methoxy-biphenyl-4-ylmethyl)-1-oxa-3-aza-spiro[4.5]decan-2-one | Off-white solid, 43.1 mg, 83% |
| NMR | $^1$H NMR (300 MHz, $CDCl_3$): δ (ppm) = 7.60 (m, 2H), 7.36 (m, 3H), 7.20 (m, 1H), 7.14 (m, 1H), 6.94 (m, 1H), 4.48 (s, 2H), 3.89 (s, 3H), 3.15 (s, 2H), 1.79 (m, 4H), 1.50 (m, 6H) | | |
| 1.43 | 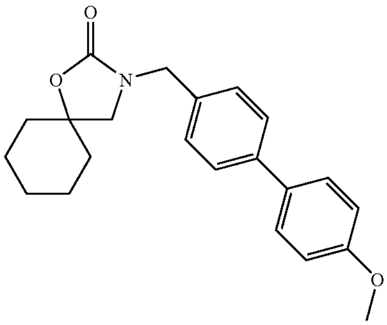 | 3-(4'-Methoxy-biphenyl-4-ylmethyl)-1-oxa-3-aza-spiro[4.5]decan-2-one | White solid, 35.1 mg, 68% |
| NMR | $^1$H NMR (300 MHz, $CDCl_3$): δ (ppm) = 7.54 (m, 4H), 7.33 (m, 2H), 7.00 (m, 2H), 4.47 (s, 2H), 3.87 (s, 3H), 3.14 (s, 2H), 1.77 (m, 4H), 1.49 (m, 6H) | | |

-continued

| Example | Structure | Name | Yield |
|---|---|---|---|
| 1.44 | 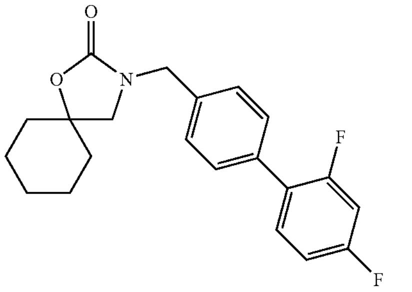 | 3-(2',4'-Difluoro-biphenyl-4-ylmethyl)-1-oxa-3-aza-spiro[4.5]decan-2-one | White solid, 33 mg, 62% |
| NMR | $^1$H NMR (300 MHz, $CDCl_3$): δ (ppm) = 7.51 (m, 2H), 7.42 (m, 1H), 7.36 (m, 2H), 6.94 (m, 2H), 4.49 (s, 2H), 3.16 (s, 2H), 1.79 (m, 4H), 1.50 (m, 6H) | | |
| 1.45 | 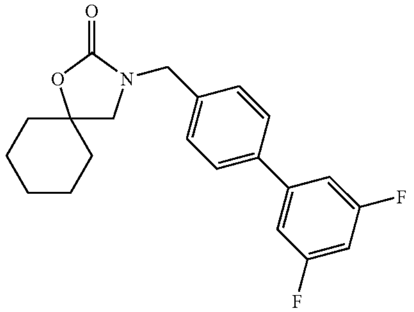 | 3-(3',5'-Difluoro-biphenyl-4-ylmethyl)-1-oxa-3-aza-spiro[4. 5]decan-2-one | Light yellow solid, 44.5 mg, 84% |
| NMR | $^1$H NMR (300 MHz, $CDCl_3$): δ (ppm) = 7.55 (m, 2H), 7.37 (m, 2H), 7.11 (m, 2H), 6.81 (m, 1H), 4.49 (s, 2H), 3.15 (s, 2H), 1.79 (m, 4H), 1.50 (m, 6H) | | |
| 1.46 | 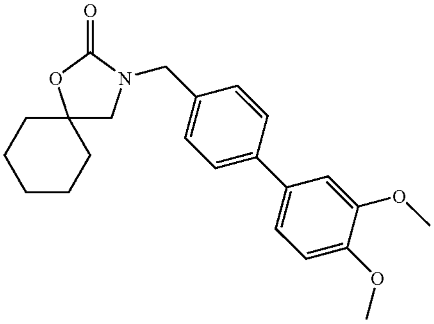 | 3-(3',4'-Dimethoxy-biphenyl-4-ylmethyl)-1-oxa-3-aza-spiro[4.5]decan-2-one | White solid, 37.6 mg, 67% |
| NMR | $^1$H NMR (300 MHz, $CDCl_3$): δ (ppm) = 7.56 (m, 2H), 7.33 (m, 2H), 7.14 (m, 2H), 6.97 (m, 1H), 4.47 (s, 2H), 3.97 (s, 3H), 3.94 (s, 3H), 3.14 (s, 2H), 1.79 (m, 4H), 1.50 (m, 6H) | | |
| 1.47 | 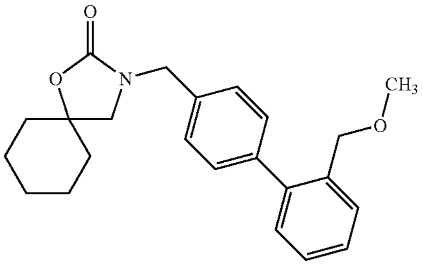 | 3-(2'-Methoxy methyl-biphenyl-4-ylmethyl)-1-oxa-3-aza-spiro[4.5]decan-2-one | Light yellow oil, 45.1 mg, 83% |
| NMR | $^1$H NMR (300 MHz, $CDCl_3$): δ (ppm) = 7.53 (m, 1H), 7.35 (m, 7H), 4.51 (s, 2H), 4.34 (s, 2H), 3.35 (s, 3H), 3.19 (s, 2H), 1.79 (m, 4H), 1.52 (m, 6H) | | |

-continued

| Example | Structure | Name | Yield |
|---|---|---|---|
| 1.48 | 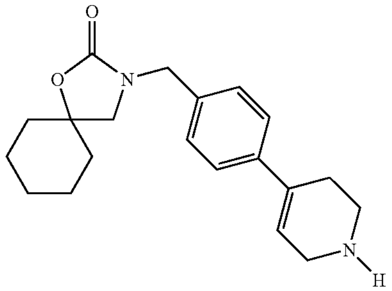 | 3-[4-(1,2,3,6-Tetrahydro-pyridin-4-yl)-benzyl]-1-oxa-3-aza-spiro [4.5]decan-2-one | Off-white solid, 79 mg |
| NMR | $^1$H NMR (300 MHz, $CDCl_3$): δ (ppm) = 7.37 (d, 2H), 7.23 (d, 2H), 6.16 (br, 1H), 4.41 (s, 2H), 3.53 (br, 2H), 3.11 (m, 4H), 2.45 (br, 2H), 1.81 (m, 5H), 1.43 (m, 6H) | | |
| 1.49 | 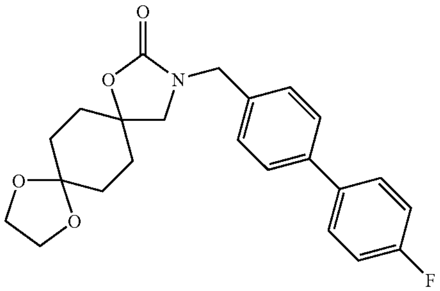 | 3-(4'-Fluoro-biphenyl-4-ylmethyl)-1,9,12-trioxa-3-aza-dispiro[4.2.4.2]tetra decan-2-one | White solid, 53 mg, 46% |
| NMR | $^1$H NMR (300 MHz, $CDCl_3$): δ (ppm) = 7.57 (m, 4H), 7.36 (d, 2H), 7.14 (t, 2H), 4.84 (s, 2H), 3.96 (m, 4H), 3.18 (s, 2H), 2.01 (m, 4H), 1.83 (m, 2H), 1.67 (m, 2H) | | |
| 1.50 | 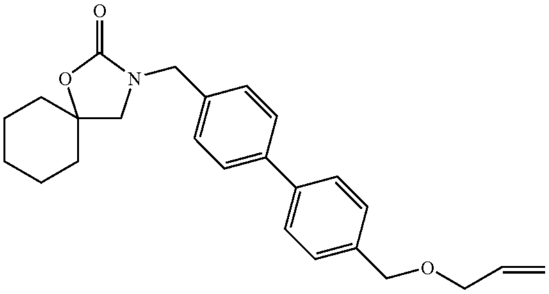 | 3-(4'-Allyloxymethyl-biphenyl-4-ylmethyl)-1-oxa-3-aza-spiro[4.5]decan-2-one | White solid, 67 mg, 62% |
| NMR | $^1$H NMR (300 MHz, $CDCl_3$): δ (ppm) = 7.58 (d, 4H), 7.43 (d, 2H), 7.34 (d, 2H), 5.99 (m, 1H), 5.37 (d, 1H), 5.25 (d, 1H), 4.58 (s, 2H), 4.47 (s, 2H), 4.08 (dt, 2H), 3.14 (s, 2H), 1.78 (m, 4H), 1.47 (m, 6H) | | |
| 1.51 | 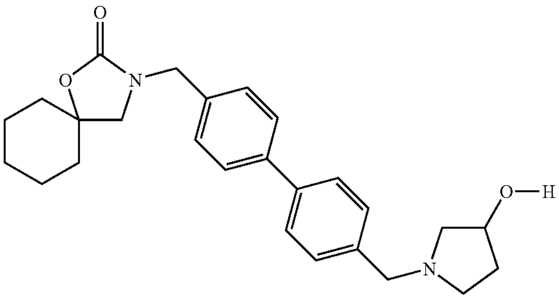 | 3-[4'-(3-Hydroxy-pyrrolidin-1-ylmethyl)-biphenyl-4-ylmethyl]-1-oxa-3-aza-spiro [4.5]decan-2-one | Waxy white solid, 95% |
| NMR | $^1$H NMR (300 MHz, $CDCl_3$): δ (ppm) = 7.58 (dd, 4H), 7.41 (d, 2H), 7.32 (d, 2H), 4.73 (s, 2H), 4.36 (m, 1H), 3.67 (s, 2H), 3.13 (s, 2H), 2.88 (m, 1H), 2.7 (d, 2H), 2.61 (m, 1H), 2.39 (m, 1H), 2.21 (m, 1H), 1.78 (m, 4H), m, 6H) | | |

-continued

| Example | Structure | Name | Yield |
|---|---|---|---|
| 1.52 | 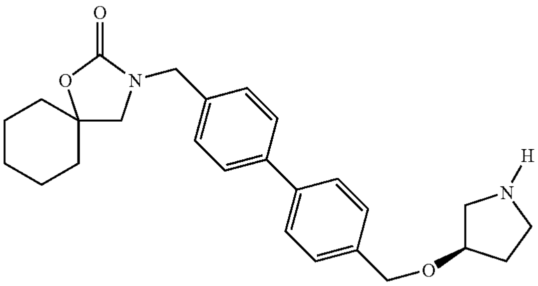 | 3-[4'-(Pyrrolidin-3-yloxymethyl)-biphenyl-4-ylmethyl]-1-oxa-3-aza-spiro[4.5]decan-2-one | Pale brown solid, 59 mg, 40% |
| NMR | $^1$H NMR (300 MHz, $CDCl_3$): δ (ppm) = 7.67 (d, 4H), 7.43 (d, 2H), 7.3 (d, 2H), 4.76 (s, 2H), 4.69 (s, 2H), 4.16 (br, 1H), 3.1 (s, 4H), 2.88 (br, 2H), 2.23 (br, 1H), 1.74 (m, 6H), 1.52 (m, 6H) | | |
| 1.53 | 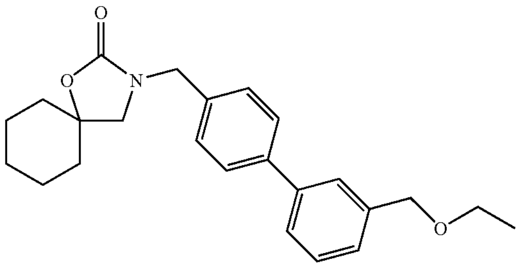 | 3-(3'-Allyloxymethyl-biphenyl-4-ylmethyl)-1-oxa-3-aza-spiro[4.5]decan-2-one | Colorless oil, used in later reaction without further purification |
| NMR | $^1$H NMR (300 MHz, $CDCl_3$): δ (ppm) = 7.6 (m, 3H), 7.53 (m, 1H), 7.45 (t, 1H), 7.33 (d, 3H), 5.96 (m, 1H), 5.31 (m, 2H), 4.59 (s, 2H), 4.47 (s, 2H), 4.09 (d, 2H), 3.09 (s, 2H), 1.78 (m, 4H), 1.48 (m, 6H) | | |
| 1.54 | 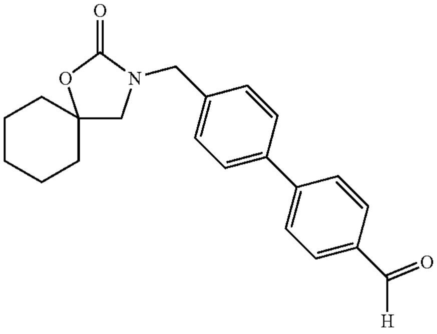 | 4'-(2-Oxo-1-oxa-3-aza-spiro[4.5]dec-3-ylmethyl)-biphenyl-4-carbaldehyde | Beige solid, 230 mg, 70% |
| NMR | $^1$H NMR (300 MHz, $CDCl_3$): δ (ppm) = 10 (s, 1H), 7.92 (d, 2H), 7.71 (d, 2H), 7.58 (d, 2H), 7.37 (d, 2H), 4.45 (s, 2H), 3.09 (s, 2H), 1.76 (m, 4H), 1.49 (m, 6H) | | |
| 1.55 | 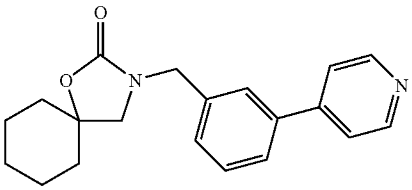 | 3-(3-Pyridin-4-yl-benzyl)-1-oxa-3-aza-spiro[4.5]decan-2-one | Colourless oil, 24 mg, 50% |
| NMR | $^1$H NMR (300 MHz, $CDCl_3$): δ (ppm) = 8.71 (bs, 2H), 7.51 (m, 6H), 4.52 (s, 2H), 3.16 (s, 2H), 1.79 (m, 4H), 1.48 (m, 6H) | | |

-continued

| Example | Structure | Name | Yield |
|---|---|---|---|
| 1.56 | 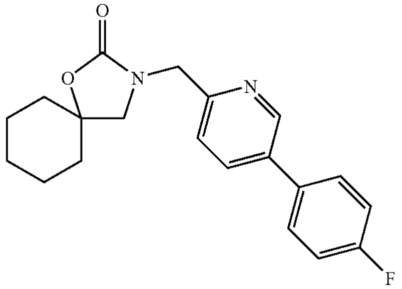 | 3-[5-(4-Fluoro-phenyl)-pyridin-2-ylmethyl]-1-oxa-3-aza-spiro[4.5]decan-2-one | Colourless oil, 54 mg, 94% |
| NMR | $^1$H NMR (300 MHz, $CDCl_3$): δ (ppm) = 8.74 (d, 1H), 7.85 (dd, 1H), 7.65 (m, 1H), 7.54 (m, 2H), 7.17 (t, 2H), 4.59 (s, 2H), 3.32 (s, 2H), 1.82 (m, 4H), 1.47 (m, 6H) | | |
| 1.57 | 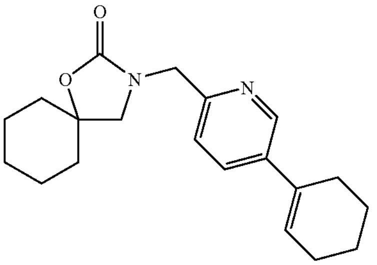 | 3-(5-Cyclohex-1-enyl-pyridin-2-ylmethyl)-1-oxa-3-aza-spiro[4.5]decan-2-one | Colourless oil, 65 mg, 83% |
| NMR | $^1$H NMR (300 MHz, $CDCl_3$): δ (ppm) = 8.77 (d, 1H), 7.61 (dd, 1H), 7.25 (t, 1H), 6.17 (m, 1H), 4.59 (s, 2H), 3.31 (s, 2H), 2.38 (m, 2H), 2.22 (m, 2H), 1.58 (m, 14H) | | |

Example 2.1

1-Oxa-3-aza-spiro[4.5]decan-2-one

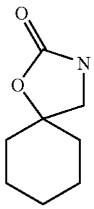

1-Aminomethyl-cyclohexanol hydrogen chloride (250 mg, 1.5 mmol) and triethylamine (0.21 mL, 1.5 mmol) were mixed in dichloromethane (5 mL), and the mixture was stirred for 15 min. Carbonic acid dipyridin-2-yl ester (326 mg, 1.5 mmol) was then added, and the reaction mixture was stirred at room temperature overnight. The reaction mixture was diluted with ethyl acetate (10 mL), washed with water (2×4 mL), brine (2×4 mL); dried over anhydrous sodium sulfate and concentrated to give the title compound as a white powder (174 mg, 74%). $^1$H NMR (300 MHz, $CDCl_3$): δ 6.42 (br, 1H), 3.31 (s, 2H), 1.86 (m, 2H), 1.76 (m, 2H), 1.65 (m, 2H), 1.47 (m, 4H).

Example 3.1

3-(4-Iodo-benzyl)-1-oxa-3-aza-spiro[4.5]decan-2-one

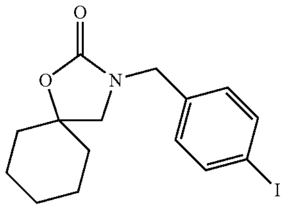

1-Oxa-spiro[4.5]decan-2-one (96 mg, 0.618 mmol), cesium carbonate ($Cs_2CO_3$) (605 mg, 1.855 mmol) and 1-bromomethyl-4-iodo-benzene (220 mg, 0.742 mmol) were mixed in acetonitrile (2.5 mL). The reaction mixture was heated at 70° C. for 5 hours, and the diluted with ethyl acetate (8 mL). The mixture was washed with water (2×4 mL) and brine (2×4 mL). The combined organic phase was dried over anhydrous sodium sulfate and concentrated. The crude residue was purified on silica gel eluting with 5 to 25% ethyl acetate in hexane to give the product as a white powder (112 mg, 49%). $^1$H NMR (300 MHz, $CDCl_3$): δ 7.68 (dd, 2H), 7.03 (dd, 2H), 4.36 (s, 2H), 3.08 (s, 2H), 1.78 (m, 4H), 1.46 (m, In a similar manner the following compounds were synthesized:

| Example | Structure | Name | Yield |
|---|---|---|---|
| 3.2 | 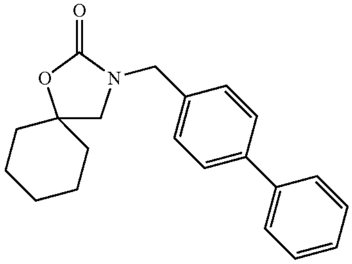 | 3-Biphenyl-4-ylmethyl-1-oxa-3-aza-spiro[4.5]decan-2-one | White powder, 69 mg, 95% |
| NMR | $^{1}$H NMR (300 MHz, $CDCl_3$): δ (ppm) = 7.62 (dd, 4 H), 7.44 (t, 2 H), 7.34 (t, 3 H), 4.49 (s, 2 H), 3.15 (s, 2 H), 1.82 (m, 4 H), 1.54 (m, 6 H) | | |
| 3.3 | 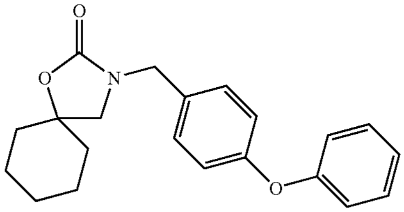 | 3-(4-Phenoxy-benzyl)-1-oxa-3-aza-spiro[4.5]decan-2-one | White powder, 69 mg, 79% |
| NMR | $^{1}$H NMR (300 MHz, $CDCl_3$): δ (ppm) = 7.4 (t, 2 H), 7.33 (t, 2 H), 7.13 (t, 1 H), 7.01 (m, 4 H), 4.41 (s, 2 H), 3.12 (s, 2 H), 1.79 (m, 4 H), 1.46 (m, 6 H) | | |
| 3.4 | 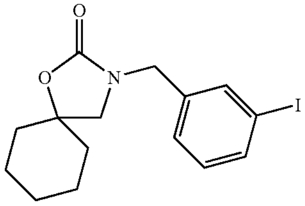 | 3-(3-Iodo-benzyl)-1-oxa-3-aza-spiro[4.5]decan-2-one | White powder, 1.0 g, 84% |
| NMR | $^{1}$H NMR (300 MHz, $CDCl_3$): □ (ppm) = 7.65 (m, 2 H), 7.27 (d, 1 H), 7.11 (t, 1 H), 4.38 (s, 2 H), 3.11 (s, 2 H), 1.81 (m, 4 H), 1.47 (m, 6 H) | | |
| 3.5 | 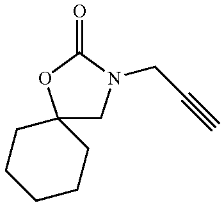 | 3-Prop-2-ynyl-1-oxa-3-aza-spiro[4.5]decan-2-one | Wine red oil, 209 mg, 100% |
| NMR | $^{1}$H NMR (300 MHz, $CDCl_3$): δ (ppm) = 4.02 (m, 2 H), 3.29 (s, 2 H), 2.27 (m, 1 H), 1.6 (m, 10 H) | | |
| 3.6 | 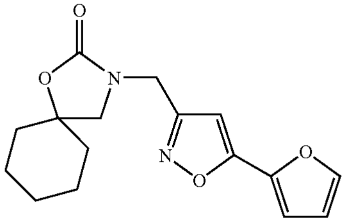 | 3-(5-Furan-2-yl-isoxazol-3-ylmethyl)-1-oxa-3-aza-spiro[4.5]decan-2-one | Yellow solid, 64 mg, 55% |
| NMR | $^{1}$H NMR (300 MHz, $CDCl_3$): δ (ppm) = 7.55 (m, 1 H), 6.92 (dd, 1 H), 6.55 (m, 1 H), 6.47 (s, 1 H), 4.53 (s, 2 H), 3.27 (s, 2 H), 1.79 (m, 4 H), 1.46 (m, 6 H) | | |

-continued

| Example | Structure | Name | Yield |
|---|---|---|---|
| 3.7 | 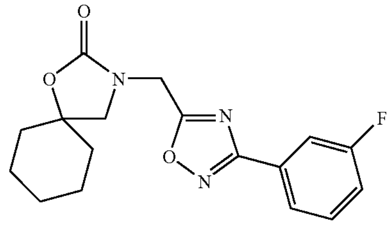 | 3-[3-(3-Fluoro-phenyl)-[1,2,4]oxadiazol-5-ylmethyl]-1-oxa-3-aza-spiro[4.5]decan-2-one | Yellow oil, 31 mg, 24% |
| NMR | $^1H$ NMR (300 MHz, $CDCl_3$): δ (ppm) = 7.88 (dd, 1 H), 7.77 (dd, 1 H), 7.49 (m, 1 H), 7.26 (m, 1 H), 4.8 (s, 2 H), 3.49 (s, 2 H), 1.95 (m, 2 H), 1.75 (m, 4 H), 1.42 (m, 4 H) | | |

Example 4.1

3-(3-Pyridin-2-yl-benzyl)-1-oxa-3-aza-spiro[4.5]decan-2-one

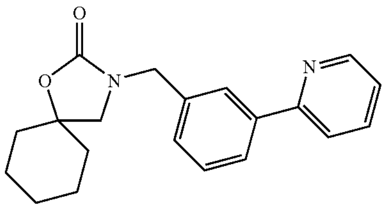

3-(3-Iodo-benzyl)-1-oxa-3-aza-spiro[4.5]decan-2-one (0.148 mmol, 55 mg), 2-tributylstannanyl-pyridine (0.222 mmol, 81.72 mg), tetrakispalladium(0) (0.03 mmol, 34.2 mg) were combined and dissolved in toluene (5 mL). The reaction mixture was left to stir at 110° C. overnight. It was then filtered through silica and the filtrate was concentrated in vacuo. The residue was purified by SPE flash column chromatography using silica gel and ethyl/acetate/hexanes (0~50%) as eluent. The product was impure by NMR. Therefore, it was dissolved in dichloromethane, and 2M hydrogen chloride in diethyl ether (10 mL) was added. This solution was concentrated in vacuo, the residue was dissolved in water (10 mL) and washed with hexanes. The aqueous layer was then neutralized using sodium bicarbonate and washed with dichloromethane. The organic layer was concentrated in vacuo to give the final product was a pale yellow gum (10 mg, 21%). $^1H$ NMR (300 MHz, $CDCl_3$): δ (ppm)=8.71 (m, 1H), 7.92 (m, 2H), 7.77 (m, 2H), 7.49 (m, 1H), 7.37 (m, 1H), 7.27 (m, 1H), 4.53 (s, 2H), 3.14 (s, 2H), 1.78 (m, 4H), 1.51 (m, 6H).

In a similar manner the following compounds were synthesized:

| Example | Structure | Name | Yield |
|---|---|---|---|
| 4.2 | 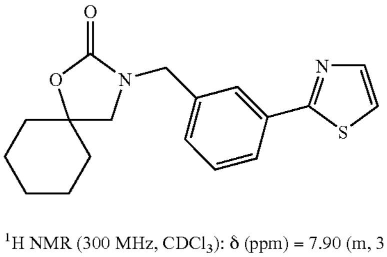 | 3-(3-Thiazol-2-yl-benzyl)-1-oxa-3-aza-spiro[4.5]decan-2-one | Yellow oil, 36 mg, 74% |
| NMR | $^1H$ NMR (300 MHz, $CDCl_3$): δ (ppm) = 7.90 (m, 3 H), 7.42 (m, 3 H), 4.50 (s, 2 H), 3.14 (s, 2 H), 1.79 (m, 4 H), 1.50 (m, 6 H) | | |
| 4.3 | 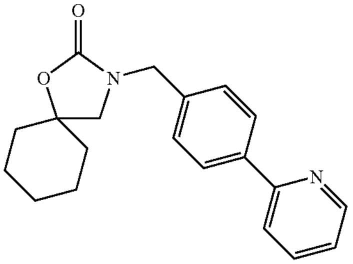 | 3-(4-Pyridin-2-yl-benzyl)-1-oxa-3-aza-spiro[4.5]decan-2-one | Off-white solid, 15 mg, 31% |

-continued

| Example | Structure | Name | Yield |
|---|---|---|---|
| NMR | $^1H$ NMR (300 MHz, $CDCl_3$): δ (ppm) = 8.7 (d, 1 H), 7.98 (d, 2 H), 7.76 (m, 2 H), 7.4 (d, 2 H), 7.21 (m, 1 H), 4.5 (s, 2 H), 3.12 (s, 2 H), 1.8 (m, 4 H), 1.39 (m, 6 H) | | |
| 4.4 | 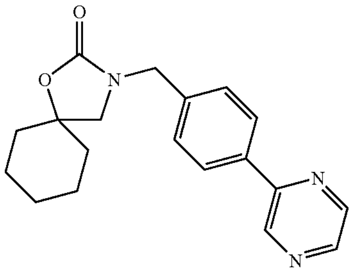 | 3-(4-Pyrazin-2-yl-benzyl)-1-oxa-3-aza-spiro[4.5]decan-2-one | Off-white solid, 5 mg, 10% |
| NMR | $^1H$ NMR (300 MHz, $CDCl_3$): δ (ppm) = 9.05 (d, 1 H), 8.66 (d, 1 H), 8.54 (d, 1 H), 8.02 (d, 2 H), 7.7 (m, 2 H), 4.52 (s, 2 H), 3.14 (s, 2 H), 1.8 (m, 4 H), 1.42 (m, 6 H) | | |
| 4.5 | 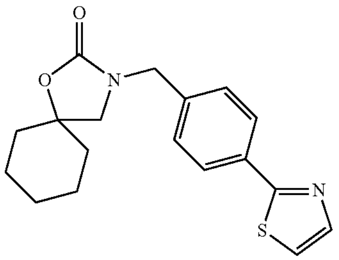 | 3-(4-Thiazol-2-yl-benzyl)-1-oxa-3-aza-spiro[4.5]decan-2-one | Pale yellow solid, 21 mg, 43% |
| NMR | $^1H$ NMR (300 MHz, $CDCl_3$): δ (ppm) = 7.97 (d, 2 H), 7.88 (d, 1 H), 7.38 (m, 3 H), 4.48 (s, 2 H), 3.12 (s, 2 H), 1.82 (m, 4 H), 1.45 (m, 6 H) | | |

Example 5.1

3-(4-Cyclohexyl-benzyl)-1-oxa-3-aza-spiro[4.5]decan-2-one

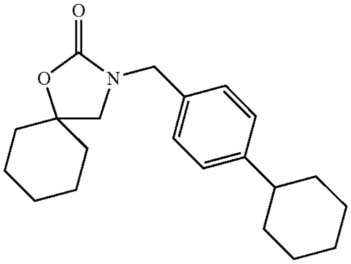

3-(4-Cyclohex-1-enyl-benzyl)-1-oxa-3-aza-spiro[4.5]decan-2-one (Example 1.31, 15 mg, 0.046 mmol) was dissolved in ethanol (3 mL) in a round bottom flask. Pd/C (5 mg) was added and the flask was flushed with hydrogen and stirred at room temperature overnight. The reaction mixture was filtered through a diatomaceous earth pad and the filtrate was concentrated in vacuo to give the title product as a white powder (15 mg, quantitative yield). $^1H$ NMR (300 MHz, $CDCl_3$): δ (ppm)=7.19 (s, 4H), 4.4 (s, 2H), 3.11 (s, 2H), 1.82 (m, 10H), 1.45 (m, 11H).

Example 6.1

[3-(5,5-Dimethyl-[1,3,2]dioxaborinan-2-yl)-benzyl]-diethyl-amine

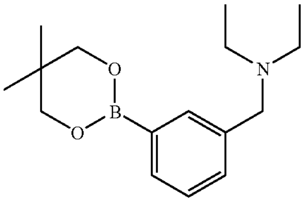

2-(3-Bromomethyl-phenyl)-5,5-dimethyl-[1,3,2]dioxaborinane (0.21 mmol, 60 mg) and diethyl-amine (1 mL, >10 equiv) were combined and left to stir at 70° C. for 4 hours. The reaction mixture was then diluted with ethyl acetate, concentrated in vacuo and dried on high vacuum for 1 hour. The residue was then dissolved in dichloromethane, washed with water, followed by brine, dried over anhydrous sodium sulfate and concentrated in vacuo to give the final product as yellow oil (37.7 mg, 65%). $^1H$ NMR (300 MHz, $CDCl_3$): δ (ppm)=7.71 (m, 2H), 7.44 (m, 1H), 7.33 (m, 1H), 3.79 (s, 4H), 3.59 (s, 2H), 2.54 (q, 4H), 1.06 (t, 6H), 1.04 (s, 6H).

In a similar manner the following compounds were synthesized:

| Example | Structure | Name | Yield |
| --- | --- | --- | --- |
| 6.2 | 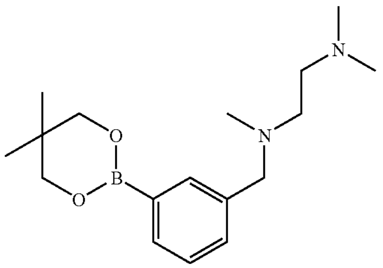 | N-[3-(5,5-Dimethyl-[1,3,2]dioxaborinan-2-yl)-benzyl]-N,N',N'-trimethyl-ethane-1,2-diamine | Yellow oil, 38.2 mg, 60% |
| NMR | $^1$H NMR (300 MHz, $CDCl_3$): δ (ppm) = 7.71 (m, 2 H), 7.38 (m, 2 H), 3.79 (s, 4 H), 3.54 (s, 2 H), 2.49 (m, 4 H), 2.27 (s, 3 H), 2.23 (s, 6 H), 1.04 (s, 6 H) | | |
| 6.3 | 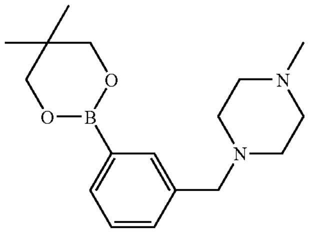 | 1-[3-(5,5-Dimethyl-[1,3,2]dioxaborinan-2-yl)-benzyl]-4-methyl-piperazine | an orange oil, 40 mg, 63% |
| NMR | $^1$H NMR (300 MHz, $CDCl_3$): δ (ppm) = 7.70 (m, 2 H), 7.42 (m, 1 H), 7.33 (m, 1 H), 3.78 (s, 4 H), 3.52 (s, 2 H), 2.44 (m, 8 H), 2.34 (s, 3 H), 1.04 (s, 6 H). | | |
| 6.4 | 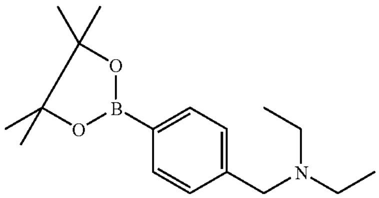 | Diethyl-[4-(4,4,5,5-tetramethyl-[1,3,2]dioxaborolan-2-yl)-benzyl]-amine | yellow solid, 114.5 mg, 99% |
| NMR | $^1$H NMR (300 MHz, $CDCl_3$): δ (ppm) = 7.78 (m, 2 H), 7.39 (m, 2 H), 3.65 (s, 2 H), 2.57 (q, 4 H), 1.35 (s, 12 H), 1.09 (t, 6 H). | | |
| 6.5 | 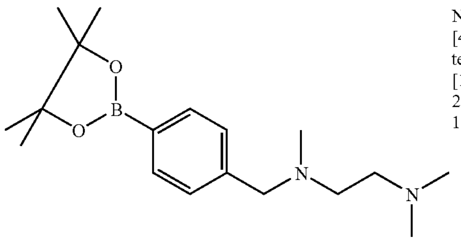 | N,N,N'-Trimethyl-N'-[4-(4,4,5,5-tetramethyl-[1,3,2]dioxaborolan-2-yl)-benzyl]-ethane-1,2-diamine | yellow oil 116 mg, 91% |
| NMR | $^1$H NMR (300 MHz, $CDCl_3$): δ (ppm) = 7.77 (m, 2 H), 7.34 (m, 2 H), 3.33 (s, 2 H), 2.47 (m, 4 H), 2.23 (m, 9 H), 1.35 (s, 12 H). | | |
| 6.6 | 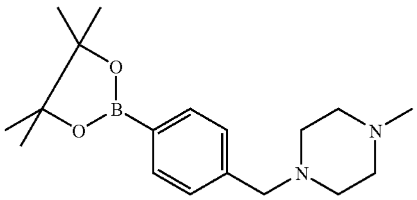 | 1-Methyl-4-[4-(4,4,5,5-tetramethyl-[1,3,2]dioxaborolan-2-yl)-benzyl]-piperazine | yellow solid, 122 mg, 96% |

-continued

| Example | Structure | Name | Yield |
|---|---|---|---|
| NMR | $^1$H NMR (300 MHz, $CDCl_3$): δ (ppm) = 7.78 (m, 2 H), 7.35 (m, 2 H), 3.53 (s, 2 H), 2.46 (m, 8 H), 2.32 (s, 3 H), 1.36 (s, 12 H). | | |
| 6.7 | 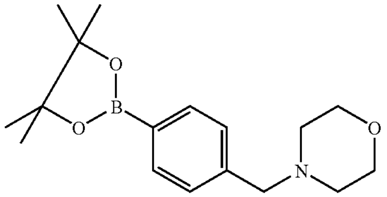 | 4-[4-(4,4,5,5-Tetramethyl-[1,3,2]dioxaborolan-2-yl)-benzyl]-morpholine | off-white solid, 96.2 mg, 79% |
| NMR | $^1$H NMR (300 MHz, $CDCl_3$): δ (ppm) = 7.78 (m, 2 H), 7.36 (m, 2 H), 3.72 (t, 4 H), 3.53 (s, 2 H), 2.45 (t, 4 H), 1.36 (s, 12 H) | | |
| 6.8 | 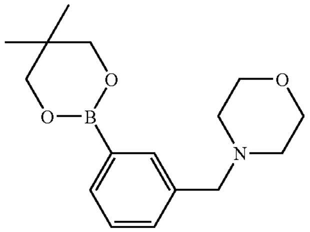 | 4-[3-(5,5-Dimethyl-[1,3,2]dioxaborinan-2-yl)-benzyl]-morpholine | yellow solid, 61.8 mg, 102% |
| NMR | $^1$H NMR (300 MHz, $CDCl_3$): δ (ppm) = 7.72 (m, 2 H), 7.43 (m, 1 H), 7.35 (m, 1 H), 3.79 (s, 4 H), 3.72 (t, 4 H), 3.52 (s, 2 H), 2.46 (t, 4 H), 1.05 (s, 6 H) | | |
| 6.9 | 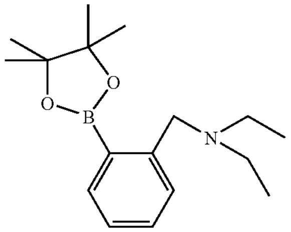 | Diethyl-[2-(4,4,5,5-tetramethyl-[1,3,2]dioxaborolan-2-yl)-benzyl]-amine | |
| NMR | $^1$H NMR (300 MHz, $CDCl_3$): δ (ppm) = 7.25 (m, 4 H), 3.77 (s, 2 H), 2.66 (q, 4 H), 1.36 (s, 12 H), 1.06 (t, 6 H) | | |
| 6.10 | 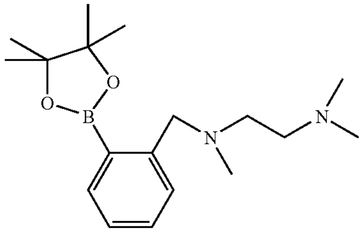 | N,N,N'-Trimethyl-N'-[2-(4,4,5,5-tetramethyl-[1,3,2]dioxaborolan-2-yl)-benzyl]-ethane-1,2-diamine | |
| NMR | $^1$H NMR (300 MHz, $CDCl_3$): δ (ppm) = 7.21 (m, 4 H), 3.82 (s, 2 H), 2.79 (m, 2 H), 2.52 (m, 2 H), 2.47 (s, 3 H), 2.27 (s, 6 H), 1.34 (s, 12 H) | | |
| 6.11 | 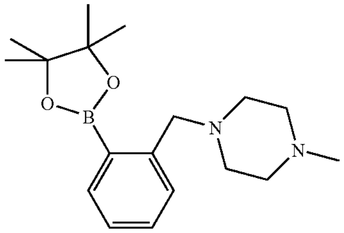 | 1-Methyl-4-[2-(4,4,5,5-tetramethyl-[1,3,2]dioxaborolan-2-yl)-benzyl]-piperazine | |
| NMR | $^1$H NMR (300 MHz, $CDCl_3$): δ (ppm) = 7.29 (m, 4 H), 3.71 (s, 2 H), 2.34 (m, 11 H), 1.36 (m, 12 H) | | |

-continued

| Example | Structure | Name | Yield |
|---|---|---|---|
| 6.12 | 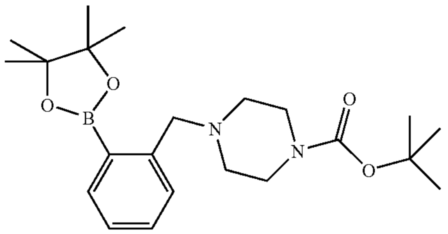 | 4-[2-(4,4,5,5-Tetramethyl-[1,3,2]dioxaborolan-2-yl)-benzyl]-piperazine-1-carboxylic acid tert-butyl ester | |
| NMR | $^1$H NMR (300 MHz, $CDCl_3$): δ (ppm) = 7.31 (m, 4 H), 3.7 (s, 2 H), 3.38 (br, 4 H), 2.37 (br, 4 H), 1.45 (s, 12 H), 1.35 (s, 9 H) | | |

Example 7.1

3-[4-(1-Methyl-1,2,3,6-tetrahydro-pyridin-4-yl)-benzyl]-1-oxa-3-aza-spiro[4.5]decan-2-one

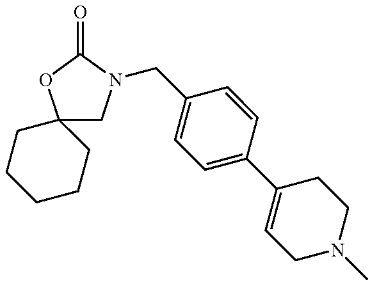

3-[4-(1,2,3,6-Tetrahydro-pyridin-4-yl)-benzyl]-1-oxa-3-aza-spiro[4.5]decan-2-one (31 mg, 0.095 mmol), formaldehyde (1.5 mL) and formic acid (1.5 mL) were mixed and heated at 100° C. for 2 hours. The reaction mixture was concentrated; the residue was dissolved in DCM (2 mL) and neutralized by adding saturated $NaHCO_3$. The aqueous phase was extracted with DCM (2×3 mL). The combined organic phase was dried over sodium sulfate and concentrated in vacuo. The crude residue was purified on silica gel eluting with 2M $NH_3$ in methanol/DCM (4: 96) to give the product as off-white solid (25 mg, 78%). $^1$H NMR (300 MHz, $CDCl_3$): δ (ppm) 7.39 (d, 2H), 7.23 (d, 2H), 6.09 (br, 1H), 4.41 (s, 2H), 3.13 (br, 2H), 3.09 (s, 2H), 2.7 (m, 2H), 2.59 (br, 2H), 2.42 (s, 3H), 1.78 (m, 4H), 1.54 (m, 6H).

In a similar manner the following compound was synthesized:

| Example | Structure | Name | Yield |
|---|---|---|---|
| 7.2 | 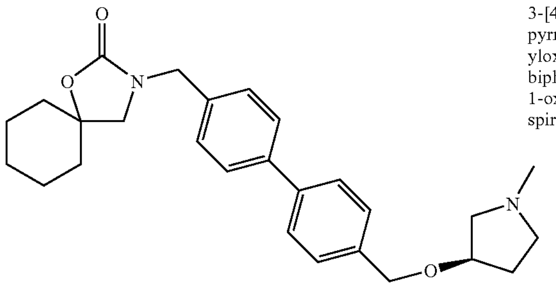 | 3-[4'-(1-Methyl-pyrrolidin-3-yloxymethyl)-biphenyl-4-ylmethyl]-1-oxa-3-aza-spiro[4.5]decan-2-one | White solid, 23 mg, 74% |
| NMR | $^1$H NMR (300 MHz, $CDCl_3$): δ (ppm) = 7.59 (dd, 4 H), 7.42 (d, 2 H), 7.33 (d, 2 H), 4.53 (s, 2 H), 4.47 (s, 2 H), 4.16 (m, 1 H), 3.14 (s, 2 H), 2.7 (m, 3 H), 2.52 (m, 1 H), 2.38 (s, 3 H), 2.16 (m, 1 H), 1.8 (m, 5 H), 1.52 (m, 6 H) | | |

Example 8.1

3-(4'-Fluoro-biphenyl-4-ylmethyl)-1-oxa-3-aza-spiro[4.5]decane-2,8-dione

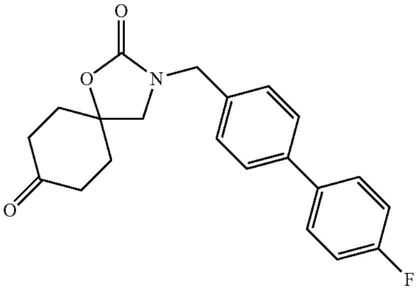

3-(4'-Fluoro-biphenyl-4-ylmethyl)-1,9,12-trioxa-3-aza-dispiro[4.2.4.2]tetradecan-2-one (50 mg, 0.126 mmol) and 10% HCl (2 mL) were mixed in THF. The reaction mixture was heated at 60° C. for 3 hours. The reaction mixture was quenched with saturated $NaHCO_3$ aqueous solution until PH=8. THF was removed under reduced pressure, and the aqueous phase was extracted with DCM (3×3 mL). The combined organic phases were dried over anhydrous sodium sulfate and condensed in vacuo. The residue was purified on silica gel eluting with 10~35% ethyl acetate in hexane to give the product as a white solid (35 mg, 78%). $^1H$ NMR (300 MHz, $CDCl_3$): δ (ppm) 7.57 (m, 4H), 7.36 (d, 2H), 7.14 (t, 2H), 4.84 (s, 2H), 3.96 (m, 2H), 3.18 (s, 2H), 2.01 (m, 4H), 1.83 (m, 2H).

Example 9.1

[4'-(2-Oxo-1-oxa-3-aza-spiro[4.5]dec-3-ylmethyl)-biphenyl-4-yl methoxy]-acetaldehyde

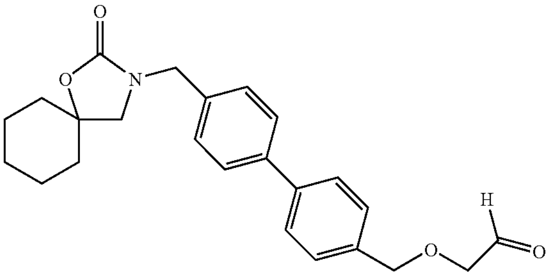

3-(4'-Allyloxymethyl-biphenyl-4-ylmethyl)-1-oxa-3-aza-spiro[4.5]decan-2-one (200 mg, 0.51 mmol) was dissolved in DCM/methanol (4:1, 7.5 mL) and was cooled to −78° C. in dry ice-acetone bath. $O_3$ was bubbled through the solution for 15 min. Thin layer chromatography (TLC) confirmed the completion of the reaction at this stage. Thiourea was added to the reaction mixture and stirred at low temperature for 0.5 hr. The cooling bath was removed and the reaction mixture was allowed to warm to room temperature, and stirred overnight. The reaction mixture was concentrated, and the residue was purified on silica gel eluting with 5~20% ethyl acetate in hexane to give the product as a white solid (80 mg, 41%). $^1H$ NMR (300 MHz, $CDCl_3$): δ (ppm) 9.76 (s, 1H), 7.63 (m, 4H), 7.44 (d, 2H), 7.35 (d, 2H), 4.7 (s, 2H), 4.47 (s, 2H), 4.16 (s, 2H), 3.14 (s, 2H), 1.78 (m, 4H), 1.45 (m, 6H).

Example 10.1

3-[4'-(2-Hydroxy-ethoxymethyl)-biphenyl-4-ylmethyl]-1-oxa-3-aza-spiro[4.5]decan-2-one

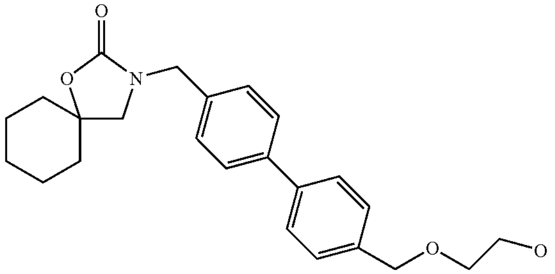

4'-(2-Oxo-1-oxa-3-aza-spiro[4.5]dec-3-ylmethyl)-biphenyl-4-yl methoxy]-acetaldehyde (110 mg, 0.279 mmol) was dissolved in ethanol (5 mL). The solution was cooled in an ice-water bath, $NaBH_4$ (53 mg, 1.39 mmol) was added at 0° C. in one shot, and the reaction mixture was stirred at 0° C. for 1 hour. The reaction mixture was quenched with saturate $NaHCO_3$ aqueous solution. The mixture was diluted with DCM (10 mL). The aqueous phase was extracted with DCM (3×8 mL). The combined organic phase was dried over sodium sulfate and concentrated to give the product as a waxy solid (99 mg, 90%). $^1H$ NMR (300 MHz, $CDCl_3$): δ (ppm) 7.65 (d, 4H), 7.42 (d, 2H), 7.32 (d, 2H), 4.73 (s, 2H), 4.61 (s, 2H), 3.79 (t, 2H), 3.69 (t, 2H), 3.14 (s, 2H), 2.3 (br, 1H), 1.8 (m, 4H), 1.47 (m, 6H).

Example 11.1

3-[4'-(2-Dimethylamino-ethoxymethyl)-biphenyl-4-ylmethyl]-1-oxa-3-aza-spiro[4.5]decan-2-one

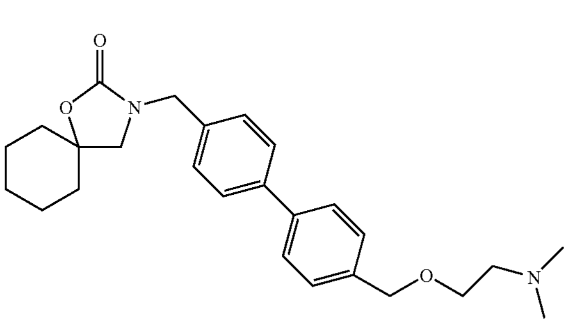

3-[4'-(2-Hydroxy-ethoxymethyl)-biphenyl-4-ylmethyl]-1-oxa-3-aza-spiro[4.5]decan-2-one (85 mg, 0.215 mmol) was mixed with triethylamine (0.09 mL, 0.644 mmol) in DCM (3 mL). The mixture was cooled in ice-water bath. Methane sulfonylchloride (3.3 uL, 0.49 mmol) was added and the reaction mixture was allowed to warm to room temperature. The stirring was continued for further 2 hours. The reaction mixture was quenched with saturate $NaHCO_3$ aqueous solution (3 mL). The aqueous phase was extracted with DCM (3×3 mL). The combined organic phase was dried over sodium sulfate and concentrated to give a brown oil which was mixed with dimethyl amine (4 mL, 6.44 mmol) in a screw cap vial and heated at 60~70° C. for 3.5 hours. The reaction mixture was concentrated, redissolved in DCM (5 mL) and stirred with saturated $NaHCO_3$ aqueous solution (3 mL). The aqueous phase was extracted with DCM (3×4 mL). The combined organic phases were dried over sodium sulfate and concentrated to give a pale brown oil, which was purified on silica gel eluting with DCM containing 1~2.5% 2M ammonia in methanol to give the product as a white solid (74 mg, 82%). $^1H$ NMR (300 MHz, $CDCl_3$): δ (ppm) 7.56 (dd, 4H), 7.41 (d, 2H), 7.29 (d, 2H), 4.64 (s, 2H), 4.45 (s, 2H), 3.56 (t, 2H), 3.12 (s, 2H), 2.54 (t, 2H), 2.27 (s, 6H), 1.75 (m, 4H), 1.52 (m, 6H).

In a similar manner the following compounds were synthesized:

Example 12.1

3-[3'-(2-Hydroxy-ethoxymethyl)-biphenyl-4-ylmethyl]-1-oxa-3-aza-spiro[4.5]decan-2-one

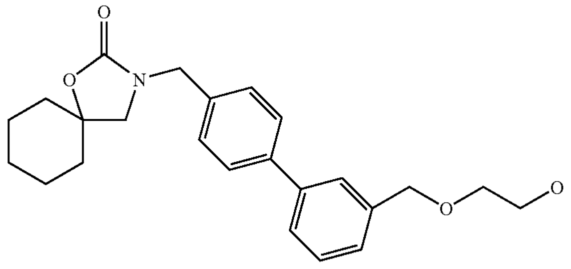

3-(3'-Allyloxymethyl-biphenyl-4-ylmethyl)-1-oxa-3-aza-spiro[4.5]decan-2-one (260 mg, 0.664 mmol) was dissolved in DCM/methanol (4:1, 7.5 mL) and was cooled to −78° C. in dry ice-acetone bath. $O_3$ was bubbled through the solution for 15 min. Thin layer chromatography (TLC) confirmed the completion of the reaction at this stage. The DCM was evapo-

| Example | Structure | Name | Yield |
|---|---|---|---|
| 11.2 | 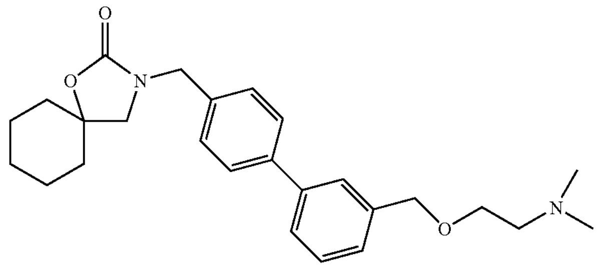 | 3-[3'-(2-Dimethylamino-ethoxymethyl)-biphenyl-4-ylmethyl]-1-oxa-3-aza-spiro[4.5]decan-2-one | Off-white solid, 53 mg, 83.7% |
| NMR | $^1H$ NMR (300 MHz, $CDCl_3$): δ (ppm) = 7.65 (d, 3 H), 7.57 (d, 1 H), 7.41 (t, 1 H), 7.31 (d, 3 H), 4.6 (s, 2 H), 4.46 (s, 2 H), 3.59 (t, 2 H), 3.13 (s, 2 H), 2.55 (t, 2 H), 2.27 (s, 6 H), 1.78 (m, 4 H), 1.48 (m, 6 H) | | |
| 11.3 | 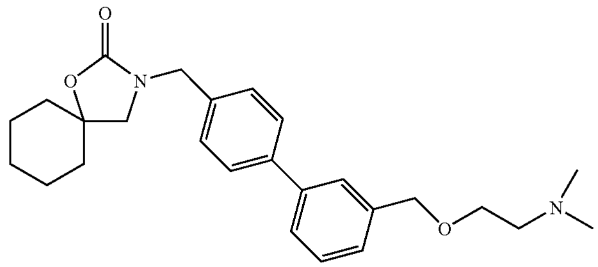 | 3-[3'-(2-Methylamino-ethoxymethyl)-biphenyl-4-ylmethyl]-1-oxa-3-aza-spiro[4.5]decan-2-one | Colorless oil, 56 mg, 91.4% |
| NMR | $^1H$ NMR (300 MHz, $CDCl_3$): δ (ppm) = 7.59 (d, 3 H), 7.56 (d, 1 H), 7.42 (t, 1 H), 7.32 (d, 3 H), 4.69 (s, 2 H), 4.58 (s, 2 H), 3.63 (t, 2 H), 3.13 (s, 2 H), 2.79 (br, 2 H), 2.44 (s, 3 H), 1.76 (m, 4 H), 1.48 (m, 7 H) | | |

rated in vacuo; ethanol (5 mL) was added and the solution was cooled in ice-water bath to 0° C. $NaBH_4$ (175 mg, 7 eq.) was added and the reaction was stirred at the temperature of 0~5° C. for one hour then at room temperature for 1.5 hour. The reaction mixture was quenched with saturated $NaHCO_3$ aqueous solution. The aqueous phase was extracted with DCM (3×8 mL), the combined organic phases were washed with brine (5 mL), dried over sodium sulfate and concentrated. The crude residue was purified on silica gel eluting with 20~50% ethyl acetate in hexane to give the product (134 mg, 51%). $^1H$ NMR (300 MHz, $CDCl_3$): δ (ppm) 7.59 (d, 3H), 7.52 (d, 1H), 7.41 (t, 1H), 7.32 (d, 3H), 4.85 (s, 2H), 4.45 (s, 2H), 3.77 (br, 2H), 3.62 (t, 2H), 3.12 (s, 2H), 2.48 (br, 1H), 1.72 (m, 4H), 1.5 (m, 6H).

In a similar manner the following compound was synthesized:

4'-(2-Oxo-1-oxa-3-aza-spiro[4.5]dec-3-ylmethyl)-biphenyl-4-carbaldehyde (50 mg, 0.143 mmol) was mixed with (R)-(−)-3-pyrrolidinol hydrochloride (20 mg, 0.157 mmol) in DCE (2.5 mL). $Na(OAc)_3BH$ was added as a solid at room temperature and the reaction was stirred overnight. The reaction was quenched with saturated aqueous $NaHCO_3$ solution. The aqueous phase was extracted with DCM (3×5 mL), the combined organic phases were washed with brine (5 mL), dried over sodium sulfate and concentrated. The crude residue was purified on silica gel eluting with DCM containing 0.5~2% 2M ammonia in methanol to give the product as off-white solid (34 mg, 56.5%). $^1H$ NMR (300 MHz, $CDCl_3$): δ (ppm) 7.59 (dd, 4H), 7.38 (d, 2H), 7.29 (d, 2H), 4.42 (s, 2H), 4.37 (m, 1H), 3.69 (s, 2H), 3.13 (s, 2H), 2.87 (m, 1H), 2.67 (d, 1H), 2.58 (dd, 1H), 2.37 (m, 2H), 2.2 (m, 1H), 1.76 (m, 4H), 1.51 (m, 6H).

| Example | Structure | Name | Yield |
|---|---|---|---|
| 12.2 | 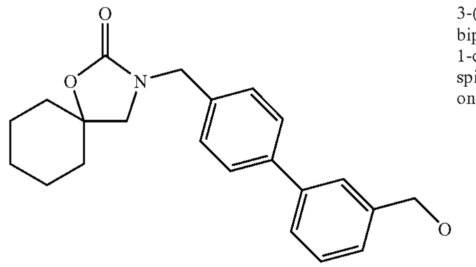 | 3-(3'-Hydroxymethyl-biphenyl-4-ylmethyl)-1-oxa-3-aza-spiro[4.5]decan-2-one | 29 mg |
| NMR | $^1H$ NMR (300 MHz, $CDCl_3$): δ (ppm) = 7.6 (d, 3 H), 7.52 (d, 1 H), 7.44 (t, 1 H), 7.35 (t, 3 H), 4.78 (br, 2 H), 4.47 (s, 2 H), 3.1 (s, 2 H), 2.05 (br, 1 H), 1.78 (m, 4 H), 1.52 (m, 6 H) | | |

Example 13.1

3-[4'-(3-Hydroxy-pyrrolidin-1-ylmethyl)-biphenyl-4-ylmethyl]-1-oxa-3-aza-spiro[4.5]decan-2-one

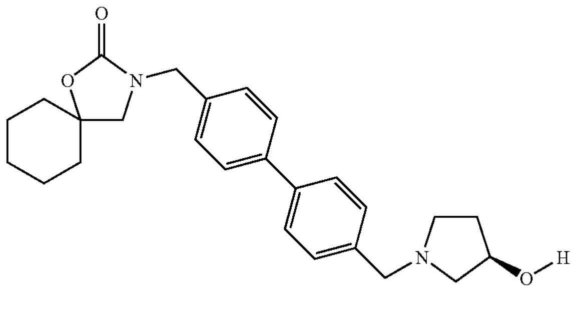

Example 14.1

(5-Bromo-pyridin-2-yl)-methanol

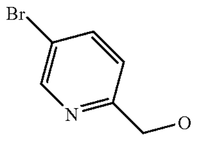

A mixture of 5-bromo-pyridine-2-carbaldehyde (0.5 g, 2.68 mmol) in ethanol (30 mL) was cooled in an ice bath. Sodium borohydride (0.41 g, 10.75 mmol) was added and the reaction mixture was stirred at room temperature for 4 hours.

The reaction mixture was concentrated, dried, the residue dissolved in dichloromethane (30 mL) and quenched with a saturated aqueous sodium bicarbonate solution. The organic phase was separated and the aqueous phase was extracted further with dichloromethane (2×10 mL). The combined organic phase was dried over sodium sulfate and concentrated to give the product as an off-white solid (426 mg, 84%). $^1$H NMR (300 MHz, $CDCl_3$): δ (ppm) 8.61 (d, 1H), 7.82 (dd, 1H), 7.23 (d, 1H), 4.73 (s, 2H), 3.92 (bs, 1H).

Example 15.1

Methanesulfonic acid 5-bromo-pyridin-2-ylmethyl ester

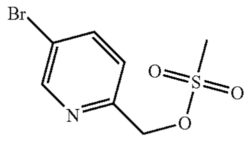

A mixture of (5-Bromo-pyridin-2-yl)-methanol (60 mg, 0.32 mmol) in dichloromethane (2 ml) was cooled in as ice bath. To the mixture was then added triethylamine (0.13 mL, 0.96 mmol) followed by methanesulfonyl chloride (0.05 mL, 0.64 mmol). The reaction mixture was stirred at room temperature for 2 hours. To the reaction mixture was added saturated aqueous sodium bicarbonate (5 mL). The organic phase was separated and the aqueous phase extracted further with dichloromethane (2×5 mL). The combined organic phase was washed with brine, dried over sodium sulfate and concentrated to give the product as a pale brown oil.

Example 16.1

3-(5-Bromo-pyridin-2-ylmethyl)-1-oxa-3-aza-spiro[4.5]decan-2-one

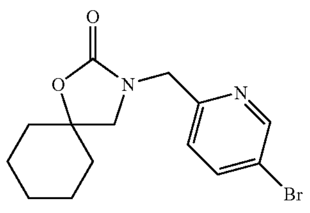

Methanesulfonic acid 5-bromo-pyridin-2-ylmethyl ester (85 mg, 0.319 mmol), cesium carbonate (312 mg, 0.957 mmol) and 1-oxa-3-aza-spiro[4.5]decan-2-one (49.5 mg, 0.319 mmol) were mixed in acetonitrile (2 mL). The reaction mixture was heated at 70° C. for 5 hours and then diluted with dichloromethane (8 mL). The mixture was washed with water (3 mL) and brine (3 mL). The combined organic phase was dried over sodium sulfate and concentrated. The residue was purified on silica gel eluting with 10 to 20% ethyl acetate in hexanes to give the product as an off-white solid (60 mg, 58%). $^1$H NMR (300 MHz, $CDCl_3$): δ 8.6 (d, 1H), 7.81 (dd, 1H), 7.23 (d, 1H), 4.49 (s, 2H), 3.27 (s, 2H), 1.79 (m, 4H), 1.47 (m, 6H).

Example 17.1

4-(4-Iodo-benzyl)-morpholine

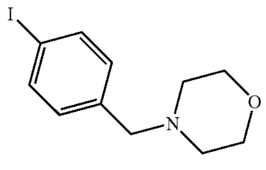

1-Bromomethyl-4-iodo-benzene (320 mg, 1.08 mmol) and morpholine (1 mL, 11.47 mmol) were combined. The reaction mixture was heated at 70° C. for 4 hours and then diluted with ethyl acetate. The resulting mixture was filtered and the filtrate was concentrated and dried. The residue was then dissolved in dichloromethane (10 mL), washed with water (4 mL), washed with brine (4 mL), dried over sodium sulfate and concentrated to give the product as an off-white solid (300 mg, 92%). $^1$H NMR (300 MHz, $CDCl_3$): δ 7.64 (d, 2H), 7.09 (d, 2H), 3.7 (t, 4H), 3.43 (s, 2H), 2.43 (t, 4H).

Example 18.1

3-[3(4-morpholin-4-ylmethyl-phenyl)-prop-2-ynyl]-1-oxa-3-aza-spiro[4.5]decan-2-one

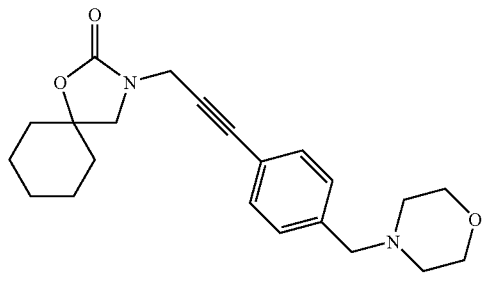

3-Prop-2-ynyl-1-oxa-3-aza-spiro[4.5]decan-2-one(55 mg, 0.284 mmol), 4-(4-iodo-benzyl)-morpholine(95 mg, 0.313 mmol), tetrakis(triphenylphosphine)palladium (17 mg, 0.0142 mmol), copper iodide (6 mg, 0.0284 mmol) and triethylamine (0.12 mL, 0.853 mmol) were mixed in acetonitrile (1 mL) under argon. The reaction mixture was stirred at room temperature for 1 hour and then diluted with dichloromethane (6 mL). The mixture was washed with water (4 mL), washed with brine (4 mL), dried over sodium sulfate and concentrated. The residue was purified on silica gel eluting with 10 to 25% ethyl acetate in hexanes. The isolated product was treated with 2M hydrochloric acid in diethyl ether to make the hydrochloric acid salt. The salt was then dissolved in water, washed with hexanes and the aqueous phase then made alkaline using aqueous saturated sodium bicarbonate. The aqueous mixture was then extracted with dichloromethane and the organic phase dried over sodium sulfate and concentrated to give the product as an off-white solid (43 mg, 41%). $^1$H NMR (300 MHz, $CDCl_3$): δ 7.38 (d, 2H), 7.29 (d, 2H), 4.31 (s, 2H), 3.71 (t, 4H), 3.49 (s, 2H), 3.4 (s, 2H), 2.43 (t, 4H), 1.83 (m, 4H), 1.54 (m, 6H).

Example 19.1

3-Fluoro-N-hydroxy-benzamidine

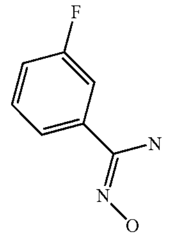

3-Fluorobenzonitrile (2.5 g, 0.021 mol), diisopropylethyl amine (10.8 mL, 0.062 mol) and hydroxylamine hydrochloride (4.3 g, 0.062 mol) were mixed in ethanol (30 mL). The reaction mixture was stirred at 70° C. overnight. The reaction mixture was cooled to room temperature and concentrated to half the original volume. The residue was added to a mixture of dichloromethane (200 mL) and water (60 mL). The mixture was basified to pH 9 using 2N NaOH and the organic phase was separated. The aqueous phase was extracted further with dichloromethane (2×50 mL) and the combined organic phase was washed with water (75 mL), washed with brine (75 mL), dried over sodium sulfate and concentrated to give the product as a yellow solid (2.8 g, 89%). $^1H$ NMR (300 MHz, $CDCl_3$): δ 8.05 (bs, 1H), 7.39 (m, 3H), 7.16 (m, 1H), 4.88 (bs, 2H).

Example 20.1

5-Chloromethyl-3-(3-fluoro-phenyl)-[1,2,4]oxadiazole

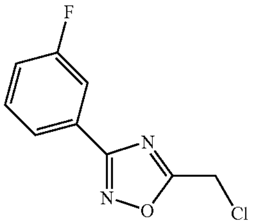

3-Fluoro-N-hydroxy-benzamidine (1.4 g, 9.08 mmol), chloroacetic acid (0.94 g, 9.99 mmol), 1-ethyl-3-(3-dimethylaminopropyl)carbodiimide hydrochloride (1.91 g, 9.99 mmol) and 1-hydroxybenzotriazole hydrate (1.35 g, 9.99 mmol) were mixed in N,N-dimethylformamide (15 mL). The reaction mixture was stirred at room temperature overnight. The reaction mixture was diluted with ethyl acetate (50 mL), washed with water (50 mL), washed with aqueous saturated sodium bicarbonate (75 mL), washed with water again (50 mL) and washed with brine (50 mL). The organic phase was dried over sodium sulfate and concentrated to give a solid. The solid was dissolved in N,N-dimethylformamide (10 mL) and the reaction mixture stirred at 120° C. for 1.5 hours. The reaction mixture was cooled to room temperature, diluted with ethyl acetate (100 mL), washed with water (3×50 mL) and washed with brine (50 mL). The organic phase was dried over sodium sulfate and concentrated. The residue was purified on silica gel eluting with 10 to 30% ethyl acetate in hexanes to give the product as a yellow oil (1.15 g, 60%). $^1H$ NMR (300 MHz, $CDCl_3$): δ 7.91 (dd, 1H), 7.82 (m, 1H), 7.5 (m, 1H), 7.25 (m, 1H), 4.78 (s, 2H).

What is claimed is:

1. A compound according to Formula I:

Formula I

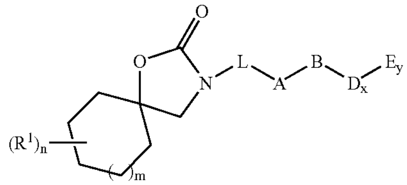

wherein:

$R^1$ is selected from the group consisting of H, hydroxy, F, Cl, Br, I, nitro, CN, alkyl, alkylhalo, O-alkyl, O-alkylhalo, alkenyl, O-alkenyl, alkynyl, O-alkynyl, methylenedioxy and ethylenedioxy;

L is selected from the group consisting of alkylene, alkenylene and alkynylene wherein any hydrogen atom of L may be independently substituted with one or more substituents selected from the group consisting of hydroxy, F, Cl, Br, I, alkyl, alkylhalo and O-alkyl;

A is selected from the group consisting of aryl and heteroaryl;

B is selected from the group consisting of alkylene, aryl, heteroaryl, cycloalkyl and heterocycloalkyl;

D is selected from the group consisting of alkylene, O, O-alkylene and alkylene-O;

E is selected from the group consisting of aryl, heteroaryl, cycloalkyl and heterocycloalkyl;

m and n are independently selected from the group consisting of 0, 1, 2, 3 and 4;

x and y are independently selected from the group consisting of 0 and 1;

wherein any of A, B and E may be substituted with up to 4 substituents independently selected from the group consisting of hydroxy, F, Cl, Br, I, nitro, CN, alkyl, alkylhalo, O-alkyl, O-alkylhalo, alkenyl, O-alkenyl, alkynyl, O-alkynyl, alkyleneOR$^2$, O-alkyleneOR$^2$, (CO)R$^2$, O(CO)R$^2$, alkyleneO(CO)R$^2$, alkylene(CO)R$^2$, O-alkylene(CO)R$^2$, $CO_2$R, alkylene$CO_2R^2$, O-alkylene$CO_2R^2$, alkylenecyano, O-alkylenecyano, O(CN)OR$^2$, NR$^2$R$^3$, alkyleneNR$^2$R$^3$, O-alkyleneNR$^2$R$^3$, (CO)NR$^2$R$^3$, alkylene(CO)NR$^2$R$^3$, O—(CO)NR$^2$R$^3$, O-alkylene(CO)NR$^2$R$^3$, NR$^2$(CO)R$^3$, alkyleneNR$^2$(CO)R$^3$, O-alkyleneNR$^2$(CO)R$^3$, NR$^2$(CO)NR$^3$R$^4$, alkyleneNR$^2$(CO)NR$^3$R$^4$, and wherein $R^2$ and $R^4$ are independently selected from the group consisting of H and alkyl;

$R^3$ is selected from the group consisting of H, alkyl and alkylene-NR$^2$R$^4$;

or a pharmaceutically acceptable salt thereof.

2. A compound according to claim 1, wherein m is 1, of Formula Ia:

Formula Ia

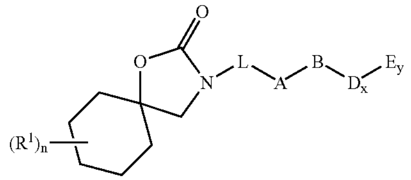

wherein $R^1$, n, L, A, B, D, E, x and y are as defined in claim 1.

3. A compound according to claim 1, wherein m is 1, and x and y are each 0, of Formula Ib:

Formula Ib

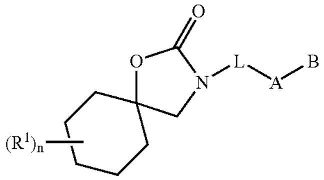

wherein $R^1$, n, L, A and B are as defined for Formula I.

4. A compound according to claim 1, wherein m is 1, x and y are each 0, A and B are both aryl wherein aryl is phenyl, of Formula Ic:

Formula Ic

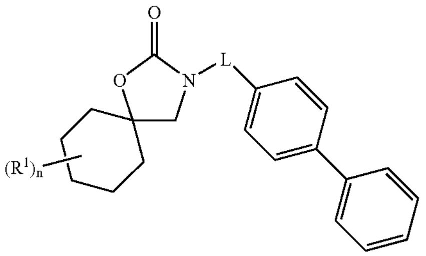

wherein $R^1$, n and L are as defined for Formula I, wherein each phenyl may be substituted with up to 4 substituents independently selected from the group consisting of hydroxy, F, Cl, Br, I, nitro, CN, alkyl, alkylhalo, O-alkyl, O-alkylhalo, alkenyl, O-alkenyl, alkynyl, O-alkynyl, alkyleneOR$^2$, O-alkyleneOR$^2$, (CO)R$^2$, O(CO)R$^2$, alkyleneO(CO)R$^2$, alkylene(CO)R$^2$, O-alkylene(CO)R$^2$, CO$_2$R, alkyleneCO$_2$R$^2$, O-alkyleneCO$_2$R$^2$, alkylenecyano, O-alkylenecyano, O(CN)OR$^2$, NR$^2$R$^3$, alkyleneNR$^2$R$^3$, O-alkyleneNR$^2$R$^3$, (CO)NR$^2$R$^3$, alkylene(CO)NR$^2$R$^3$, O—(CO)NR$^2$R$^3$, O-alkylene(CO)NR$^2$R$^3$, NR$^2$(CO)R$^3$, alkyleneNR$^2$(CO)R$^3$, O-alkyleneNR$^2$(CO)R$^3$, NR$^2$(CO)NR$^3$R$^4$, alkyleneNR$^2$(CO)NR$^3$R$^4$, and wherein $R^2$ and $R^4$ are independently selected from the group consisting of H and alkyl, and $R^3$ is selected from the group consisting of H, alkyl and alkylene-NR$^2$R$^4$.

5. A compound according to claim 1, wherein L is an alkylene group.

6. A compound according to claim 1, wherein A is an aryl group.

7. A compound according to claim 1, wherein A is a heteroaryl group.

8. A compound according to claim 1, wherein B is an aryl group.

9. A compound according to claim 1, wherein D is an alkylene group.

10. A compound according to claim 1, wherein E is a heterocycloalkyl group.

11. A pharmaceutical composition comprising a compound according to claim 1 and a pharmaceutically acceptable carrier or excipient.

12. A compound selected from the group consisting of:

3-(2'-Morpholin-4-ylmethyl-biphenyl-4-ylmethyl)-1-oxa-3-aza-spiro[4.5]decan-2-one;

3-(2'-Diethylaminomethyl-biphenyl-4-ylmethyl)-1-oxa-3-aza-spiro[4.5]decan-2-one;

3-(2'-{[(2-Dimethylamino-ethyl)-methyl-amino]-methyl}-biphenyl-4-ylmethyl)-1-oxa-3-aza-spiro[4.5]decan-2-one;

3-[2'-(4-Methyl-piperazin-1-ylmethyl)-biphenyl-4-ylmethyl]-1-oxa-3-aza-spiro[4.5]decan-2-one;

3-(2'-piperazin-1-ylmethyl-biphenyl-4-ylmethyl)-1-oxa-3-aza-spiro[4.5]decan-2-one;

3-(4'-Phenoxy-biphenyl-4-ylmethyl)-1-oxa-3-aza-spiro[4.5]decan-2-one;

3-(4-Pyridin-3-yl-benzyl)-1-oxa-3-aza-spiro[4.5]decan-2-one;

3-[4'-(4-Methyl-piperazin-1-yl)-biphenyl-4-ylmethyl]-1-oxa-3-aza-spiro[4.5]decan-2-one;

3-(4'-Fluoro-biphenyl-3-ylmethyl)-1-oxa-3-aza-spiro[4.5]decan-2-one;

3-(4'-Phenoxy-biphenyl-3-ylmethyl)-1-oxa-3-aza-spiro[4.5]decan-2-one;

3-(3-Pyridin-3-yl-benzyl)-1-oxa-3-aza-spiro[4.5]decan-2-one;

3-(4'-Fluoro-biphenyl-4-ylmethyl)-1-oxa-3-aza-spiro[4.5]decan-2-one;

3-(4-Pyridin-4-yl-benzyl)-1-oxa-3-aza-spiro[4.5]decan-2-one;

3-(4-Pyrimidin-5-yl-benzyl)-1-oxa-3-aza-spiro[4.5]decan-2-one;

3-(4-Thiophen-3-yl-benzyl)-1-oxa-3-aza-spiro[4.5]decan-2-one;

3-(4-Thiophen-2-yl-benzyl)-1-oxa-3-aza-spiro[4.5]decan-2-one;

3-(3-Thiophen-3-yl-benzyl)-1-oxa-3-aza-spiro[4.5]decan-2-one;

3-(3-Thiazol-2-yl-benzyl)-1-oxa-3-aza-spiro[4.5]decan-2-one;

3-(3'-Diethylaminomethyl-biphenyl-3-ylmethyl)-1-oxa-3-aza-spiro[4.5]decan-2-one;

3-(3'-{[(2-Dimethylamino-ethyl)-methyl-amino]-methyl}-biphenyl-3-ylmethyl)-1-oxa-3-aza-spiro[4.5]decan-2-one;

3-[3'-(4-Methyl-piperazin-1-ylmethyl)-biphenyl-3-ylmethyl]-1-oxa-3-aza-spiro[4.5]decan-2-one;

3-(4'-Diethylamino methyl-biphenyl-4-ylmethyl)-1-oxa-3-aza-spiro[4.5]decan-2-one;

3-(4'-{[(2-Dimethylamino-ethyl)-methyl-amino]-methyl}-biphenyl-4-ylmethyl)-1-oxa-3-aza-spiro[4.5]decan-2-one;

3-[4'-(4-Methyl-piperazin-1-ylmethyl)-biphenyl-4-ylmethyl]-1-oxa-3-aza-spiro[4.5]decan-2-one;

3-(4'-Morpholin-4-ylmethyl-biphenyl-4-ylmethyl)-1-oxa-3-aza-spiro[4.5]decan-2-one;

3-(3'-Morpholin-4-ylmethyl-biphenyl-3-ylmethyl)-1-oxa-3-aza-spiro[4.5]decan-2-one;

3-(4'-Diethylaminomethyl-biphenyl-3-ylmethyl)-1-oxa-3-aza-spiro[4.5]decan-2-one;

3-(4'-{[(2-Dimethylamino-ethyl)-methyl-amino]-methyl}-biphenyl-3-ylmethyl)-1-oxa-3-aza-spiro[4.5]decan-2-one;
4'-(2-Oxo-1-oxa-3-aza-spiro[4.5]dec-3-ylmethyl)-biphenyl-3-carboxylic acid (2-dimethylamino-ethyl)-amide;
3-{4-[6-(2-Morpholin-4-yl-ethylamino)-pyridin-3-yl]-benzyl}-1-oxa-3-aza-spiro[4.5]decan-2-one;
3-(4-Cyclohex-1-enyl-benzyl)-1-oxa-3-aza-spiro[4.5]decan-2-one;
3-[4'-(4-Methyl-piperazin-1-ylmethyl)-biphenyl-3-ylmethyl]-1-oxa-3-aza-spiro[4.5]decan-2-one;
3-(4'-Morpholin-4-ylmethyl-biphenyl-3-ylmethyl)-1-oxa-3-aza-spiro[4.5]decan-2-one;
3-(3'-Diethylamino methyl-biphenyl-4-ylmethyl)-1-oxa-3-aza-spiro[4.5]decan-2-one;
3-(3'-{[(2-Dimethylamino-ethyl)-methyl-amino]-methyl}-biphenyl-4-ylmethyl)-1-oxa-3-aza-spiro[4.5]decan-2-one;
3-[3'-(4-Methyl-piperazin-1-ylmethyl)-biphenyl-4-ylmethyl]-1-oxa-3-aza-spiro[4.5]decan-2-one;
3-(3'-Morpholin-4-ylmethyl-biphenyl-4-ylmethyl)-1-oxa-3-aza-spiro[4.5]decan-2-one;
3-(2'-Fluoro-biphenyl-4-ylmethyl)-1-oxa-3-aza-spiro[4.5]decan-2-one;
3-(3'-Fluoro-biphenyl-4-ylmethyl)-1-oxa-3-aza-spiro[4.5]decan-2-one;
4'-(2-Oxo-1-oxa-3-aza-spiro[4.5]dec-3-ylmethyl)-biphenyl-3-carbonitrile;
4'-(2-Oxo-1-oxa-3-aza-spiro[4.5]dec-3-ylmethyl)-biphenyl-4-carbonitrile;
3-(3'-Methoxy-biphenyl-4-ylmethyl)-1-oxa-3-aza-spiro[4.5]decan-2-one;
3-(4'-Methoxy-biphenyl-4-ylmethyl)-1-oxa-3-aza-spiro[4.5]decan-2-one;
3-(2',4'-Difluoro-biphenyl-4-ylmethyl)-1-oxa-3-aza-spiro[4.5]decan-2-one;
3-(3',5'-Difluoro-biphenyl-4-ylmethyl)-1-oxa-3-aza-spiro[4.5]decan-2-one;
3-(3',4'-Dimethoxy-biphenyl-4-ylmethyl)-1-oxa-3-aza-spiro[4.5]decan-2-one;
3-(2'-Methoxymethyl-biphenyl-4-ylmethyl)-1-oxa-3-aza-spiro[4.5]decan-2-one;
3-[4-(1,2,3,6-Tetrahydro-pyridin-4-yl)-benzyl]-1-oxa-3-aza-spiro[4.5]decan-2-one;
3-(4'-Fluoro-biphenyl-4-ylmethyl)-1,9,12-trioxa-3-aza-dispiro[4.2.4.2]tetradecan-2-one;
3-(4'-Allyloxymethyl-biphenyl-4-ylmethyl)-1-oxa-3-aza-spiro[4.5]decan-2-one;
3-[4'-(3-Hydroxy-pyrrolidin-1-ylmethyl)-biphenyl-4-ylmethyl]-1-oxa-3-aza-spiro[4.5]decan-2-one;
3-[4'-(Pyrrolidin-3-yloxymethyl)-biphenyl-4-ylmethyl]-1-oxa-3-aza-spiro[4.5]decan-2-one;
3-(3'-Allyloxymethyl-biphenyl-4-ylmethyl)-1-oxa-3-aza-spiro[4.5]decan-2-one;
4'-(2-Oxo-1-oxa-3-aza-spiro[4.5]dec-3-ylmethyl)-biphenyl-4-carbaldehyde;
3-(3-Pyridin-4-yl-benzyl)-1-oxa-3-aza-spiro[4.5]decan-2-one;
3-[5-(4-Fluoro-phenyl)-pyridin-2-ylmethyl]-1-oxa-3-aza-spiro[4.5]decan-2-one;
3-(5-Cyclohex-1-enyl-pyridin-2-ylmethyl)-1-oxa-3-aza-spiro[4.5]decan-2-one;
3-Biphenyl-4-ylmethyl-1-oxa-3-aza-spiro[4.5]decan-2-one;
3-(4-Phenoxy-benzyl)-1-oxa-3-aza-spiro[4.5]decan-2-one;
3-(5-Furan-2-yl-isoxazol-3-ylmethyl)-1-oxa-3-aza-spiro[4.5]decan-2-one;
3-[3-(3-Fluoro-phenyl)-[1,2,4]oxadiazol-5-ylmethyl]-1-oxa-3-aza-spiro[4.5]decan-2-one;
3-(3-Pyridin-2-yl-benzyl)-1-oxa-3-aza-spiro[4.5]decan-2-one;
3-(3-Thiazol-2-yl-benzyl)-1-oxa-3-aza-spiro[4.5]decan-2-one;
3-(4-Pyridin-2-yl-benzyl)-1-oxa-3-aza-spiro[4.5]decan-2-one;
3-(4-Pyrazin-2-yl-benzyl)-1-oxa-3-aza-spiro[4.5]decan-2-one;
3-(4-Thiazol-2-yl-benzyl)-1-oxa-3-aza-spiro[4.5]decan-2-one;
3-(4-Cyclohexyl-benzyl)-1-oxa-3-aza-spiro[4.5]decan-2-one;
3-[4-(1-Methyl-1,2,3,6-tetrahydro-pyridin-4-yl)-benzyl]-1-oxa-3-aza-spiro[4.5]decan-2-one;
3-[4'-(1-Methyl-pyrrolidin-3-yloxymethyl)-biphenyl-4-ylmethyl]-1-oxa-3-aza-spiro[4.5]decan-2-one;
3-(4'-Fluoro-biphenyl-4-ylmethyl)-1-oxa-3-aza-spiro[4.5]decane-2,8-dione;
[4'-(2-Oxo-1-oxa-3-aza-spiro[4.5]dec-3-ylmethyl)-biphenyl-4-yl methoxy]-acetaldehyde;
3-[4'-(2-Hydroxy-ethoxymethyl)-biphenyl-4-ylmethyl]-1-oxa-3-aza-spiro[4.5]decan-2-one;
3-[4'-(2-Dimethylamino-ethoxymethyl)-biphenyl-4-ylmethyl]-1-oxa-3-aza-spiro[4.5]decan-2-one;
3-[3'-(2-Dimethylamino-ethoxymethyl)-biphenyl-4-ylmethyl]-1-oxa-3-aza-spiro[4.5]decan-2-one;
3-[3'-(2-Methylamino-ethoxymethyl)-biphenyl-4-ylmethyl]-1-oxa-3-aza-spiro[4.5]decan-2-one;
3-[3'-(2-Hydroxy-ethoxymethyl)-biphenyl-4-ylmethyl]-1-oxa-3-aza-spiro[4.5]decan-2-one;
3-(3'-Hydroxymethyl-biphenyl-4-ylmethyl)-1-oxa-3-aza-spiro[4.5]decan-2-one;
3-[4'-(3-Hydroxy-pyrrolidin-1-ylmethyl)-biphenyl-4-ylmethyl]-1-oxa-3-aza-spiro[4.5]decan-2-one; and
3-[3(4-morpholin-4-ylmethyl-phenyl)-prop-2-ynyl]-1-oxa-3-aza-spiro[4.5]decan-2-one.

13. A compound according to claim 12 selected from the group consisting of:
3-(2'-Morpholin-4-ylmethyl-biphenyl-4-ylmethyl)-1-oxa-3-aza-spiro[4.5]decan-2-one;
3-(4'-Phenoxy-biphenyl-4-ylmethyl)-1-oxa-3-aza-spiro[4.5]decan-2-one;
3-(4'-Fluoro-biphenyl-4-ylmethyl)-1,9,12-trioxa-3-aza-dispiro[4.2.4.2]tetradecan-2-one, and
3-Biphenyl-4-ylmethyl-1-oxa-3-aza-spiro[4.5]decan-2-one.

* * * * *